United States Patent
Reddy et al.

(10) Patent No.: US 11,918,571 B2
(45) Date of Patent: Mar. 5, 2024

(54) COMPOUNDS AND THEIR METHODS OF USE

(71) Applicant: Praxis Precision Medicines, Inc., Cambridge, MA (US)

(72) Inventors: Kiran Reddy, Boston, MA (US); Gabriel Martinez Botella, Wayland, MA (US); Andrew Mark Griffin, L'lle Bizard (CA); Brian Edward Marron, Ada, MI (US)

(73) Assignee: Praxis Precision Medicines, Inc., Boston, MA (US)

( * ) Notice: Subject to any disclaimer, the term of this patent is extended or adjusted under 35 U.S.C. 154(b) by 176 days.

(21) Appl. No.: 17/686,979

(22) Filed: Mar. 4, 2022

(65) Prior Publication Data
US 2022/0218681 A1   Jul. 14, 2022

Related U.S. Application Data

(63) Continuation of application No. 16/638,725, filed as application No. PCT/US2018/000224 on Aug. 15, 2018, now Pat. No. 11,278,535.

(60) Provisional application No. 62/676,615, filed on May 25, 2018, provisional application No. 62/545,555, filed on Aug. 15, 2017.

(51) Int. Cl.
   *A61K 31/444*    (2006.01)
   *A61K 31/437*    (2006.01)
   *A61P 25/08*     (2006.01)

(52) U.S. Cl.
   CPC .......... *A61K 31/444* (2013.01); *A61K 31/437* (2013.01); *A61P 25/08* (2018.01)

(58) Field of Classification Search
   CPC .................................................. A61K 31/444
   See application file for complete search history.

(56) References Cited

U.S. PATENT DOCUMENTS

| | | | |
|---|---|---|---|
| 3,845,770 A | 11/1974 | Theeuwes et al. | |
| 4,112,095 A | 9/1978 | Allen, Jr. et al. | |
| 4,230,705 A | 10/1980 | Allen, Jr. et al. | |
| 4,242,515 A | 12/1980 | Trust et al. | |
| 4,326,525 A | 4/1982 | Swanson et al. | |
| 4,902,514 A | 2/1990 | Barclay et al. | |
| 4,992,445 A | 2/1991 | Lawter et al. | |
| 5,001,139 A | 3/1991 | Lawter et al. | |
| 5,023,252 A | 6/1991 | Hsieh et al. | |
| 5,616,345 A | 4/1997 | Geoghegan et al. | |
| 5,905,079 A | 5/1999 | Sargent et al. | |
| 6,589,952 B2 | 7/2003 | Bakthavatchalam et al. | |
| 7,863,279 B2 | 1/2011 | Even et al. | |
| 8,030,305 B2 | 10/2011 | Lu et al. | |
| 8,173,654 B2 | 5/2012 | Lu et al. | |
| 8,198,448 B2 | 6/2012 | Albrecht et al. | |
| 8,212,041 B2 | 7/2012 | Albrecht et al. | |
| 8,217,177 B2 | 7/2012 | Albrecht et al. | |
| 8,524,900 B2 | 9/2013 | Albrecht et al. | |
| 8,937,060 B2 | 1/2015 | Cid-Nunez et al. | |
| 8,952,034 B2 | 2/2015 | Corkey et al. | |
| 9,066,954 B2 | 6/2015 | Albrecht et al. | |
| 9,371,329 B2 | 6/2016 | Corkey et al. | |
| 10,280,184 B2 | 5/2019 | Friedman et al. | |
| 11,014,931 B2 | 5/2021 | Griffin et al. | |
| 2002/0049208 A1 | 4/2002 | Bakthavatchalam et al. | |
| 2009/0124609 A1 | 5/2009 | Albrecht et al. | |
| 2009/0203707 A1 | 8/2009 | Rajamani et al. | |
| 2010/0088778 A1 | 4/2010 | Mulley et al. | |
| 2011/0021521 A1 | 1/2011 | Corkey et al. | |
| 2012/0010192 A1 | 1/2012 | Kobayashi et al. | |
| 2012/0065191 A1 | 3/2012 | Kiss et al. | |
| 2012/0245164 A1 | 9/2012 | Auger et al. | |
| 2013/0315895 A1 | 11/2013 | Farrell et al. | |
| 2014/0066443 A1 | 3/2014 | Beshore et al. | |
| 2014/0303158 A1 | 10/2014 | Corkey et al. | |
| 2015/0038503 A1 | 2/2015 | Bourotte et al. | |
| 2016/0159801 A1 | 6/2016 | Quinn et al. | |
| 2016/0235718 A1 | 8/2016 | Baraban | |
| 2016/0297799 A1 | 10/2016 | Brookings et al. | |
| 2016/0317536 A1 | 11/2016 | Reich et al. | |
| 2019/0389868 A1 | 12/2019 | Reddy et al. | |
| 2020/0179358 A1 | 6/2020 | Reddy et al. | |
| 2020/0247793 A1 | 8/2020 | Reddy et al. | |
| 2020/0377499 A1 | 12/2020 | Griffin et al. | |
| 2020/0377506 A1 | 12/2020 | Reddy et al. | |

(Continued)

FOREIGN PATENT DOCUMENTS

| JP | 2017001991 A | 1/2017 |
|---|---|---|
| WO | 2006061428 A2 | 6/2006 |

(Continued)

OTHER PUBLICATIONS

US 8,754,103 B2, 06/2014, Corkey et al. (withdrawn)

(Continued)

*Primary Examiner* — Nizal S Chandrakumar
(74) *Attorney, Agent, or Firm* — McCarter & English, LLP; Jonathan M. Sparks; Yelena Margolin

(57) ABSTRACT

The present invention is directed to, in part, fused heteroaryl compounds and compositions useful for preventing and/or treating a disease or condition relating to aberrant function of a voltage-gated, sodium ion channel, for example, abnormal late/persistent sodium current. Methods of treating a disease or condition relating to aberrant function of a sodium ion channel including neurological disorders (e.g., Dravet syndrome, epilepsy), pain, and neuromuscular disorders are also provided herein.

19 Claims, No Drawings

(56) References Cited

U.S. PATENT DOCUMENTS

| | | |
|---|---|---|
| 2020/0377507 A1 | 12/2020 | Griffin et al. |
| 2021/0087197 A1 | 3/2021 | Griffin et al. |
| 2021/0163488 A1 | 6/2021 | Griffin et al. |
| 2021/0171530 A1 | 6/2021 | Reddy et al. |
| 2021/0188839 A1 | 6/2021 | Reddy et al. |
| 2021/0188852 A1 | 6/2021 | Reddy et al. |

FOREIGN PATENT DOCUMENTS

| | | |
|---|---|---|
| WO | 2007075567 A1 | 7/2007 |
| WO | 2008008539 A2 | 1/2008 |
| WO | 2010053757 A1 | 5/2010 |
| WO | 2010056865 A1 | 5/2010 |
| WO | 2010074807 A1 | 7/2010 |
| WO | 2011014462 A1 | 2/2011 |
| WO | 2011056985 A2 | 5/2011 |
| WO | 2012003392 A1 | 1/2012 |
| WO | 2012065546 A1 | 5/2012 |
| WO | 2012154760 A1 | 11/2012 |
| WO | 2013006463 A1 | 1/2013 |
| WO | 2013043925 A1 | 3/2013 |
| WO | 2014179492 A1 | 11/2014 |
| WO | 2015095370 A1 | 6/2015 |
| WO | 2015158283 A1 | 10/2015 |
| WO | 2015194670 A1 | 12/2015 |
| WO | 2015197567 A1 | 12/2015 |
| WO | 2018067786 A1 | 4/2018 |
| WO | 2018098491 A1 | 5/2018 |
| WO | 2018098499 A1 | 5/2018 |
| WO | 2018098500 A1 | 5/2018 |
| WO | 2018148745 A1 | 8/2018 |
| WO | 2018187480 A1 | 10/2018 |
| WO | 2019035951 A1 | 2/2019 |
| WO | 2019232209 A1 | 12/2019 |
| WO | 2020069322 A1 | 4/2020 |
| WO | 2021108513 A1 | 6/2021 |
| WO | 2021108625 A1 | 6/2021 |

OTHER PUBLICATIONS

Berge et al., "Pharmaceutical salts," J. Pharmaceutical Sciences, 66(1):1-19 (1977).
Burbano et al., "Characterization of a Novel Knock-in Mouse Model of KCNT1 Epileptic Encephalopathy (P2.273)," Neurology, 90 (15 Supplement), (2018), 2 pages. Abstract Only.
Chaplan et al., "Quantitative assessment of tactile allodynia in the rat paw," J. Neurosci Meth., (1994), 53:55-63.
Flynn et al., "Correlation and Prediction of Mass Transport across Membranes I: Influence of Alkyl Chain Length on Flux-Determining Properties of Barrier and Diffusant," Journal of Pharmaceutical Sciences, (1972), 61(6):838-852.
Fukaya et al., "Identification of a Novel Benzoxazolone Derivative as a Selective, Orally Active 18 kDa Translocator Protein (TSPO) Ligand," J. of Med. Chem., (2013), 56(20): 8191-8195.
Hackam et al., "Translation of research evidence from animals to humans," JAMA, (2006), 296(14):1731-1732.
Jordan et al., "Tamoxifen: a most unlikely pioneering medicine," Nat Rev Drug Discov., (2003), 2(3):205-213.
Kearney et al., "A gain-of-function mutation in the sodium channel gene Scn2a results in seizures and behavioral abnormalities," Neuroscience, (2001), 702(2):307-317. Abstract Only.
Kim et al., "An experimental model for peripheral neuropathy produced by segmental spinal nerve ligation in the rat," Pain, (1992), 50:355-363.
Li et al., "Antisense oligonucleotide therapy for SCN2A gain-of-function epilepsies," American Epilepsy Society, (2018), 28 pages.
Patel et al., (2019). "Neuropathy following spinal nerve injury shares features with the irritable nociceptor phenotype: A back-translational study of oxcarbazepine," Eur J Pain, 23:183-197.
Petrou et al., (2018). "Abstract: Antisense oligonucleotide therapy for SCN2A gain-of-function epilepsies," American Epilepsy Society, available online at <https://www.aesnet.org/abstractslisting/antisense-oligonucleotide-therapy-for-scn2a-gain-of-function-epilepsies>, 2 pages.
Wagnon et al., (2015). "Convulsive seizures and SUDEP in a mouse model of SCN8A epileptic encephalopathy," Human Molecular Genetics, 24(2):506-515.
Wilen et al., (1977). "Strategies in optical resolutions," Tetrahedron, 33(21):2725-2736.
Woodland et al., (2015). "Discovery of Inhibitors of Trypanosoma brucei by Phenotypic Screening of a Focused Protein Kinase Library," ChemMedChem, 10(11): 1809-1820.
Dorwald F. A. Side Reactions in Organic Synthesis, 2005, Wiley: VCH, Weinheim p. IX of Preface p. 1-15.
Venkatesh, J. Pharm. Sci. 89, 145-154 (2000) (p. 146, left column).
J. G. Cannon, Chapter Nineteen in Burger's Medicinal Chemistry and Drug Dsicovery, Fifth Edition, vol. I: Principles and Practice, Wiley-Interscience 1995, pp. 783-802, 784.
Zaza et al., (2008). "Pathophysiology and pharmacology of the cardiac late sodium current," Pharmacology Therapeutics, 119(3):326-339.
International Preliminary Report on Patentability for International Patent Application No. PCT/US2018/018044 filed on Feb. 13, 2018, 7 pages.
International Preliminary Report on Patentability for International Patent Application No. PCT/US2018/026099 filed on Apr. 4, 2018, 6 pages.
International Preliminary Report on Patentability for International Patent Application No. PCT/US2017/063507 filed on Nov. 28, 2017, 6 pages.
International Preliminary Report on Patentability for International Patent Application No. PCT/US2017/063534 filed on Nov. 28, 2017, 8 pages.
International Preliminary Report on Patentability for International Patent Application No. PCT/US2018/000224 filed on Aug. 15, 2018, 6 pages.
International Search Report and Written Opinion dated Feb. 25, 2021, for PCT Application No. PCT/US2020/062179 filed on Nov. 25, 2020, 7 pages.
International Search Report and Written Opinion received for International Patent Application No. PCT/US2020/062317, dated Apr. 6, 2021, 14 pages.
Non-Final Office Action received for U.S. Appl. No. 16/887,906 dated Jun. 10, 2021, 18 pages.
Non-Final Office Action received for U.S. Appl. No. 16/464,483 dated Jun. 30, 2021, 22 pages.
Non-Final Office Action received for U.S. Appl. No. 16/485,581 dated Mar. 10, 2021, 8 pages.
Non-Final Office Action received for U.S. Appl. No. 17/102,586 dated Jan. 26, 2021, 14 pages.
Albright et al. "Synthesis and anxiolytic activity of 6-(substituted-phenyl)-1,2,4-triazolo[4,3-b]pyridazines," J. Med. Chem. (1981) vol. 24, pp. 592-600.
Anderson et al. "Unexpected efficacy of a novel sodium channel modulator in Dravet Syndrome," Scientific Reports. 2017.
Anderson et al., "Antiepileptic activity of preferential inhibitors of persistent sodium current," Epilepsia (2014), 55(8), 1274-1283.
Baker et al. "The novel sodium channel modulator GS-458967 (GS967) is an effective treatment in a mouse model of SCN8A encephalopathy," Epilepsia, 2018, 1166-1176.
Barbieri et al. "Late sodium current blocker GS967 inhibits persistent currents induced by familial hemiplegic migraine type 3 mutations of the SCN1A gene," The Journal of Headache and Pain (2019) vol. 20, No. 107, pp. 1-13.
Belardinelli et al. "A Novel, Potent, and Selective Inhibitor of Cardiac Late Sodium Current Suppresses Experimental Arrhythmias," J. Pharmacol. Exp. Ther. (2013) vol. 344, pp. 23-32.
Guan et al. "Synthesis and anticonvulsant activity of a new 6-alkoxy-[1,2,4]-triazolo[4,3-b]pyridazine," Eur. J. Med. Chem. (2010) vol. 45, pp. 1746-1752.
Koltun et al. "Discovery of triazolopyridinone GS-462808, a late sodium current inhibitor {Late INai} of the cardiac Nav1.5 channel with improved efficacy and potency relative to ranolazine," Bioorg. Med. Chem. Lett. (2016) vol. 26, pp. 3207-3211.

(56) References Cited

OTHER PUBLICATIONS

Pubchem-CID 58763997 Create Date: Aug. 19, 2012 (14 pages).
Pubchem-CID 597467 Create Date: Mar. 27, 2005 (15 pages).
Pubchem-CID 82381512 Create Date: Oct. 20, 2014 (10 pages).
Pubchem-CID 89077556 Create Date: Feb. 13, 2015 (11 pages).
STN Chemical Structure Search Results (dated Apr. 14, 2019). (36 pages).
STN Chemical Structure Search Results (dated Apr. 2018). (55 pages).
STN Chemical Structure Search Results (dated Apr. 23, 2019). (45 pages).
STN Chemical Structure Search Results (dated Feb. 2018). (29 pages).
STN Chemical Structure Search Results (dated Jan. 15, 2020). (22 pages).
STN Chemical Structure Search Results (dated Jan. 2018). (23 pages).
STN Chemical Structure Search Results (dated Mar. 20, 2018). (264 pages).
STN Chemical Structure Search Results (dated Mar. 20, 2018). (83 pages).
STN Chemical Structure Search Results (dated Mar. 6, 2017). (480 pages).
STN Chemical Structure Search Results (dated Mar. 6, 2017). (511 pages).
STN Chemical Structure Search Results (dated May 18, 2016). (102 pages).
STN Chemical Structure Search Results (dated Nov. 1, 2017). (107 pages).
STN Chemical Structure Search Results (dated Nov. 21, 2017). (85 pages).
STN Chemical Structure Search Results (dated Nov. 3, 2017). (57 pages).
STN Chemical Structure Search Results (dated Nov. 6, 2017). (123 pages).
STN Chemical Structure Search Results (dated Nov. 6, 2017). (7 pages).
Wengert et al. "Prax330 reduces persistent and resurgent sodium channel currents and neuronal hyperexcitability of subiculum neurons in a mouse model of SCN8A epileptic encephalopathy," Neuropharmacology (2019) vol. 158, No. 107699, pp. 1-11.
Written Opinion of the International Searching Authority and International Search Report for PCT/US2017/063507 dated Mar. 29, 2019 (9 pages).
Written Opinion of the International Searching Authority and International Search Report for PCT/US2017/063533 dated Mar. 29, 2019 (10 pages).
Written Opinion of the International Searching Authority and International Search Report for PCT/US2017/063534 dated Mar. 28, 2019 (11 pages).
Written Opinion of the International Searching Authority and International Search Report for PCT/US2018/00224 dated Nov. 5, 2018 (8 pages).
Written Opinion of the International Searching Authority and International Search Report for PCT/US2018/018044 dated May 24, 2018 (10 pages).
Written Opinion of the International Searching Authority and International Search Report for PCT/US2018/026099 dated Aug. 10, 2018 (9 pages).
Written Opinion of the International Searching Authority and International Search Report for PCT/US2019/034653 dated Aug. 9, 2019 (9 pages).
Written Opinion of the International Searching Authority and International Search Report for PCT/US2019/053467 dated Jan. 14, 2020 (9 pages).
Zablocki et al. "Discovery of Dihydrobenzoxazepinone (GS-6615) Late Sodium Current Inhibitor {Late INai), a Phase II Agent with Demonstrated Preclinical Anli-Ischemic and Antiarrhythmic Properties," Journal of Medicinal Chemistry (2016) vol. 59, pp. 9005-9017.

COMPOUNDS AND THEIR METHODS OF USE

CROSS REFERENCE TO RELATED APPLICATIONS

This application is a continuation application of U.S. application Ser. No. 16/638,725, filed on Feb. 12, 2020, which is the national stage of International (PCT) Patent Application Serial Number PCT/US2018/000224, filed Aug. 15, 2018 and which claims priority to and the benefit of U.S. Provisional Patent Application No. 62/545,555, filed Aug. 15, 2017 and U.S. Provisional Patent Application No. 62/676,615, filed on May 25, 2018, each of which is incorporated herein by reference in its entirety.

BACKGROUND

Sodium ion (Na+) channels primarily open in a transient manner and are quickly inactivated, thereby generating a fast Na+ current to initiate the action potential. The late or persistent sodium current (INaL) is a sustained component of the fast Na+ current of cardiac myocytes and neurons. Many common neurological and cardiac conditions are associated with abnormal INaL enhancement, which contributes to the pathogenesis of both electrical and contractile dysfunction in mammals (see, e.g., Pharmacol Ther (2008) 119:326-339). Accordingly, pharmaceutical compounds that selectively modulate sodium channel activity, e.g., abnormal INaL, are useful in treating such disease states.

SUMMARY OF THE INVENTION

Described herein are fused heteroaryl compounds and compositions useful for preventing and/or treating a disease, disorder, or condition, e.g., a disease, disorder, or condition relating to aberrant function of a sodium ion channel, e.g., abnormal late sodium current (INaL). In one aspect, the present disclosure features compounds of Formula (I):

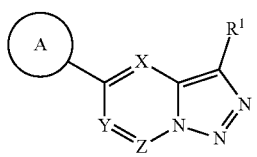

(I)

or a pharmaceutically acceptable salt thereof, wherein:
each of X, Y, and Z is independently N or CR';
A is aryl or heteroaryl (e.g., 6-membered aryl or heteroaryl), wherein aryl and heteroaryl are substituted by one or more $R^3$;
R' is hydrogen, alkyl, —$OR^c$, or halogen;
$R^1$ is hydrogen, deuterium, alkyl, carbocyclyl, or heterocyclyl, wherein alkyl, carbocyclyl, and heterocyclyl are optionally substituted with one or more $R^4$;
each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$;
each of $R^4$ and $R^5$ is independently, alkyl, deuterium, carbocyclyl, heterocyclyl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, and heterocyclyl is optionally substituted by one or more $R^7$;
each $R^c$ is independently hydrogen, deuterium, alkyl, carbocyclyl, heterocyclyl, aryl, or heteroaryl, wherein alkyl, carbocyclyl, heterocyclyl, aryl, and heteroaryl is optionally substituted by one or more $R^6$;
each $R^d$ is independently hydrogen or alkyl, wherein each alkyl is optionally substituted by one or more $R^6$;
each $R^6$ is independently alkyl, deuterium, haloalkyl, carbocyclyl, heterocyclyl, halo, cyano, nitro, or —OH;
and each $R^7$ is independently alkyl, halo, or oxo.

In some embodiments, the compounds of formula (I) is a compound of formula (I-a):

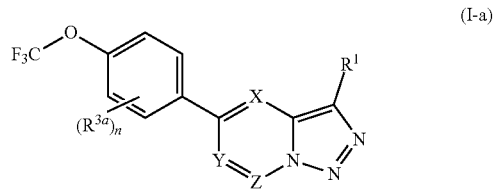

(I-a)

or a pharmaceutically acceptable salt thereof, wherein the variables are as defined herein.

In some embodiments, the compounds of formula (I) is a compound of formula (I-b):

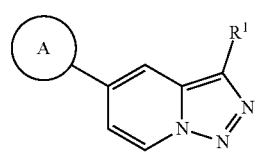

(I-b)

or a pharmaceutically acceptable salt thereof, wherein the variables are as defined herein.

In some embodiments, the compounds of formula (I) is a compound of formula (I-c):

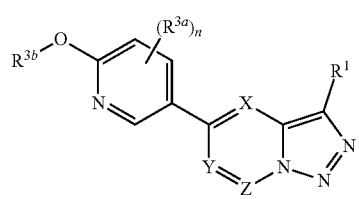

(I-c)

or a pharmaceutically acceptable salt thereof, wherein the variables are as defined herein.

In some embodiments, the compounds of formula (I) is a compound of formula (I-d):

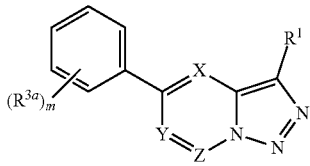

(I-d)

or a pharmaceutically acceptable salt thereof, wherein the variables are as defined herein.

In some embodiments, the compound of Formula (I) is a compound of Formula (I-e):

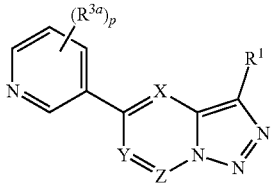

(I-e)

or a pharmaceutically acceptable salt thereof, wherein the variables are as defined herein.

In another aspect, a pharmaceutical composition comprising a compound disclosed herein, or a pharmaceutically acceptable salt thereof, and a pharmaceutically acceptable carrier is provided.

In another aspect, provided herein is a method of treating a neurological disorder or a psychiatric disorder, wherein the method comprises administering to a subject in need thereof a compound disclosed herein (e.g., a compound of formula (I), (I-a), (I-b), (I-c), (I-d), or (I-e)). In some embodiments, the method comprises administering a disclosed pharmaceutical composition.

In another aspect, provided herein is a method of treating a neurological disorder or a psychiatric disorder, wherein the method comprises administering to a subject in need thereof a compound disclosed herein (e.g., a compound of formula (I), (I-a), (I-b), (I-c), (I-d), or (I-e)), or a pharmaceutically acceptable salt thereof or a pharmaceutical composition disclosed herein.

Other objects and advantages will become apparent to those skilled in the art from a consideration of the ensuing Detailed Description, Examples, and Claims.

DETAILED DESCRIPTION OF THE INVENTION

As generally described herein, the present invention provides compounds and compositions useful for preventing and/or treating a disease, disorder, or condition described herein, e.g., a disease, disorder, or condition relating to aberrant function of a sodium ion channel, such as abnormal late sodium current (INaL). Exemplary diseases, disorders, or conditions include a neurological disorder (e.g., epilepsy or an epilepsy syndrome, a neurodevelopmental disorder or a neuromuscular disorder), a psychiatric disorder, pain, or a gastrointestinal disorder.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; F may be in any isotopic form, including $^{18}F$ and $^{19}F$; and the like.

The following terms are intended to have the meanings presented therewith below and are useful in understanding the description and intended scope of the present invention.

When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. "Alkylene," "alkenylene," and "alkynylene," groups may be substituted or unsubstituted with one or more substituents as described herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

As used herein, "heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

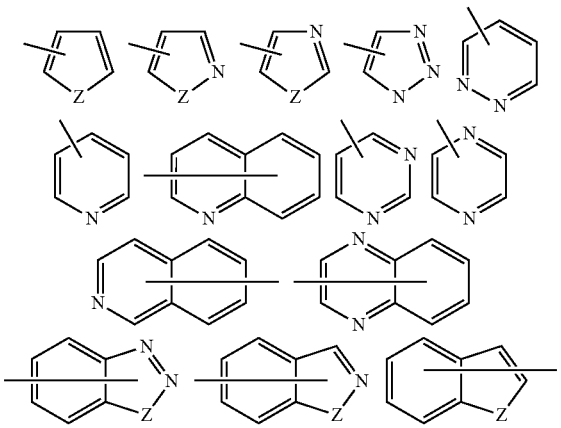

wherein each Z is selected from carbonyl, N, $NR^{65}$, O, and S; and $R^{65}$ is independently hydrogen, $C_1$-$C_8$ alkyl, $C_3$-$C_{10}$ carbocyclyl, 4-10 membered heterocyclyl, $C_6$-$C_{10}$ aryl, and 5-10 membered heteroaryl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or Spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or Spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl; carbocyclyl, e.g., heterocyclyl; aryl, e.g., heteroaryl; and the like having from 1 to 5, and particularly from 1 to 3 heteroatoms.

As used herein, "cyano" refers to —CN.

As used herein, "halo" or "halogen" refers to fluoro (F), chloro (Cl), bromo (Br) and iodo (I). In certain embodiments, the halo group is either fluoro or chloro.

As used herein, "haloalkyl" refers to an alkyl group substituted with one or more halogen atoms.

As used herein, "nitro" refers to —$NO_2$.

As used herein, "oxo" refers to —C=O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O) N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, SO$_2$N(R$^{cc}$)$_2$, —SO$_2$R$^{cc}$, —SO$_2$O R$^{aa}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O) (R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and Claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

Compounds

In one aspect, the present invention features a compound of Formula (I):

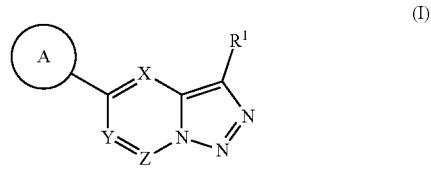

or a pharmaceutically acceptable salt thereof, wherein:
each of X, Y, and Z is independently N or CR';
A is aryl or heteroaryl (e.g., 6-membered aryl or heteroaryl), wherein aryl and heteroaryl are substituted by one or more R$^3$;
R' is hydrogen, alkyl, —OR$^c$, or halogen;
R$^1$ is hydrogen, deuterium, alkyl, carbocyclyl, or heterocyclyl, wherein alkyl, carbocyclyl, and heterocyclyl are optionally substituted with one or more R$^4$;
each R$^3$ is independently alkyl, carbocyclyl, heterocyclyl, halo, cyano, nitro, or —OR$^c$, wherein alkyl, carbocyclyl, and heterocyclyl are optionally substituted with one or more R$^5$;
each of R$^4$ and R$^5$ is independently, alkyl, deuterium, carbocyclyl, heterocyclyl, halo, oxo, cyano, nitro, —OR$^c$, —N(R$^d$)$_2$, —C(O)R$^c$, —C(O)OR$^c$, or —C(O)N(R$^d$)$_2$, wherein alkyl, carbocyclyl, and heterocyclyl is optionally substituted by one or more R$^7$;

each R$^c$ is independently hydrogen, deuterium, alkyl, carbocyclyl, heterocyclyl, aryl, or heteroaryl, wherein alkyl, carbocyclyl, heterocyclyl, aryl, and heteroaryl is optionally substituted by one or more R$^6$;

each R$^d$ is independently hydrogen or alkyl, wherein each alkyl is optionally substituted by one or more R$^6$;

each R$^6$ is independently alkyl, deuterium, haloalkyl, carbocyclyl, heterocyclyl, halo, cyano, nitro, or —OH;

and each R$^7$ is independently alkyl, halo, or oxo.

In some embodiments, X is CR' (e.g., CH). In some embodiments, Y is CR' (e.g., CH). In some embodiments, Z is CR' (e.g., CH). In some embodiments, each of X, Y, and Z is independently CR' (e.g., CH).

In some embodiments, R$^1$ is hydrogen or alkyl. In some embodiments, R$^1$ is hydrogen.

In some embodiments, R$^1$ is alkyl. In some embodiments, R$^1$ is C$_{1-6}$ alkyl (e.g., —CH$_3$). In some embodiments, R$^1$ is C$_{1-6}$ alkyl substituted with 1-4 R$^4$. In some embodiments, R$^1$ is C$_{1-4}$ alkyl substituted with 1-3 R$^4$. In some embodiments, R$^4$ is halo (e.g., fluoro). In some embodiments, R$^1$ is —CF$_3$.

In some embodiments, A is aryl. In some embodiments, A is 6-membered aryl (e.g., phenyl). In some embodiments, A is phenyl substituted by 1-2 R$^3$. In some embodiments, A is phenyl substituted by 2 R$^3$. In some embodiments, R$^3$ is alkyl or —OR$^c$. In some embodiments, R$^3$ is alkyl (—CH$_3$). In some embodiments, R$^3$ is alkyl substituted with R$^5$. In some embodiments, R$^3$ is —CH$_2$OCH$_3$. In some embodiments, R$^3$ is —OR$^c$. In some embodiments, R$^c$ is alkyl. In some embodiments, R$^c$ is alkyl substituted with 1-3 R$^6$. In some embodiments, R$^3$ is —OCF$_3$.

In some embodiments, the compound of Formula (I) is a compound of Formula (I-a):

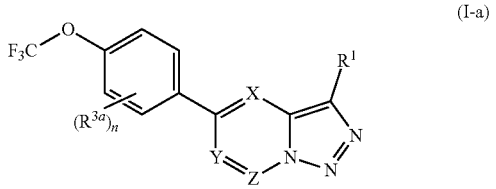

(I-a)

or a pharmaceutically acceptable salt thereof, wherein
each of X, Y, and Z is independently N or CR'; R$^1$ is hydrogen, alkyl, —OR$^c$, or halogen;
R$^1$ is hydrogen, deuterium, alkyl, carbocyclyl, or heterocyclyl, wherein alkyl, carbocyclyl, and heterocyclyl are optionally substituted with one or more R$^4$;
each R$^{3a}$ is independently alkyl, carbocyclyl, heterocyclyl, halo, cyano, nitro, or —OR$^c$, wherein alkyl, carbocyclyl, and heterocyclyl are optionally substituted with one or more R$^5$;
n is 0, 1, or 2;
each of R$^4$ and R$^5$ is independently, alkyl, carbocyclyl, heterocyclyl, halo, oxo, cyano, nitro, —OR$^c$, —N(R$^d$)$_2$, —C(O)R$^c$, —C(O)OR$^c$, or —C(O)N(R$^d$)$_2$, wherein alkyl, carbocyclyl, and heterocyclyl is optionally substituted by one or more R$^7$;
each R$^c$ is independently hydrogen, alkyl, carbocyclyl, heterocyclyl, aryl, or heteroaryl, wherein alkyl, carbocyclyl, heterocyclyl, aryl, and heteroaryl is optionally substituted by one or more R$^6$;
each R$^d$ is independently hydrogen or alkyl, wherein each alkyl is optionally substituted by one or more R$^6$;
each R$^6$ is independently alkyl, carbocyclyl, heterocyclyl, halo, cyano, nitro, or —OH; and each R$^7$ is independently alkyl, halo, or oxo.

In some embodiments, X is CR' (e.g., CH). In some embodiments, Y is CR' (e.g., CH). In some embodiments, Z is CR' (e.g., CH). In some embodiments, each of X, Y, and Z is independently CR' (e.g., CH).

In some embodiments, R$^1$ is hydrogen, deuterium, or alkyl. In some embodiments, R$^1$ is hydrogen or alkyl. In some embodiments, R$^1$ is hydrogen.

In some embodiments, R$^1$ is alkyl. In some embodiments, R' is C$_{1-6}$ alkyl (e.g., —CH$_3$). In some embodiments, R$^1$ is C$_{1-6}$ alkyl substituted with 1-4 R$^4$. In some embodiments, R$^1$ is C$_{1-4}$ alkyl substituted with 1-3 R$^4$. In some embodiments, R$^4$ is halo (e.g., fluoro). In some embodiments, R$^1$ is —CF$_3$.

In some embodiments, n is 1.

In some embodiments, R$^{3a}$ is alkyl. In some embodiments, R$^{3a}$ is alkyl (—CH$_3$). In some embodiments, R$^{3a}$ is alkyl substituted with R$^5$. In some embodiments, R$^{3a}$ is —CH$_2$OCH$_3$.

In some embodiments, the compound of Formula (I) is a compound of Formula (I-b):

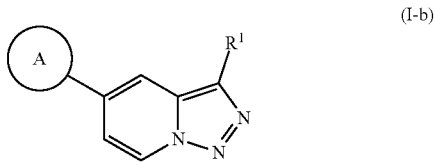

(I-b)

or a pharmaceutically acceptable salt thereof, wherein:
A is aryl or heteroaryl (e.g., 6-membered aryl or heteroaryl), wherein aryl and heteroaryl are substituted by one or more R$^3$;
R$^1$ is hydrogen, deuterium, alkyl, carbocyclyl, or heterocyclyl, wherein alkyl, carbocyclyl, and heterocyclyl are optionally substituted with one or more R$^4$;
each R$^3$ is independently alkyl, carbocyclyl, heterocyclyl, halo, cyano, nitro, or —OR$^c$, wherein alkyl, carbocyclyl, and heterocyclyl are optionally substituted with one or more R$^5$;
each of R$^4$ and R$^5$ is independently, alkyl, deuterium, carbocyclyl, heterocyclyl, halo, oxo, cyano, nitro, —OR$^c$, —N(R$^d$)$_2$, —C(O)R$^c$, —C(O)OR$^c$, or —C(O)N(R$^d$)$_2$, wherein alkyl, carbocyclyl, and heterocyclyl is optionally substituted by one or more R$^7$;
each R$^c$ is independently hydrogen, deuterium, alkyl, aryl, or heteroaryl, wherein alkyl, aryl, and heteroaryl is optionally substituted by one or more R$^6$;
each R$^d$ is independently hydrogen or alkyl, wherein each alkyl is optionally substituted by one or more R$^6$;
each R$^6$ is independently alkyl, deuterium, haloalkyl, carbocyclyl, heterocyclyl, halo, cyano, nitro, or —OH; and each R$^7$ is independently alkyl, halo, or oxo.

In some embodiments, R$^1$ is hydrogen, deuterium, or alkyl. In some embodiments, R$^1$ is hydrogen or alkyl. In some embodiments, R$^1$ is hydrogen.

In some embodiments, $R^1$ is alkyl. In some embodiments, $R^1$ is $C_{1-6}$ alkyl (e.g., —$CH_3$). In some embodiments, $RR^1$ is $C_{1-6}$ alkyl substituted with 1-4 $R^4$. In some embodiments, $R^1$ is $C_{1-4}$ alkyl substituted with 1-3 $R^4$. In some embodiments, $R^4$ is halo (e.g., fluoro). In some embodiments, $RR^1$ is —$CF_3$.

In some embodiments, A is aryl. In some embodiments, A is 6-membered aryl (e.g., phenyl). In some embodiments, A is phenyl substituted by 1-2 $R^3$. In some embodiments, A is phenyl substituted by 2 $R^3$. In some embodiments, $R^3$ is alkyl or —$OR^c$. In some embodiments, $R^3$ is alkyl (—$CH_3$). In some embodiments, $R^3$ is alkyl substituted with $R^5$. In some embodiments, $R^3$ is —$CH_2OCH_3$. In some embodiments, $R^3$ is —$OR^c$. In some embodiments, $R^c$ is alkyl. In some embodiments, le is alkyl substituted with 1-3 $R^6$. In some embodiments, $R^3$ is —$OCF_3$.

In some embodiments, the compound of Formula (I) is a compound of Formula (I-c):

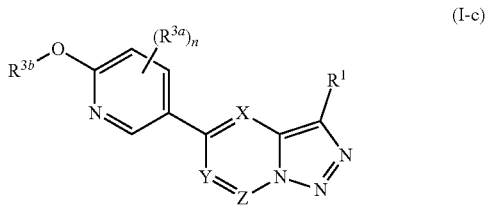

(I-c)

or a pharmaceutically acceptable salt thereof, wherein:
each of X, Y, and Z is independently N or CR';
R' is hydrogen, alkyl, —$OR^c$, or halogen;
$R^1$ is hydrogen, deuterium, alkyl, carbocyclyl, or heterocyclyl, wherein alkyl, carbocyclyl, and heterocyclyl are optionally substituted with one or more $R^4$;
each $R^{3a}$ is independently alkyl, carbocyclyl, heterocyclyl, halo, cyano, nitro, or —$OR^c$, wherein alkyl, carbocyclyl, and heterocyclyl are optionally substituted with one or more $R^5$;
n is 0, 1, or 2;
$R^{3b}$ is alkyl, carbocyclyl, or heterocyclyl, wherein alkyl, carbocyclyl, and heterocyclyl are optionally substituted with one or more $R^5$;
each of $R^4$ and $R^5$ is independently, alkyl, deuterium, carbocyclyl, heterocyclyl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, and heterocyclyl is optionally substituted by one or more $R^7$;
each $R^c$ is independently hydrogen, deuterium, alkyl, carbocyclyl, heterocyclyl, aryl, or heteroaryl, wherein alkyl, carbocyclyl, heterocyclyl, aryl, and heteroaryl is optionally substituted by one or more $R^6$;
each $R^d$ is independently hydrogen or alkyl, wherein each alkyl is optionally substituted by one or more $R^6$;
each $R^6$ is independently alkyl, deuterium, carbocyclyl, heterocyclyl, halo, cyano, nitro, or —OH; and each $R^7$ is independently alkyl, halo, or oxo.

In some embodiments, the compound of Formula (I) is a compound of Formula (I-d):

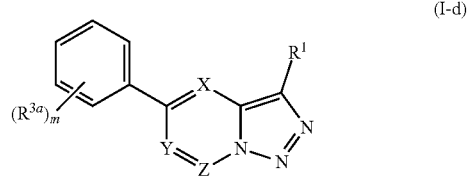

(I-d)

or a pharmaceutically acceptable salt thereof, wherein:
each of X, Y, and Z is independently N or CR';
R' is hydrogen, alkyl, —$OR^c$, or halogen;
$R^1$ is hydrogen, deuterium, alkyl, carbocyclyl, or heterocyclyl, wherein alkyl, carbocyclyl, and heterocyclyl are optionally substituted with one or more $R^4$;
each $R^{3a}$ is independently alkyl, carbocyclyl, heterocyclyl, halo, cyano, nitro, or —$OR^c$, wherein alkyl, carbocyclyl, and heterocyclyl are optionally substituted with one or more $R^5$;
m is 1, 2, or 3;
each of $R^4$ and $R^5$ is independently, alkyl, carbocyclyl, heterocyclyl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, and heterocyclyl is optionally substituted by one or more $R^7$;
each $R^c$ is independently hydrogen, deuterium, alkyl, carbocyclyl, heterocyclyl, aryl, or heteroaryl, wherein alkyl, carbocyclyl, heterocyclyl, aryl, and heteroaryl is optionally substituted by one or more $R^6$;
each $R^d$ is independently hydrogen or alkyl, wherein each alkyl is optionally substituted by one or more $R^6$;
each $R^6$ is independently alkyl, carbocyclyl, heterocyclyl, halo, cyano, nitro, or —OH;
and each $R^7$ is independently alkyl, halo, or oxo.

In some embodiments, the compound of Formula (I) is a compound of Formula (I-e):

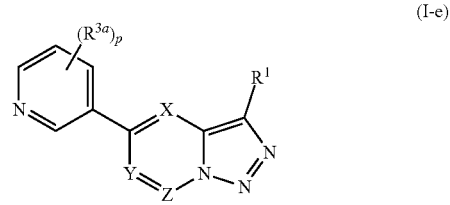

(I-e)

or a pharmaceutically acceptable salt thereof, wherein:
each of X, Y, and Z is independently N or CR';
R' is hydrogen, alkyl, —$OR^c$, or halogen;
$R^1$ is hydrogen, deuterium, alkyl, carbocyclyl, or heterocyclyl, wherein alkyl, carbocyclyl, and heterocyclyl are optionally substituted with one or more $R^4$;
each $R^{3a}$ is independently alkyl, carbocyclyl, heterocyclyl, halo, cyano, nitro, or —$OR^c$, wherein alkyl, carbocyclyl, and heterocyclyl are optionally substituted with one or more $R^5$;
p is 0, 1, 2, or 3;
each of $R^4$ and $R^5$ is independently, alkyl, deuterium, carbocyclyl, heterocyclyl, halo, oxo, cyano, nitro, —$OR^c$, —$N(R^d)_2$, —$C(O)R^c$, —$C(O)OR^c$, or —C(O)N(R$^d$)$_2$, wherein alkyl, carbocyclyl, and heterocyclyl is optionally substituted by one or more R$^7$;

each R$^c$ is independently hydrogen, deuterium, alkyl, carbocyclyl, heterocyclyl, aryl, or heteroaryl, wherein alkyl, carbocyclyl, heterocyclyl, aryl, and heteroaryl is optionally substituted by one or more R$^6$;

each R$^d$ is independently hydrogen or alkyl, wherein each alkyl is optionally substituted by one or more R$^6$;

each R$^6$ is independently alkyl, deuterium, carbocyclyl, heterocyclyl, halo, cyano, nitro, or —OH; and each R$^7$ is independently alkyl, halo, or oxo.

In some embodiments of formula (I-c), (I-d), or (I-e), X, Y, and Z are CR'.

In some embodiments of formula (I-c), (I-d), or (I-e), X is N, Y and Z are CR'.

In some embodiments of formula (I-c), (I-d), or (I-e), Y is N, X and Z are CR'.

In some embodiments of formula (T-c), (l-d), or (I-e), Z is N, X and Y are CR'.

In some embodiments of formula (I-c), (I-d), or (I-e), R' is hydrogen.

In some embodiments of formula (I-c), (I-d), or (I-e), R' is methyl.

In some embodiments of formula (I-c), (I-d), or (I-e), R$^1$ is hydrogen, deuterium, or alkyl, wherein the alkyl is optionally substituted with one or more (e.g., 1, 2, or 3) R$^4$.

In some embodiments of formula (I-c), (I-d), or (I-e), R$^1$ is hydrogen or alkyl, wherein the alkyl is optionally substituted with one or more (e.g., 1, 2, or 3) R$^4$.

In some embodiments of formula (I-c), (I-d), or (I-e), each R$^{3a}$ is independently, alkyl, carbocyclyl, halo, or —OR$^c$, wherein the alkyl and carbocyclyl are optionally substituted with one or more R$^5$.

In some embodiments of formula (I-c), (I-d), or (I-e), n is 0 or 1.

In some embodiments of formula (I-c), (I-d), or (I-e), m is 1 or 2.

In some embodiments of formula (I-c), (I-d), or (I-e), R$^{ab}$ is alkyl or carbocyclyl, wherein alkyl and carbocyclyl are optionally substituted with one or more R$^5$.

In some embodiments of formula (I-c), (I-d), or (I-e), each of R$^4$ is independently halo or —OR$^c$.

In some embodiments of formula (I-c), (I-d), or (I-e), each of R$^5$ is independently, alkyl, halo, cyano, or —OR$^c$, wherein alkyl is optionally substituted by one or more R$^7$.

In some embodiments of formula (I-c), (I-d), or (I-e), each R$^c$ is independently alkyl, wherein alkyl is optionally substituted by one or more R$^6$.

In some embodiments of formula (I-c), (I-d), or (I-e), each R$^6$ is independently halo.

In some embodiments of formula (I-c), (I-d), or (I-e), each R$^7$ is independently halo.

In any and all aspects, in some embodiments, the compound of Formulas (I), (I-a), (I-b), (I-c), (I-d), or (I-e) is selected from the group consisting of:

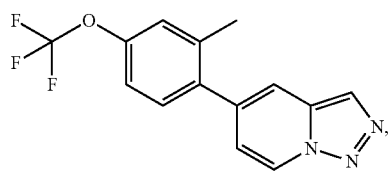

-continued

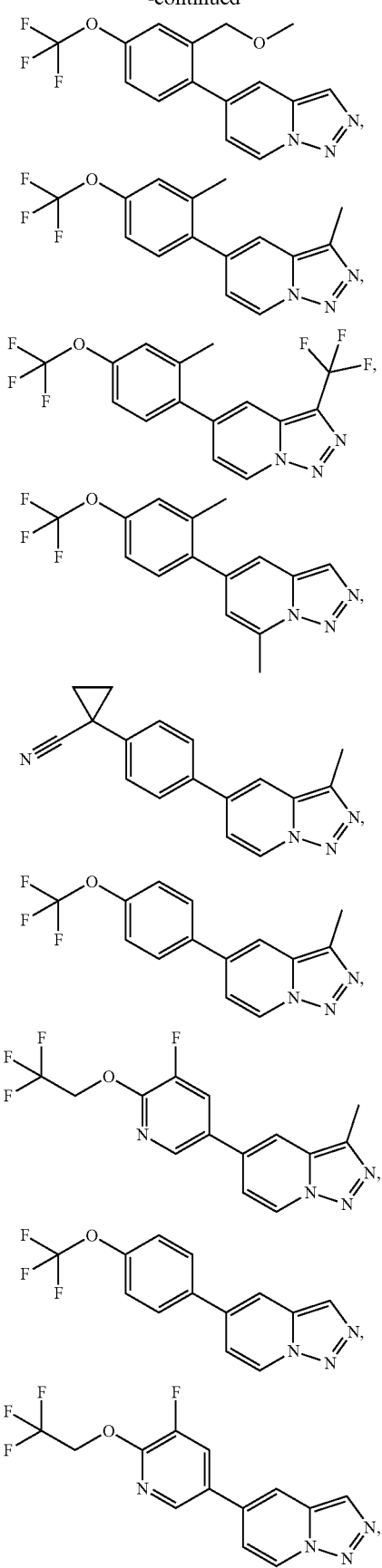

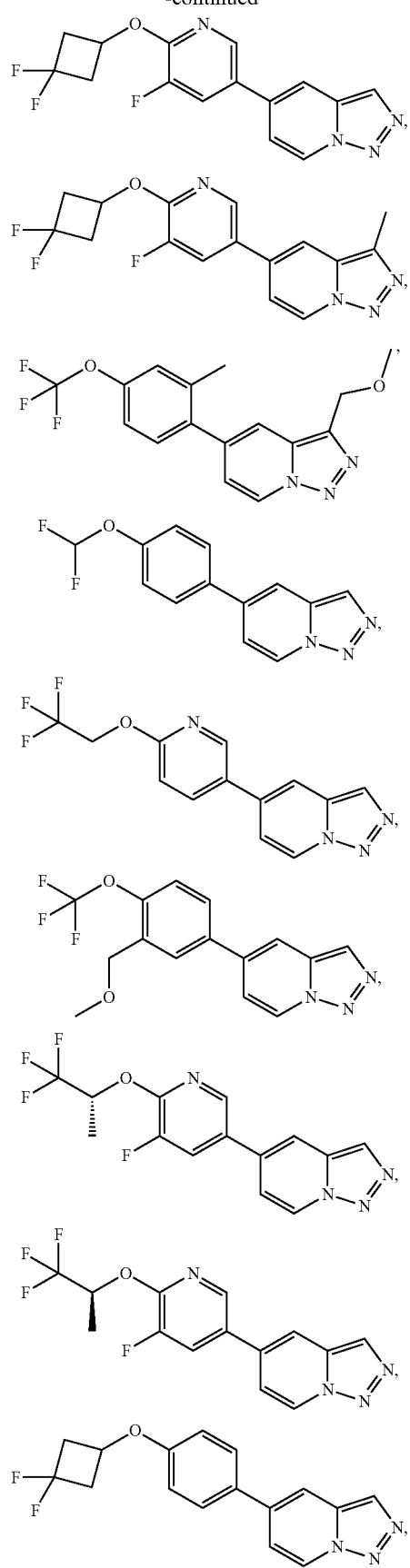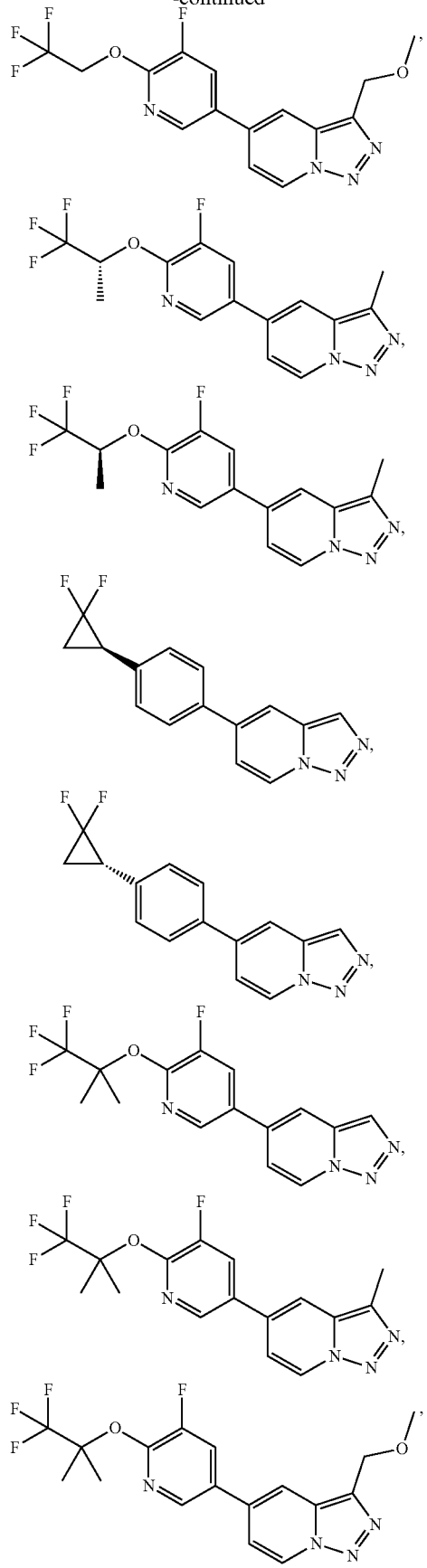

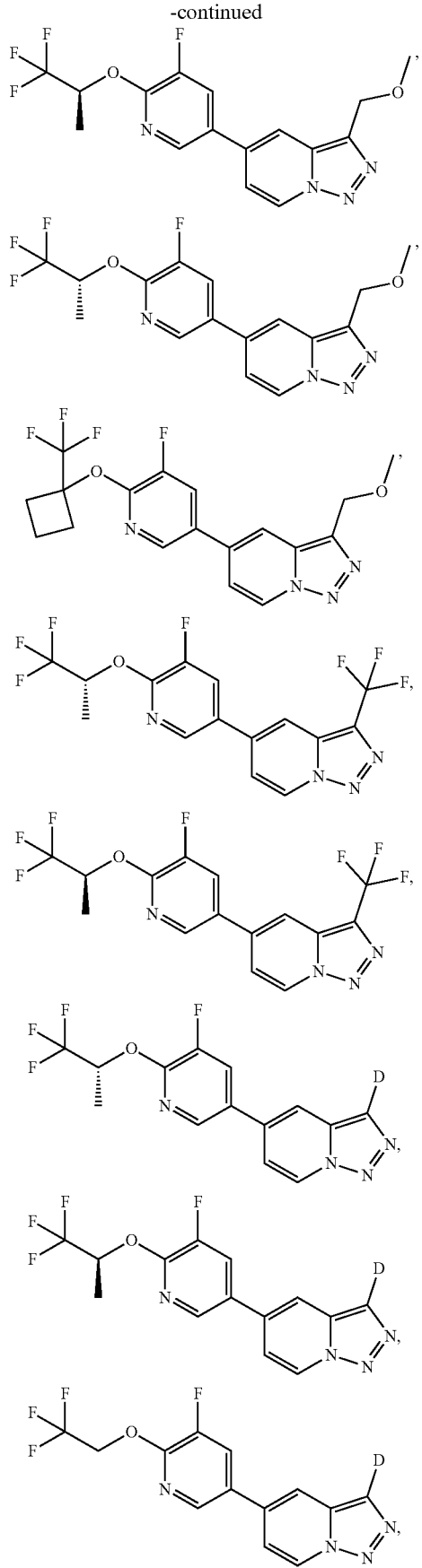
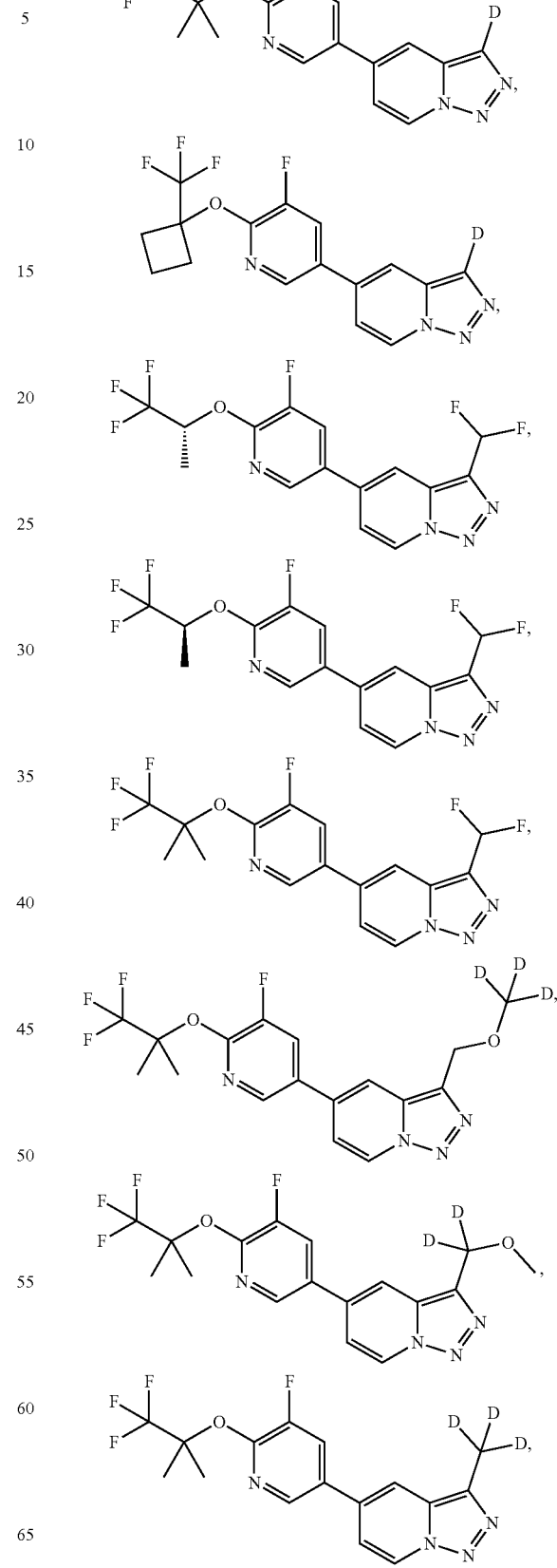

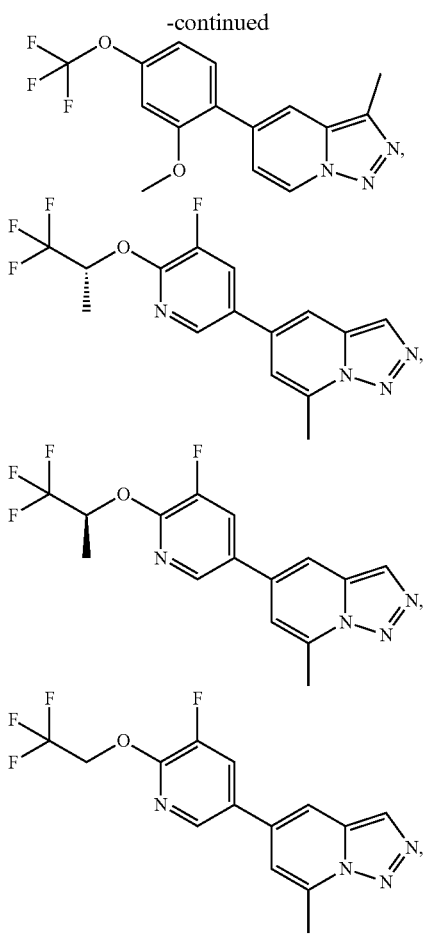

or a pharmaceutically acceptable salt thereof.

Methods of Treatment

Described herein are compounds and compositions thereof and their use to treat a disease, disorder, or condition relating to aberrant function of a sodium channel ion channel, e.g., abnormal late sodium (INaL) current. In some embodiments, a compound provided by the present invention is effective in the treatment of epilepsy or an epilepsy syndrome, a neurodevelopmental disorder, pain, or a neuromuscular disorder. Compounds of the invention may also modulate all sodium ion channels or may be specific to only one or a plurality of sodium ion channels, e.g., Nav 1.1, 1.2, 1.3, 1.4, 1.5, 1.6, 1.7, 1.8, and/or 1.9.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a solvate (e.g., hydrate) of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formula (I), (I-a), (I-b), (I-c), (I-d), or (I-e); such as a compound of Formula named herein.

Epilepsy and Epilepsy Syndromes

The compounds described herein are useful in the treatment of epilepsy and epilepsy syndromes. Epilepsy is a CNS disorder in which nerve cell activity in the brain becomes disrupted, causing seizures or periods of unusual behavior, sensations and sometimes loss of consciousness. Seizure symptoms will vary widely, from a simple blank stare for a few seconds to repeated twitching of their arms or legs during a seizure.

Epilepsy may involve a generalized seizure or a partial or focal seizure. All areas of the brain are involved in a generalized seizure. A person experiencing a generalized seizure may cry out or make some sound, stiffen for several seconds to a minute a then have rhythmic movements of the arms and legs. The eyes are generally open, the person may appear not to be breathing and may actually turn blue. The return to consciousness is gradual and the person may be confused from minutes to hours. There are six main types of generalized seizures: tonic-clonic, tonic, clonic, myoclonic, absence, and atonic seizures. In a partial or focal seizure, only part of the brain is involved, so only part of the body is affected. Depending on the part of the brain having abnormal electrical activity, symptoms may vary.

Epilepsy, as described herein, includes a generalized, partial, complex partial, tonic clonic, clonic, tonic, refractory seizures, status epilepticus, absence seizures, febrile seizures, or temporal lobe epilepsy.

The compounds described herein may also be useful in the treatment of epilepsy syndromes. Severe syndromes with diffuse brain dysfunction caused, at least partly, by some aspect of epilepsy, are also referred to as epileptic encephalopathies. These are associated with frequent seizures that are resistant to treatment and severe cognitive dysfunction, for instance West syndrome.

In some embodiments, the epilepsy syndrome comprises an epileptic encephalopathy, such as Dravet syndrome, Angelman syndrome, CDKL5 disorder, frontal lobe epilepsy, infantile spasms, West's syndrome, Juvenile Myoclonic Epilepsy, Landau-Kleffner syndrome, Lennox-Gastaut syndrome, Ohtahara syndrome, PCDH19 epilepsy, or Glut1 deficiency.

In some embodiments, the epilepsy or epilepsy syndrome is a genetic epilepsy or a genetic epilepsy syndrome. In some embodiments, epilepsy or an epilepsy syndrome comprises epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy.

In some embodiments, the methods described herein further comprise identifying a subject having epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden unexpected death in epilepsy (SUDEP), KCNQ2 epileptic encephalopathy, or KCNT1 epileptic encephalopathy) prior to administration of a compound described herein (e.g., a compound of Formula (I), (I-a), (I-b), (I-c), (I-d), or (I-e)).

In one aspect, the present invention features a method of treating epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy) comprising administering to a subject in need thereof a compound of Formula (I):

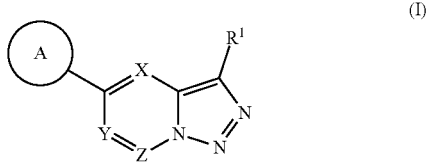

(I)

or a pharmaceutically acceptable salt thereof, wherein:
each of X, Y, and Z is independently N or CR';
A is aryl or heteroaryl (e.g., 6-membered aryl or heteroaryl), wherein aryl and heteroaryl are substituted by one or more $R^3$;
R' is hydrogen, alkyl, —$OR^c$ or halogen;
$R^1$ is hydrogen, deuterium, alkyl, carbocyclyl, or heterocyclyl, wherein alkyl, carbocyclyl, and heterocyclyl are optionally substituted with one or more $R^4$;
each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$;
each of $R^4$ and $R^5$ is independently, alkyl, deuterium, carbocyclyl, heterocyclyl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, and heterocyclyl is optionally substituted by one or more $R^7$;
each $R^c$ is independently hydrogen, deuterium, alkyl, carbocyclyl, heterocyclyl, aryl, or heteroaryl, wherein alkyl, carbocyclyl, heterocyclyl, aryl, and heteroaryl is optionally substituted by one or more $R^6$;
each $R^d$ is independently hydrogen or alkyl, wherein each alkyl is optionally substituted by one or more $R^6$;
each $R^6$ is independently alkyl, deuterium, haloalkyl, carbocyclyl, heterocyclyl, halo, cyano, nitro, or —OH;
and each $R^7$ is independently alkyl, halo, or oxo.

A compound of the present invention (e.g., a compound of Formula (I)) may also be used to treat an epileptic encephalopathy, wherein the subject has a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX.

In some embodiments, the methods described herein further comprise identifying a subject having a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX prior to administration of a compound described herein (e.g., a compound of Formula (I), (I-a), (I-b), (I-c), (I-d), or (I-e)).

Neurodevelopmental Disorders

The compounds described herein may be useful in the treatment of a neurodevelopmental disorder. In some embodiments, the neurodevelopmental disorder comprises autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy. In some embodiments, the methods described herein further comprise identifying a subject having a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) prior to administration of a compound described herein (e.g., a compound of Formula (I), (I-a), (I-b), (I-c), (I-d), or (I-e)).

In one aspect, the present invention features a method of treating a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) comprising administering to a subject in need thereof a compound of Formula (I):

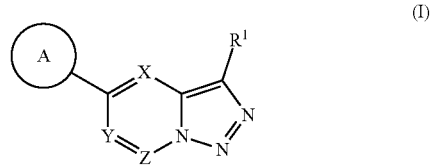

(I)

or a pharmaceutically acceptable salt thereof, wherein:
- each of X, Y, and Z is independently N or CR';
- A is aryl or heteroaryl (e.g., 6-membered aryl or heteroaryl), wherein aryl and heteroaryl are substituted by one or more $R^3$;
- R' is hydrogen, alkyl, —$OR^c$ or halogen;
- $R^1$ is hydrogen, deuterium, alkyl, carbocyclyl, or heterocyclyl, wherein alkyl, carbocyclyl, and heterocyclyl are optionally substituted with one or more $R^4$;
- each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$;
- each of $R^4$ and $R^5$ is independently, alkyl, deuterium, carbocyclyl, heterocyclyl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, and heterocyclyl is optionally substituted by one or more $R^7$;
- each $R^c$ is independently hydrogen, deuterium, alkyl, carbocyclyl, heterocyclyl, aryl, or heteroaryl, wherein alkyl, carbocyclyl, heterocyclyl, aryl, and heteroaryl is optionally substituted by one or more $R^6$;
- each $R^d$ is independently hydrogen or alkyl, wherein each alkyl is optionally substituted by one or more $R^6$;
- each $R^6$ is independently alkyl, deuterium, haloalkyl, carbocyclyl, heterocyclyl, halo, cyano, nitro, or —OH;
- and each $R^7$ is independently alkyl, halo, or oxo.

Pain

The compounds described herein may be useful in the treatment of pain. In some embodiments, the pain comprises neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder. In some embodiments, the methods described herein further comprise identifying a subject having pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) prior to administration of a compound described herein (e.g., a compound of Formula (I), (I-a), (I-b), (I-c), (I-d), or (I-e)).

In one aspect, the present invention features a method of treating pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) comprising administering to a subject in need thereof a compound of Formula (I):

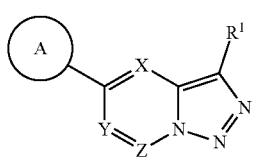

(I)

or a pharmaceutically acceptable salt thereof, wherein:
- each of X, Y, and Z is independently N or CR';
- A is aryl or heteroaryl (e.g., 6-membered aryl or heteroaryl), wherein aryl and heteroaryl are substituted by one or more $R^3$;
- R' is hydrogen, alkyl, —$OR^c$ or halogen;
- $R^1$ is hydrogen, deuterium, alkyl, carbocyclyl, or heterocyclyl, wherein alkyl, carbocyclyl, and heterocyclyl are optionally substituted with one or more $R^4$;
- each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$;
- each of $R^4$ and $R^5$ is independently, alkyl, deuterium, carbocyclyl, heterocyclyl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, and heterocyclyl is optionally substituted by one or more $R^7$;
- each $R^c$ is independently hydrogen, deuterium, alkyl, carbocyclyl, heterocyclyl, aryl, or heteroaryl, wherein alkyl, carbocyclyl, heterocyclyl, aryl, and heteroaryl is optionally substituted by one or more $R^6$;
- each $R^d$ is independently hydrogen or alkyl, wherein each alkyl is optionally substituted by one or more $R^6$;
- each $R^6$ is independently alkyl, deuterium, haloalkyl, carbocyclyl, heterocyclyl, halo, cyano, nitro, or —OH;
- and each $R^7$ is independently alkyl, halo, or oxo.

Neuromuscular Disorders

The compounds described herein may be useful in the treatment of a neuromuscular disorder. In some embodiments, the neuromuscular disorder comprises amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation. In some embodiments, the methods described herein further comprise identifying a subject having a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) prior to administration of a compound described herein (e.g., a compound of Formula (I), (I-a), (I-b), (I-c), (I-d), or (I-e)).

In one aspect, the present invention features a method of treating a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) comprising administering to a subject in need thereof a compound of Formula (I):

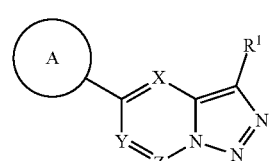

(I)

or a pharmaceutically acceptable salt thereof, wherein:

each of X, Y, and Z is independently N or CR';

A is aryl or heteroaryl (e.g., 6-membered aryl or heteroaryl), wherein aryl and heteroaryl are substituted by one or more $R^3$;

R' is hydrogen, alkyl, —$OR^c$ or halogen;

$R^1$ is hydrogen, deuterium, alkyl, carbocyclyl, or heterocyclyl, wherein alkyl, carbocyclyl, and heterocyclyl are optionally substituted with one or more $R^4$;

each $R^3$ is independently alkyl, carbocyclyl, heterocyclyl, halo, cyano, nitro, or —$OR^c$, wherein alkyl, carbocyclyl, and heterocyclyl are optionally substituted with one or more $R^5$;

each of $R^4$ and $R^5$ is independently, alkyl, deuterium, carbocyclyl, heterocyclyl, halo, oxo, cyano, nitro, —$OR^c$, —$N(R^d)_2$, —$C(O)R^c$, —$C(O)OR^c$, or —$C(O)N(R^d)_2$, wherein alkyl, carbocyclyl, and heterocyclyl is optionally substituted by one or more $R^7$;

each $R^c$ is independently hydrogen, deuterium, alkyl, carbocyclyl, heterocyclyl, aryl, or heteroaryl, wherein alkyl, carbocyclyl, heterocyclyl, aryl, and heteroaryl is optionally substituted by one or more $R^6$;

each $R^d$ is independently hydrogen or alkyl, wherein each alkyl is optionally substituted by one or more $R^6$;

each $R^6$ is independently alkyl, deuterium, haloalkyl, carbocyclyl, heterocyclyl, halo, cyano, nitro, or —OH;

and each $R^7$ is independently alkyl, halo, or oxo.

Other Disorders

In some embodiments, a compound of the present invention (e.g., a compound of Formula (I), (I-a), (I-b), (I-c), (I-d), or (I-e)) may have appropriate pharmacokinetic properties such that they may be active with regard to the central and/or peripheral nervous system. In some embodiments, the compounds provided herein are used to treat a cardiovascular disease such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, and myocardial infarction. In some embodiments, the compounds provided herein may be used in the treatment of diseases affecting the neuromuscular system resulting in itching, seizures, or paralysis, or in the treatment of diabetes or reduced insulin sensitivity, and disease states related to diabetes, such as diabetic peripheral neuropathy.

In some embodiments, a disclosed method comprises administering the pharmaceutical composition.

In some embodiments, provided herein is a method of treating a neurological disorder or a psychiatric disorder, wherein the method comprises administering to a subject in need thereof a compound disclosed herein, or a pharmaceutically acceptable salt thereof or a pharmaceutical composition disclosed herein.

In any and all aspects, in some embodiments, the compound of Formula (I), (I-a), (I-b), (I-c), (I-d), or (I-e) is selected from the group consisting of:

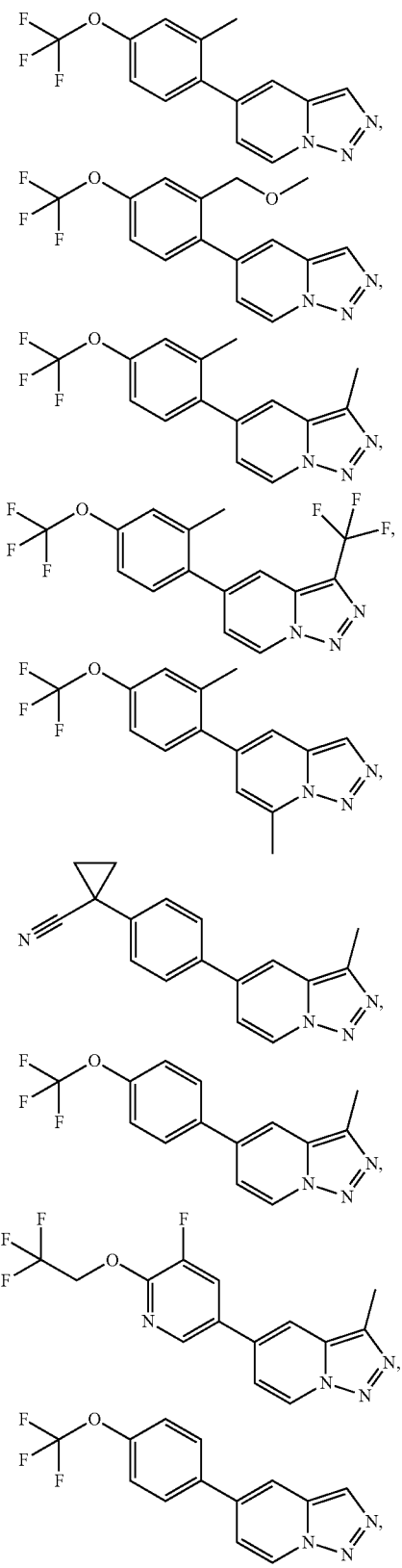

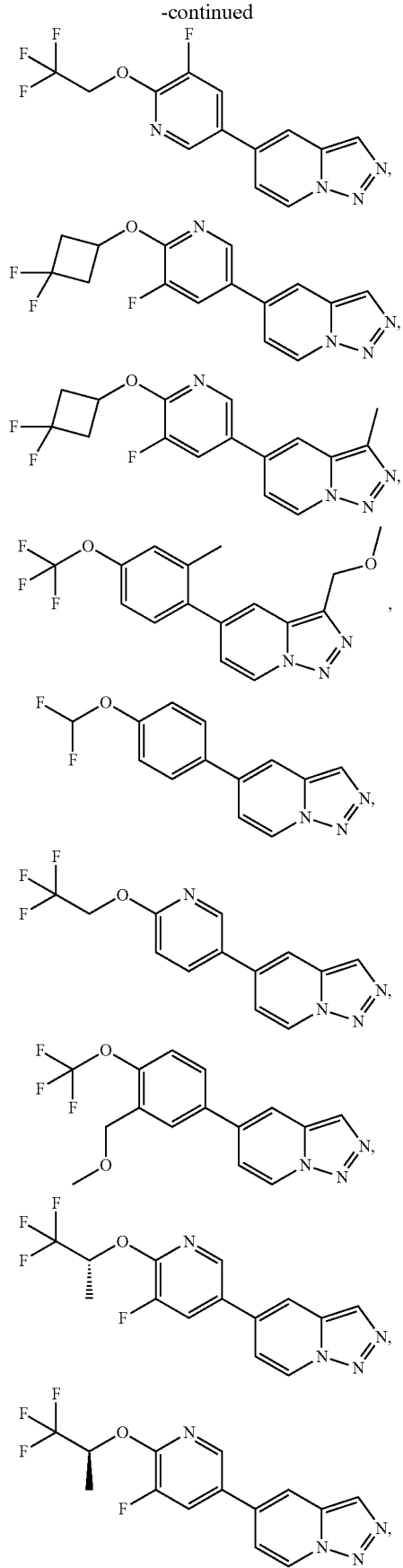

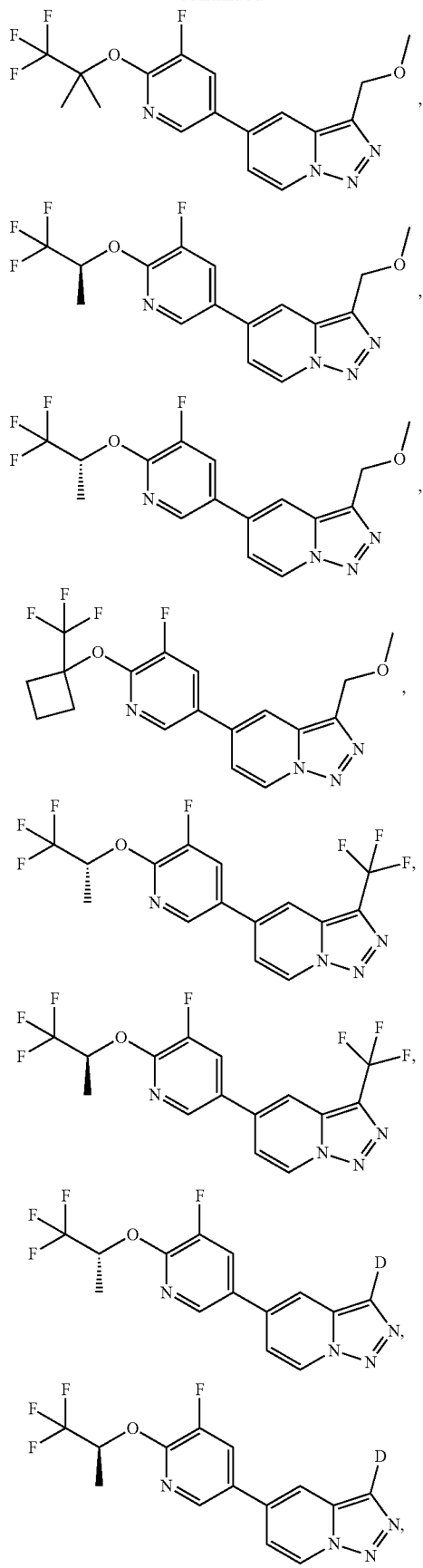
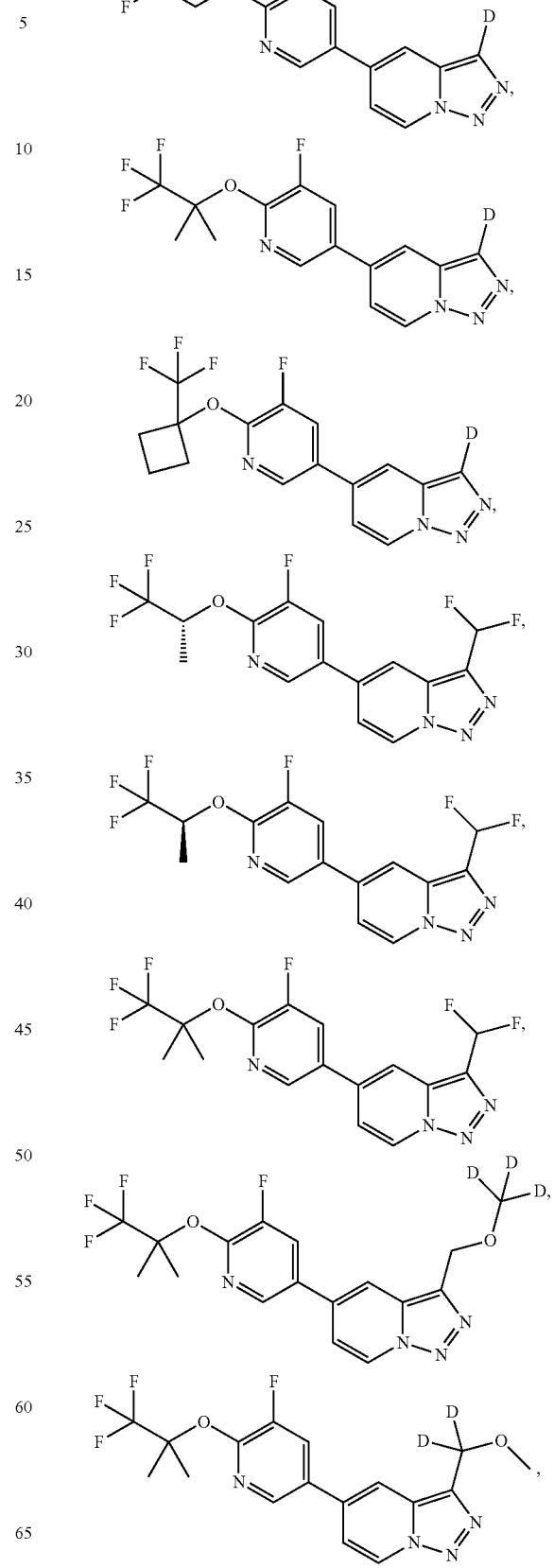

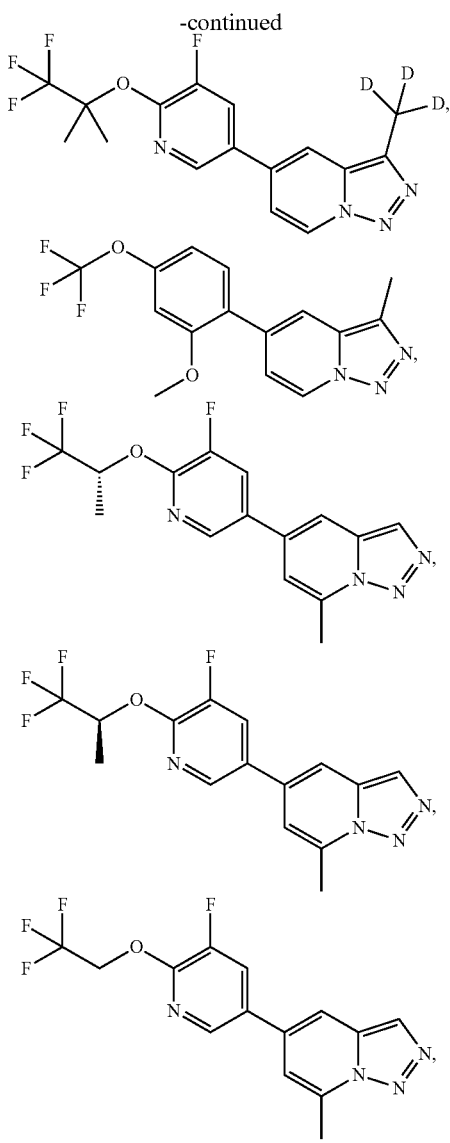

or a pharmaceutically acceptable salt thereof

Pharmaceutical Compositions and Routes of Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, a pharmaceutical composition comprising a disclosed compound, or pharmaceutically acceptable salt thereof, and a pharmaceutically acceptable carrier.

Combination Therapy

A compound or composition described herein (e.g., for use in modulating a sodium ion channel, e.g., the late sodium (INaL) current) may be administered in combination with another agent or therapy. A subject to be administered a compound disclosed herein may have a disease, disorder, or condition, or a symptom thereof, that would benefit from treatment with another agent or therapy. These diseases or conditions can relate to epilepsy or an epilepsy syndrome, a neurodevelopmental disorder, pain, or a neuromuscular disorder.

Antiepilepsy Agents

Anti-epilepsy agents include brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, rufinamide, tigabine, topiramate, valproic acid, vigabatrin, zonisamide, and cannabidiol.

Cardiovascular Agent Combination Therapy

Cardiovascular related diseases or conditions that can benefit from a combination treatment of the sodium channel blockers of the invention with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the sodium channel blockers of the invention with therapeutic agents suitable for treating cardiovascular related conditions allows enhancement in the standard of care therapy the patient is currently receiving.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandatc), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein IIb/IIIa inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest given the recently discovered synergistic effects of the sodium channel blocker ranolazine and amiodarone and dronedarone.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot for illation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-H receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip), ciprofibratc (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient ranolazine in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Antibiotics, Analgesics, Antidepressants and Anti-anxiety Agents Combination Therapy Patients presenting with an acute coronary disease event may exhibit conditions that benefit from administration of therapeutic agent or agents that are antibiotics, analgesics, antidepressant and anti-anxiety agents in combination with ranolazine.

Antibiotics

Antibiotics are therapeutic agents that kill, or stop the growth of, microorganisms, including both bacteria and fungi. Example of antibiotic agents include .beta.-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the sodium channel blockers of the invention to treat neuropathic pain via inhibition of the Nav 1.7 and 1.8 sodium channels, combination with analgesics are particularly envisioned. See U.S. Patent Application Publication 20090203707.

Antidepressant and Anti-Anxiety Agents

Antidepressant and anti-anxiety agents include those agents used to treat anxiety disorders, depression, and those used as sedatives and tranquillizers. Examples of antidepressant and anti-anxiety agents include benzodiazepines, such as diazepam, lorazepam, and midazolam; benzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

Accordingly, one aspect of the invention provides for a composition comprising the sodium channel blockers of the invention and at least one therapeutic agent. In an alternative embodiment, the composition comprises the sodium channel blockers of the invention and at least two therapeutic agents. In further alternative embodiments, the composition comprises the sodium channel blockers of the invention and at least three therapeutic agents, the sodium channel blockers of the invention and at least four therapeutic agents, or the sodium channel blockers of the invention and at least five therapeutic agents.

The methods of combination therapy include co-administration of a single formulation containing the sodium channel blockers of the invention and therapeutic agent or agents, essentially contemporaneous administration of more than one formulation comprising the sodium channel blocker of the invention and therapeutic agent or agents, and consecutive administration of a sodium channel blocker of the invention and therapeutic agent or agents, in any order, wherein preferably there is a time period where the sodium channel blocker of the invention and therapeutic agent or agents simultaneously exert their therapeutic effect.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

Exemplary general methods for analytical LCMS include Method A (Xtimate $C_{18}$ (2.1 mm×30 mm, 3 μm); A=$H_2O$ (0.04% TFA) and B=$CH_3CN$ (0.02% TFA); 50° C.; 1.2 mL/min; 10-80% B over 0.9 minutes, then 80% B for 0.6 minutes) and Method B (Chromolith Flash RP-18 end-capped $C_{18}$ (2 mm×25 mm); A=$H_2O$ (0.04% TFA) and B=$CH_3CN$ (0.02% TFA); 50° C.; 1.5 mL/min; 5-95% B over 0.7 minutes, then 95% B for 0.4 minutes).

List of Abbreviations
Pd(dppf)$Cl_2$ [1,1'-bis(diphenylphosphino)ferrocene]palladium(II) dichloride
TEA triethylamine
MeI methyliodide
NaH sodium hydride
THF tetrahydrofuran
TsNHNH$_2$ p-Toluenesulfonyl hydrazide
Pd(t-Bu$_3$P)$_2$ bis(tri-tert-butylphosphine)palladium(0)
TMSCI trimethylsilyl chloride
DMF N,N-dimethylformamide
n-BuLi n-butyllithium
AgOTf silver trifluoromethanesulfonate
MeOH methanol
DCM dichloromethane
EtOH ethanol
AcN acetonitrile
PPh$_3$ triphenylphosphine
DEAD diethyl azodicarboxylate
TBAF tetrabutylammonium fluoride
TMEDA tetramethylethylenediamine
p-ABSA 4-acetamidobenzenesulfonyl azide
DBU 1,8-diazabicyclo(5.4.0)undec-7-ene
DIBAL-H diisobutylaluminium hydride
DAST diethylaminosulfur trifluoride Example 1. Synthesis of Compound 1

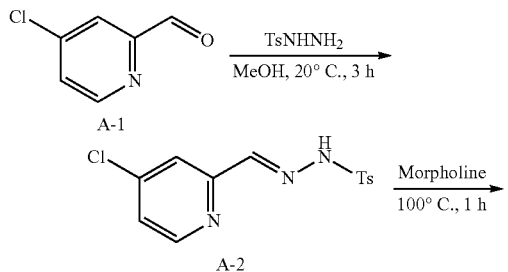

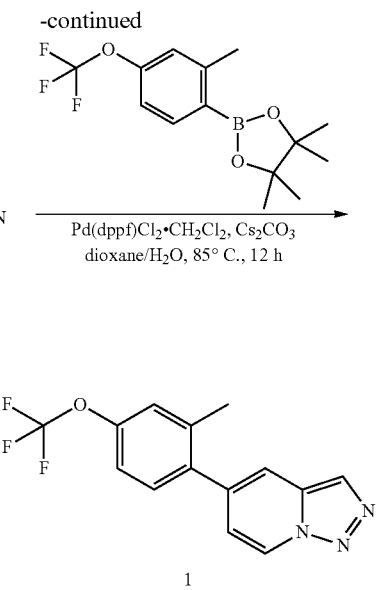

Synthesis of A-2: A mixture of A-1 (1.5 g, 10.6 mmol) and 4-methylbenzenesulfonohydrazide (1.97 g, 10.6 mmol) in methanol (15 mL) was stirred at 20° C. for 3 hours. The solid was collected by filtration, washed with MeOH (3 mL), and dried in oven to afford A-2 (2400 mg, 7.75 mmol) as a solid. $^1$H NMR (400 MHz, DMSO-d$_6$) $δ_H$=11.96 (s, 1H), 8.53 (d, 1H), 7.90 (s, 1H), 7.78 (d, 2H), 7.71 (d, 1H), 7.53 (dd, 1H), 7.43 (d, 2H), 2.37 (s, 3H).

Synthesis of A-3: A mixture of A-2 (2.2 g, 7.1 mmol) in morpholine (12 mL, 137.81 mmol) was stirred at 100° C. for 1 hour. After cooling to room temperature, the mixture was concentrated to a residue that was diluted with $H_2O$ (30 mL) and extracted with EtOAc (100 mL×2). The combined organic phase was washed with water (30 mL×2) and brine (30 mL), dried over $Na_2SO_4$, filtered and concentrated to give the crude product, which was purified by flash chromatography on silica gel (EtOAc in PE=10% to 20% to 30%) to afford A-3 (950 mg, 6.08 mmol) as a solid.

$^1$H NMR (400 MHz, CDCl$_3$) $δ_H$=8.68 (d, 1H), 8.02 (d, 1H), 7.74 (d, 1H), 6.96 (dd, 1H). LCMS $R_t$=0.480 min using Method B, MS ESI calcd. for $C_6H_5ClN_3$ [M+H]$^+$ 154.0, found 153.8.

Synthesis of Compound 1: A mixture of A-3 (70 mg, 0.46 mmol), 4,4,5,5-tetramethyl-2-[2-methyl-4-(trifluoromethoxy)phenyl]-1,3,2-dioxaborolane (206.55 mg, 0.68 mmol), Pd(dppf)$Cl_2$·$CH_2Cl_2$ (55.84 mg, 0.07 mmol) and $Cs_2CO_3$ (297.01 mg, 0.91 mmol) in 1,4-dioxane (5 mL) and water (1 mL) was stirred at 85° C. for 12 hours under $N_2$. After cooling to room temperature, the mixture was concentrated to the residue. The residue was diluted with $H_2O$ (20 mL), and the mixture was extracted with EtOAc (30 mL×2). The combined organic phase was washed with water (20 mL) and brine (20 mL), dried over $Na_2SO_4$, filtered and concentrated to give a crude product that was purified by prep-TLC (silica gel, PE/EtOAc=3/1) to afford Compound 1 (67.45 mg, 0.23 mmol) as a solid. $^1$H NMR (400 MHz, CDCl$_3$) $δ_H$=8.79 (d, 1H), 8.11 (d, 1H), 7.64 (s, 1H), 7.30 (d, 1H), 7.21-7.13 (m, 2H), 6.96 (dd, 1H), 2.34 (s, 3H). LCMS $R_t$=1.180 min using Method A, MS ESI calcd. for $C_{14}H_{11}F_3N_3O$ [M+H]$^+$ 294.1, found 293.9.

Example 2. Synthesis of Compound 2

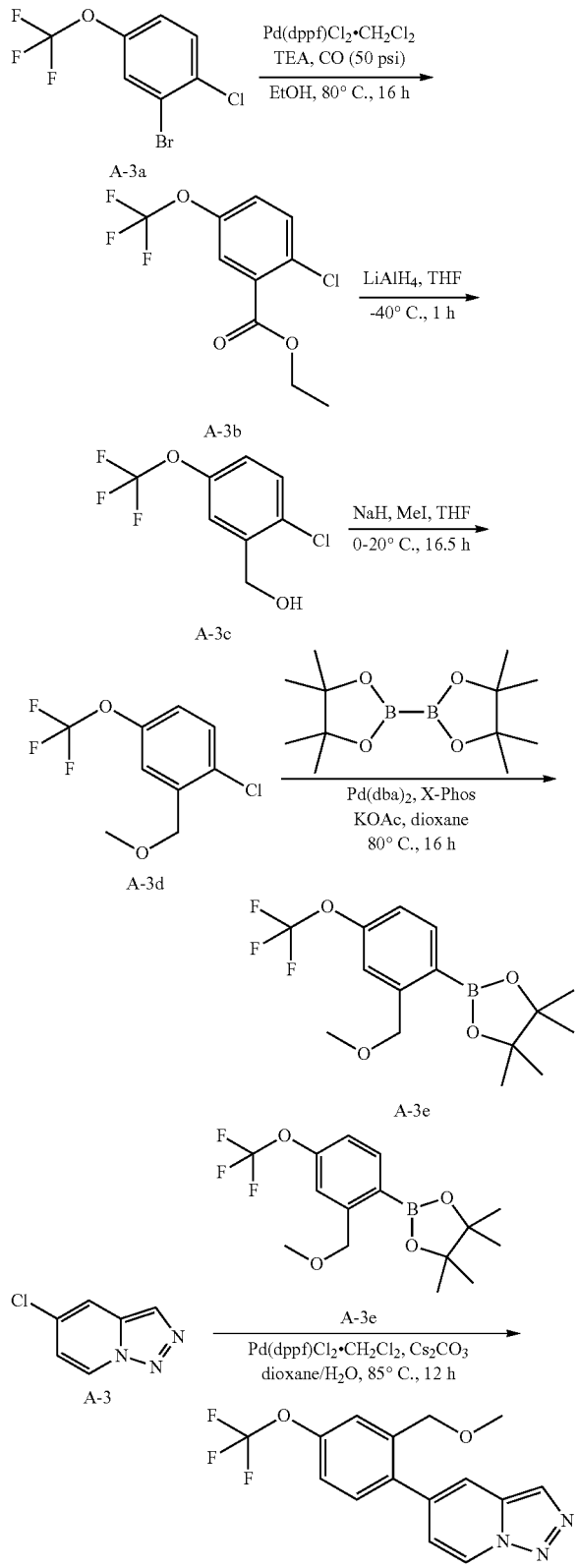

A mixture of 2-bromo-1-chloro-4-(trifluoromethoxy)benzene (5.00 g, 18.15 mmol), Pd(dppf)Cl$_2$·CH$_2$Cl$_2$ (1.48 g, 1.82 mmol) and Et$_3$N (7.55 mL, 54.45 mmol) in EtOH (30.00 mL) was degassed, and refilled with CO. The reaction was stirred under CO (50 psi) for 16 hours at 80° C. The reaction mixture was diluted with EtOH (20 mL), filtered through Celite, concentrated, and purified by flash chromatography on silica gel (EtOAc in PE=0%-5%) to afford A-3b (2.40 g, 8.93 mmol) as an oil. $^1$H NMR (400 MHz, CDCl$_3$) $\delta_H$=7.66-7.59 (m, 1H), 7.42 (d, 1H), 7.24-7.19 (m, 1H), 4.36 (q, 2H), 1.35 (t, 3H).

To a solution of A-3b (2.40 g, 8.93 mmol) in THF (30 mL) at −40° C. was added LiAlH$_4$ (406.67 mg, 10.72 mmol) slowly. The reaction was stirred at −40° C. for 1 hour. The reaction was quenched with sat. NH$_4$Cl (0.4 mL), diluted with EtOAc (30 mL), and the solid formed was filtered through Celite and eluted with EtOAc (30 mL). The filtrate was concentrated and purified by flash chromatography on silica gel (EtOAc in PE=0% to 10% to 20%) to afford A-3c (1.50 g, 6.62 mmol) as a solid. $^1$H NMR (400 MHz, CDCl$_3$) $\delta_H$=7.45-7.42 (m, 1H), 7.38 (d, 1H), 7.13-7.08 (m, 1H), 4.80 (d, 2H), 2.04 (t, 1H).

To a solution of A-3c (1.50 g, 6.62 mmol, 1.00 eq) in THF (20 mL) at 0° C. was added NaH (317.76 mg, 7.94 mmol, 60% purity) slowly. The mixture was stirred at 0° C. for 30 min, then MeI (1.24 mL, 19.86 mmol) was added, and the reaction was stirred at 20° C. for 16 hours. The reaction mixture was quenched with sat. NH$_4$Cl (50 mL), extracted with EtOAc (50 mL×3). The combined organic phase was washed with brine (50 mL), dried over Na$_2$SO$_4$, filtered, and concentrated, and the residue was purified by flash chromatography on silica gel (EtOAc in PE=0% to 5% to 10%) to afford A-3d (1.40 g, 5.82 mmol) as an oil. $^1$H NMR (400 MHz CDCl$_3$) $\delta_H$=7.43-7.32 (m, 2H), 7.09 (dd, 1H), 4.54 (s, 2H), 3.50 (s, 3H).

A mixture of A-3d (400.00 mg, 1.66 mmol), 4,4,5,5-tetramethyl-2-(4,4,5,5-tetramethyl-1,3,2-dioxaborolan-2-yl)-1,3,2-dioxaborolane (505.85 mg, 1.99 mmol), KOAc (325.82 mg, 3.32 mmol), X-Phos (197.84 mg, 415.00 µmol) and Pd$_2$(dba)$_3$ (152.01 mg, 166.00 µmop in dioxane (6 mL) was stirred under N$_2$ at 80° C. for 16 hours. The mixture was cooled to room temperature, concentrated, and the residue was purified by flash chromatography on silica gel (PE: EtOAc=1:0 to 50:1) to afford A-3e (300.00 mg, 903.29 µmol) as an oil. LCMS R$_t$=0.99 min using Method B, MS ESI calcd. for C$_{15}$H$_{21}$BF$_3$O$_4$ [M+H]+ 333.1, found 332.7.

A mixture of A-3 (70 mg, 0.46 mmol), 2-[2-(methoxymethyl)-4-(trifluoromethoxy)phenyl]-4,4,5,5-tetramethyl-1,3,2-dioxaborolane (250 mg, 0.75 mmol), Pd(dppf)Cl$_2$·CH$_2$Cl$_2$ (55.84 mg, 0.07 mmol) and Cs$_2$CO$_3$ (297.01 mg, 0.91 mmol) in 1,4-dioxane (5 mL) and water (1 mL) was stirred at 85° C. for 12 hours under N$_2$. After cooling to room temperature, the mixture was diluted with H$_2$O (20 mL) and extracted with EtOAc (30 mL×2). The combined organic phase was washed with water (20 mL) and brine (20 mL), dried over Na$_2$SO$_4$, filtered and concentrated to give the crude product, which was purified by prep-TLC (silica gel, PE/EtOAc=3/1) to afford Compound 2 (11.25 mg, 0.034 mmol) as a solid. $^1$H NMR (400 MHz, CDCl$_3$) $\delta_H$=8.79 (d, 1H), 8.13 (s, 1H), 7.73 (s, 1H), 7.45 (s, 1H), 7.38 (d, 1H), 7.37-7.27 (m, 1H), 7.05 (dd, 1H), 4.33 (s, 2H), 3.39 (s, 3H). LCMS R$_t$=1.141 min using Method B, MS ESI calcd. for C$_{15}$H$_{13}$F$_3$N$_3$O$_2$ [M+H]$^+$ 324.1, found 323.9.

Example 3. Synthesis of Compound 3

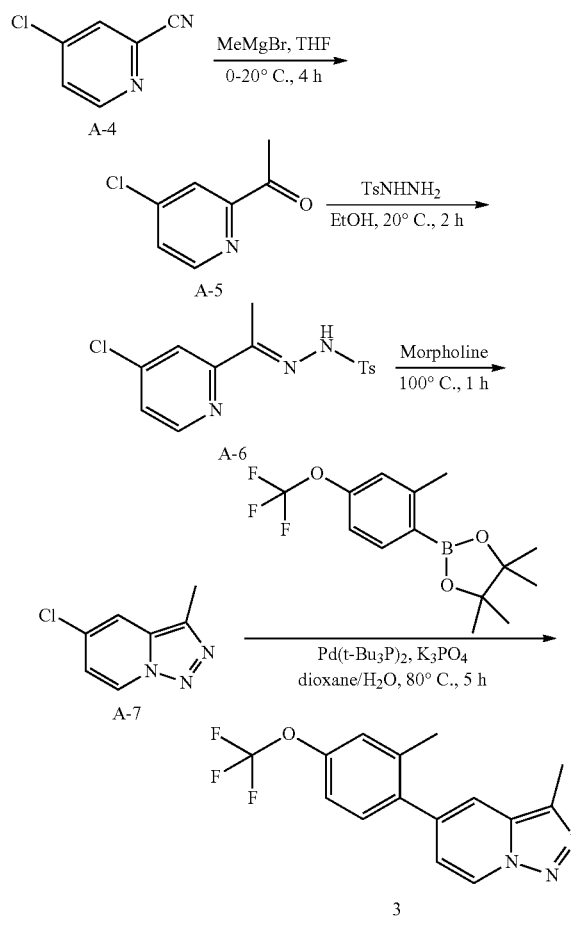

Synthesis of A-5: To a mixture of A-4 (3 g, 21.65 mmol) in THF (60 mL) was added bromo(methyl)magnesium (14.44 mL, 43.31 mmol) at 0° C., then the mixture was stirred at 0° C. for 2 hours. The reaction mixture was added to ice-water (50 mL) and 2 M HCl (25 mL), stirred for 15 minutes, and extracted with EtOAc (50 mL×2). The combined organic phase was washed with water (30 mL) and brine (30 mL), dried over $Na_2SO_4$, filtered and concentrated to give the crude product, which was purified by flash chromatography on silica gel (EtOAc in PE=0% to 10% to 20%) to afford A-5 (660 mg, 3.31 mmol) as a solid. $^1H$ NMR (400 MHz, $CDCl_3$) $\delta_H$=8.59 (d, 1H), 8.04 (d, 1H), 7.48 (dd, 1H), 2.73 (s, 3H). LCMS Rt=0.640 min using Method B, MS ESI calcd. for $C_7H_7ClNO$ $[M+H]^+$ 156.0, found 155.8.

Synthesis of A-6: A mixture A-5 (600 mg, 3.01 mmol) and 4-methylbenzenesulfonohydrazide (840.41 mg, 4.51 mmol) in ethanol (10 mL) was stirred at 20° C. for 2 hours. The solid was collected by filtration, washed with PE (3 mL), and dried to afford A-6 (940 mg, 2.84 mmol) as a solid. $^1H$ NMR (400 MHz, DMSO-$d_6$) $\delta_H$=10.97 (s, 1H), 8.54 (d, 1H), 7.82 (d, 2H), 7.71 (d, 1H), 7.54 (dd, 1H), 7.43 (d, 2H), 2.38 (s, 3H), 2.24 (s, 3H). LCMS Rt=0.807 min using Method A, MS ESI calcd. for $C_{14}H_{15}ClN_3O_2S$ $[M+H]^+$ 324.0, found 323.9.

Synthesis of A-7: A mixture of A-6 (940 mg, 2.9 mmol) in morpholine (10 mL, 114.78 mmol) was stirred at 100° C. for 1 hour. After cooling to room temperature, the mixture was concentrated to a residue that was diluted with $H_2O$ (30 mL) and extracted with EtOAc (50 mL×2). The combined organic phase was washed with water (20 mL) and brine (20 mL), dried over $Na_2SO_4$, filtered and concentrated to give the crude product, which was purified by flash chromatography on silica gel (EtOAc in PE=0% to 25% to 50%) to afford A-7 (440 mg, 2.60 mmol) as a solid. $^1H$ NMR (400 MHz, $CDCl_3$) $\delta_H$=8.58 (d, 1H), 7.62 (d, 1H), 6.89 (dd, 1H), 2.60 (s, 3H). LCMS $R_t$=0.638 min using Method B, MS ESI calcd. for $C_7H_7ClN_3$ $[M+H]^+$ 168.0, found 167.8.

Synthesis of Compound 3: A mixture of A-7 (120 mg, 0.72 mmol), 4,4,5,5-tetramethyl-2-[2-methyl-4-(trifluoromethoxy)phenyl]-1,3,2-dioxaborolane (302.82 mg, 1 mmol), $Pd(t-Bu_3P)_2$ (54.89 mg, 0.11 mmol) and $K_3PO_4$ (304.01 mg, 1.43 mmol) in 1,4-dioxane (5 mL) and water (1 mL) was stirred at 80° C. for 5 hours under $N_2$. After cooling to room temperature, the mixture was diluted with $H_2O$ (20 mL) and extracted with EtOAc (30 mL×2). The combined organic phase was washed with water (20 mL) and brine (20 mL), dried over $Na_2SO_4$, filtered and concentrated to give the crude product, which was purified by prep-TLC (silica gel, PE/EtOAc=2/1) to afford Compound 3 (142.3 mg, 0.463 mmol) as a solid. $^1H$ NMR (400 MHz, $CDCl_3$) $\delta_H$=8.69 (d, 1H), 7.51 (s, 1H), 7.30 (d, 1H), 7.21-7.13 (m, 2H), 6.90 (dd, 1H), 2.65 (s, 3H), 2.34 (s, 3H). LCMS $R_t$=1.231 min using Method A, MS ESI calcd. for $C_{15}H_{13}F_3N_3O$ $[M+H]^+$ 308.1, found 307.9.

Example 4. Synthesis of Compound 4

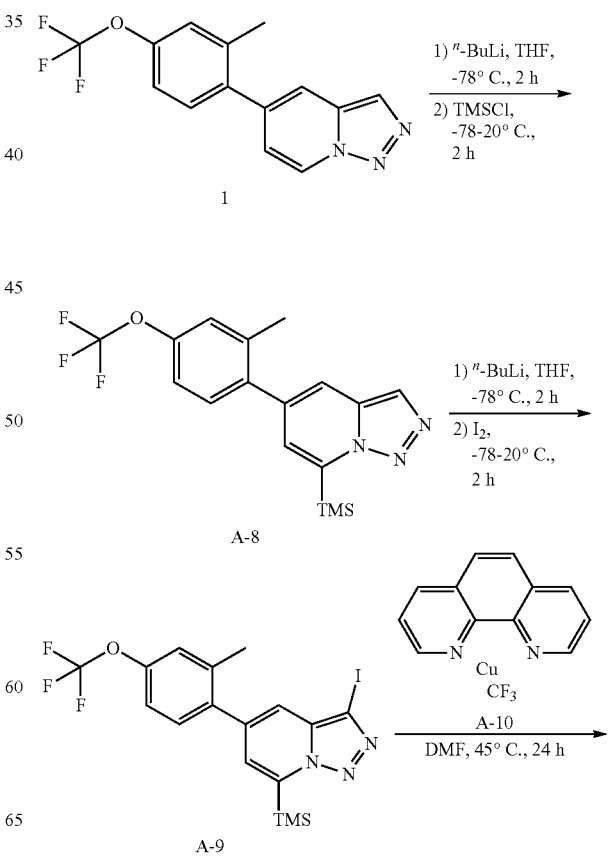

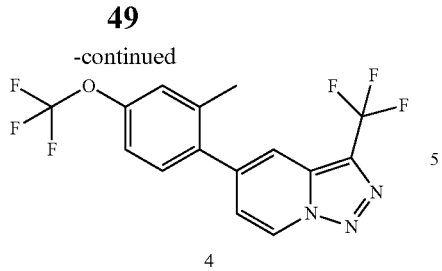

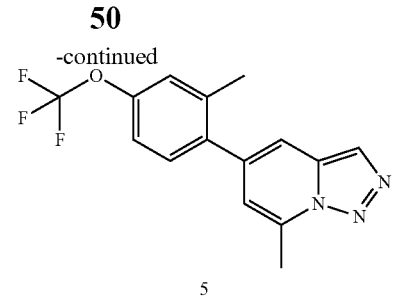

Synthesis of A-8: To a mixture of Compound 1 (500 mg, 1.71 mmol) in THF (10 mL) was added n-BuLi (2.05 mL, 5.12 mmol) at −78° C. under $N_2$, then the mixture was stirred at −78° C. for 2 hours. To the mixture was added chloro(trimethyl)silane (370.48 mg, 3.41 mmol), then the mixture was stirred at −78° C. to 20° C. for 2 hours. The mixture was quenched with sat. $NH_4Cl$ (20 mL) and extracted with EtOAc (30 mL×2). The combined organic phase was washed with brine (20 mL), dried over $Na_2SO_4$, filtered and concentrated to give the crude product, which was purified by flash chromatography on silica gel (EtOAc in PE=0% to 10% to 20%) to afford A-8 (340 mg, 0.85 mmol) as an oil. $^1H$ NMR (400 MHz, $CDCl_3$) $\delta_H$=8.10 (s, 1H), 7.60 (d, 1H), 7.30 (d, 1H), 7.21-7.13 (m, 2H), 6.97 (d, 1H), 2.33 (s, 3H), 0.54 (s, 9H). LCMS Rt=0.985 min using Method B, MS ESI calcd. for $C_{17}H_{19}F_3N_3OSi$ $[M+H]^+$ 366.1, found 366.0.

Synthesis of A-9: To a mixture of A-8 (320 mg, 0.88 mmol) in TT-W (10 mL) was added n-BuLi (1.4 mL, 3.5 mmol) at −78° C. under $N_2$, and then the mixture was stirred at −78° C. for 2 hours. To the mixture was added $I_2$ (444.51 mg, 1.75 mmol), then the mixture was stirred at −78° C. to 20° C. for 2 hours. The mixture was quenched with sat. $NH_4Cl$ (20 mL), and the mixture was extracted with EtOAc (30 mL×2). The combined organic phase was washed with sat. $Na_2S_2O_3$ (20 mL) and brine (30 mL), dried over $Na_2SO_4$, filtered and concentrated to give the crude product, which was purified by flash chromatography on silica gel (EtOAc in PE=0% to 10%) to afford A-9 (230 mg, 0.38 mmol) as an oil. $^1H$ NMR (400 MHz, $CDCl_3$) $\delta_H$=7.47 (d, 1H), 7.31 (d, 1H), 7.21-7.15 (m, 2H), 7.01 (d, 1H), 2.34 (s, 3H), 0.53 (s, 9H).

Synthesis of Compound 4: A mixture of A-9 (150 mg, 0.31 mmol) and A-10 (381.94 mg, 1.22 mmol) in DMF (2 mL) was stirred at 45° C. for 24 hours in 10 mL sealed tube under $N_2$. After cooling to room temperature, the mixture was diluted with $H_2O$ (10 mL) and extracted with EtOAc (20 mL×2). The combined organic phase was washed with water (10 mL×2) and brine (10 mL), dried over $Na_2SO_4$, filtered and concentrated to give the crude product, which was purified by prep-TLC (silica gel, PE/EtOAc=4/1) to afford Compound 4 (21.69 mg, 0.06 mmol) as a solid. $^1H$ NMR (400 MHz, $CDCl_3$) $\delta_H$=8.86 (dd, 1H), 7.77 (s, 1H), 7.32 (d, 1H), 7.24-7.17 (m, 2H), 7.12 (dd, 1H), 2.35 (s, 3H). LCMS $R_t$=1.336 min using Method A, MS ESI calcd. for $C_{15}H_{10}F_6N_3O$ $[M+H]^+$ 362.1, found 362.0.

Example 5. Synthesis of Compound 5

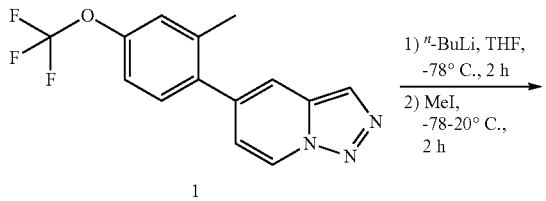

To a mixture of 5-[2-methyl-4-(trifluoromethoxy)phenyl]triazolo[1,5-a]pyridine (100 mg, 0.34 mmol) in THF (4 mL) was added n-BuLi (0.41 mL, 1.02 mmol) at −78° C. under $N_2$, then the mixture was stirred at −78° C. for 2 hours. To the mixture was added iodomethane (145.21 mg, 1.02 mmol), then the mixture was allowed to warm to 20° C. slowly and stirred at for 2 hours. The mixture was quenched with sat. $NH_4Cl$ (10 mL), then the mixture was extracted with EtOAc (20 mL×2). The combined organic phase was washed with brine (10 mL), dried over $Na_2SO_4$, filtered and concentrated to give the crude product. The crude product was purified by Prep-TLC (PE:EtOAc=4:1) to give the product (10.76 mg, 0.035 mmol, 10% yield)) as a solid. $^1H$ NMR (400 MHz, DMSO-$d_6$) δ=8.27 (s, 1H), 7.85 (s, 1H), 7.45 (d, 1H), 7.39 (s, 1H), 7.31 (d, 1H), 7.14 (s, 1H), 2.85 (s, 3H), 2.33 (s, 3H). LCMS $R_t$=1.233 min in 2.0 min chromatography, 10-80AB, purity 100%, MS ESI calcd. for $C_{15}H_{13}F_3N_3O$ $[M+H]^+$ 308.1, found 307.9.

Example 6. Synthesis of Compound 6

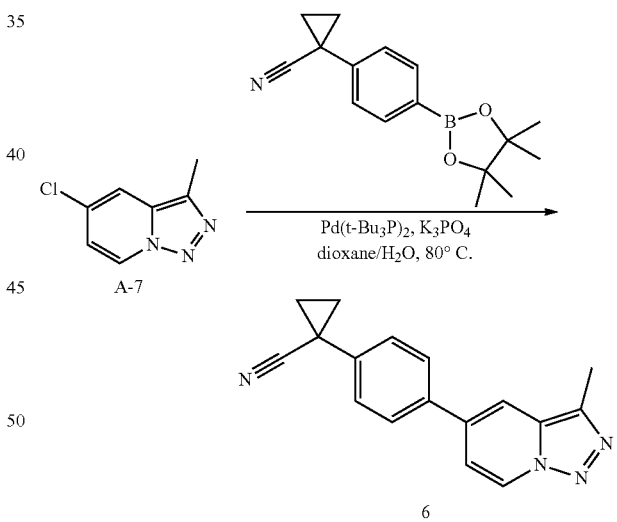

A mixture of 5-chloro-3-methyl-triazolo[1,5-a]pyridine (50 mg, 0.30 mmol), 1-[4-(4,4,5,5-tetramethyl-1,3,2-dioxaborolan-2-yl)phenyl]cyclopropanecarbonitrile (102.1 mg, 0.36 mmol), Pd(t-$Bu_3P$)$_2$ (22.87 mg, 0.04 mmol) and $K_3PO_4$ (126.67 mg, 0.60 mmol) in 1,4-Dioxane (2 mL) and Water (0.2 mL) was stirred at 80° C. for 16 hours to give a brown mixture. After cooling to room temperature, the suspension was diluted with EtOAc (10 mL), filtered through Celite and eluted with EtOAc (20 mL). And the combined filtrates were concentrated to give crude product. The crude product was purified by flash chromatography on silica gel (EtOAc in PE=20% to 70%) to give the product (32.6 mg, 0.11 mmol, 38% yield) as a solid. $^1$H NMR (400 MHZ, DMSO-d$_6$) $\delta_H$=9.02 (d, 1H), 8.25 (s, 1H), 7.90 (d, 2H), 7.51-7.44 (m, 3H), 2.59 (s, 3H), 1.84-1.79 (m, 2H), 1.61-1.56 (m, 2H). LCMS R$_t$=1.02 min in 2.0 min chromatography, 10-80AB, purity 100%, MS ESI calcd. for C$_{17}$H$_{15}$N$_4$ [M+H]$^+$ 275.1, found 274.9.

Example 7. Synthesis of Compound 7

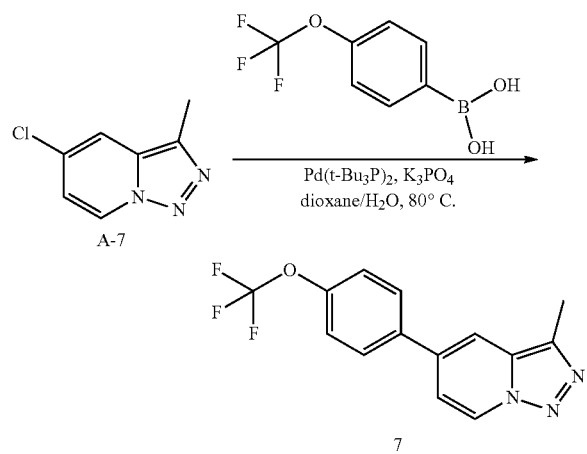

A mixture of 5-chloro-3-methyl-triazolo[1,5-a]pyridine (70 mg, 0.42 mmol), [4-(trifluoromethoxy)phenyl]boronic acid (103.21 mg, 0.50 mmol), Pd(t-Bu$_3$P)$_2$ (32.02 mg, 0.06 mmol) and K$_3$PO$_4$ (177.34 mg, 0.84 mmol) in 1,4-Dioxane (5 mL) and Water (1 mL) was stirred at 80° C. for 5 hours under N$_2$. After cooling to room temperature, the mixture was diluted with H$_2$O (20 mL), and the mixture was extracted with EtOAc (30 mL×2). The combined organic phase was washed with water (20 mL) and brine (20 mL), dried over Na$_2$SO$_4$, filtered and concentrated to give the crude product. The crude product was purified by Prep-TLC (silica gel, PE:EtOAc=3:1) to give the product (28.61 mg, 0.10 mmol, 23% yield) as a solid. NMR (400 MHz, CDCl$_3$) $\delta_H$=8.72 (d, 1H), 7.75 (s, 1H), 7.68 (d, 2H), 7.36 (d, 2H), 7.17 (dd, 1H), 2.68 (s, 3H). LCMS R$_t$=1.17 min in 2.0 min chromatography, 10-80AB, purity 100.00%, MS ESI calcd. for C$_{14}$H$_{11}$F$_3$N$_3$O [M+H]$^+$ 294.1, found 293.9.

Example 8. Synthesis of Compound 8

A mixture of 5-chloro-3-methyl-triazolo[1,5-a]pyridine (50 mg, 0.30 mmol), 3-fluoro-5-(4,4,5,5-tetramethyl-1,3,2-dioxaborolan-2-yl)-2-(2,2,2-trifluoroethoxy)pyridine (114.95 mg, 0.36 mmol), Pd(t-Bu$_3$P)$_2$ (22.87 mg, 0.04 mmol) and K$_3$PO$_4$ (126.67 mg, 0.60 mmol) in Water (0.2 mL) and 1,4-Dioxane (2 mL) was stirred at 80° C. for 16 hours to give a brown mixture. After cooling to room temperature, the suspension was diluted with EtOAc (10 mL), filtered through silica gel, eluted with EtOAc (20 mL). The combined filtrates were concentrated to afford the crude product. The crude product was purified by flash chromatography on silica gel (EtOAc in PE=20% to 70%) to give the impure product. The impure product was then purified by Prep-TLC (silica gel, PE:EtOAc=1:2) to give the product (28.27 mg, 0.09 mmol, 29% yield) as a solid. $^1$H NMR (400 MHz, CDCl$_3$) $\delta_H$=8.74 (d, 1H), 8.24 (d, 1H), 7.75-7.68 (m, 2H), 7.11 (dd, 1H), 4.92 (q, 2H), 2.68 (s, 3H). LCMS R$_t$=1.08 min in 2.0 min chromatography, 10-80AB, purity 100%, MS ESI calcd. for C$_{14}$H$_{11}$F$_4$N$_4$O [M+H]$^+$ 327.1, found 326.9.

Example 9. Synthesis of Compound 9

A mixture of 5-chlorotriazolo[1,5-a]pyridine (70 mg, 0.46 mmol), [4-(trifluoromethoxy)phenyl]boronic acid (112.64 mg, 0.55 mmol), Pd(t-Bu$_3$P)$_2$ (23.29 mg, 0.05 mmol) and K$_3$PO$_4$ (193.54 mg, 0.91 mmol) in 1,4-Dioxane (5 mL) and Water (1 mL) was stirred at 80° C. for 16 hours under N$_2$. After cooling to room temperature, the mixture was diluted with H$_2$O (20 mL), and the mixture was extracted with EtOAc (40 mL×2). The combined organic phase was washed with water (20 mL) and brine (20 mL), dried over Na$_2$SO$_4$, filtered and concentrated to give the crude product. The crude product was purified by Prep-TLC (silica gel, PE:EtOAc=3:1) to give the product (7.82 mg, 0.03 mmol, 6% yield) as a solid. $^1$H NMR (400 MHz, CDCl$_3$) $\delta_H$=8.82

(d, 1H), 8.14 (s, 1H), 7.88 (s, 1H), 7.68 (d, 2H), 7.37 (d, 2H), 7.23 (d, 1H). LCMS $R_f$=1.12 min in 2.0 min chromatography, 10-80AB, purity 100.00%, MS ESI calcd. for $C_{13}H_9F_3N_3O$ [M+H]$^+$ 280.1, found 279.9.

Example 10. Synthesis of Compound 10

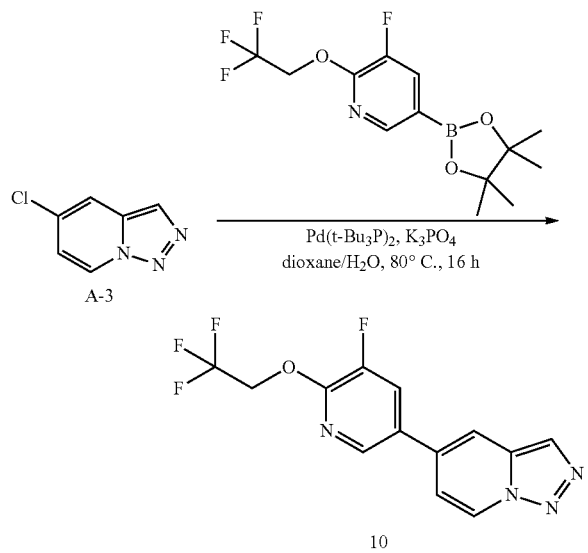

A mixture of 5-chlorotriazolo[1,5-a]pyridine (50 mg, 0.33 mmol), 3-fluoro-5-(4,4,5,5-tetramethyl-1,3,2-dioxaborolan-2-yl)-2-(2,2,2-trifluoroethoxy)pyridine (125.45 mg, 0.39 mmol), Pd(t-Bu$_3$P)$_2$ (24.96 mg, 0.05 mmol) and K$_3$PO$_4$ (138.24 mg, 0.65 mmol) in 1,4-Dioxane (2 mL) and Water (0.20 mL) was stirred at 80° C. for 16 hours to give a brown mixture. After cooling to room temperature, the suspension was diluted with EtOAc (10 mL), filtered through silica gel, eluted with EtOAc (20 mL). The combined filtrates were concentrated to afford the crude product. The crude product was purified by flash chromatography on silica gel (EtOAc in PE=20% to 70%) to give the impure product. The impure product was purified by Prep-HPLC (Waters Xbridge (150 mm×25 mm, 5□m), A=H$_2$O (10 mM NH$_4$HCO$_3$) and B=CH$_3$CN; 38-68% B over 6 minutes) to give the product of (44.72 mg, 0.14 mmol, 44% yield) as a solid. $^1$H NMR (400 MHz, CDCl$_3$) $\delta_H$=8.84 (d, 1H), 8.24 (d, 1H), 8.15 (s, 1H), 7.86 (s, 1H), 7.71 (dd, 1H), 7.17 (dd, 1H), 4.92 (q, 2H). LCMS $R_f$=1.06 min in 2.0 min chromatography, 10-80AB, purity 100%, MS ESI calcd. for $C_{13}H_9F_4N_4O$ [M+H]$^+$ 313.1, found 312.9.

Example 11. Synthesis of Compound 11

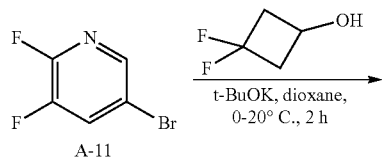

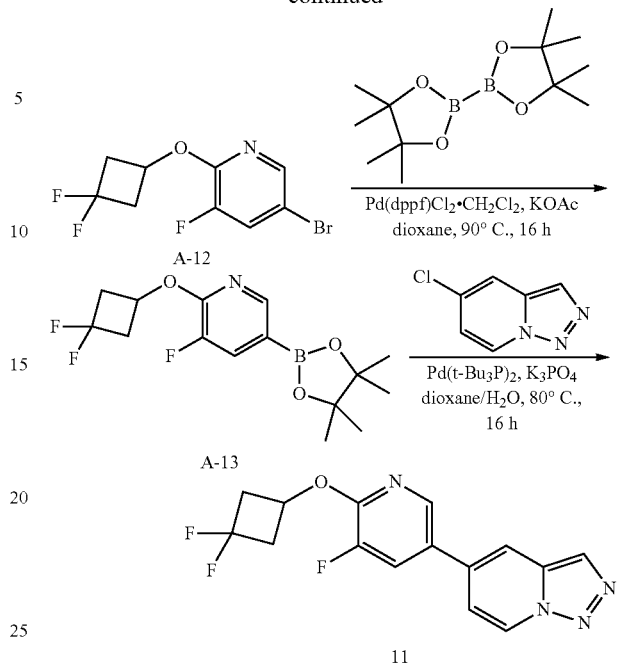

Synthesis of A-12: To a mixture of 5-bromo-2,3-difluoropyridine (1 g, 5.16 mmol) and 3,3-difluorocyclobutanol (668.67 mg, 6.19 mmol) in 1,4-Dioxane (20 mL) was added t-BuOK (1.16 g, 10.31 mmol) at 0° C. Then the mixture was stirred at 20° C. for 2 hours. After cooling to room temperature, the reaction was quenched with sat. NH$_4$Cl (10 mL), and the mixture was extracted with EtOAc (60 mL×2). The combined organic phase was washed with brine (30 mL), dried over Na$_2$SO$_4$, filtered and concentrated to give the crude product. The crude product was purified by flash chromatography on silica gel (EtOAc in PE=0 to 2%) to give the product (1131 mg, 4.01 mmol, 78% yield) as an oil. $^1$H NMR (400 MHz, CDCl$_3$) $\delta_H$=7.98 (d, 1H), 7.52 (dd, 1H), 5.22-5.07 (m, 1H), 3.23-3.05 (m, 2H), 2.91-2.70 (m, 2H).

Synthesis of A-13: A mixture of 5-bromo-2-(3,3-difluorocyclobutoxy)-3-fluoro-pyridine (1131 mg, 4.01 mmol), 4,4,5,5-tetramethyl-2-(4,4,5,5-tetramethyl-1,3,2-dioxaborolan-2-yl)-1,3,2-dioxaborolane (3054.73 mg, 12.03 mmol), KOAc (787.04 mg, 8.02 mmol) and Pd(dppf)Cl$_2$·CH$_2$Cl$_2$ (491.18 mg, 0.60 mmol) in 1,4-Dioxane (25 mL) was stirred at 90° C. for 16 hours under N$_2$. After cooling to room temperature, the mixture was diluted with H$_2$O (30 mL) and extracted with EtOAc (60 mL×2). The combined organic phase was washed with brine (30 mL), dried over Na$_2$SO$_4$, filtered and concentrated to give the crude product. The crude product was purified by flash chromatography on silica gel (EtOAc in PE=0 to 2%) to give the product (1430 mg, 1.90 mmol, 47% yield) as a solid. $^1$H NMR (400 MHz, CDCl$_3$) $\delta_H$=8.25 (s, 1H), 7.66 (dd, 1H), 5.31-5.17 (m, 1H), 3.24-3.07 (m, 2H), 2.89-2.71 (m, 2H), 1.34 (s, 12H).

Synthesis of 11: A mixture of 2-(3,3-difluorocyclobutoxy)-3-fluoro-5-(4,4,5,5-tetramethyl-1,3,2-dioxaborolan-2-yl)pyridine (300.04 mg, 0.91 mmol), 5-chlorotriazolo[1,5-a]pyridine (70 mg, 0.46 mmol), Pd(t-Bu$_3$P)$_2$ (34.94 mg, 0.07 mmol) and K$_3$PO$_4$ (193.54 mg, 0.91 mmol) in 1,4-Dioxane (5 mL) and Water (1 mL) was stirred at 80° C. for 16 hours under N$_2$. After cooling to room temperature, the mixture was diluted with H$_2$O (10 mL) and extracted with EtOAc (20 mL×2). The combined organic phase was washed with brine (10 mL), dried over Na₂SO₄, filtered and concentrated to give the crude product. The product was purified by Prep-TLC (PE:EtOAc=1:3) to give the product (16.96 mg, 0.05 mmol, 12% yield) as a solid. ¹H NMR (400 MHz, CDCl₃) $\delta_H$=8.83 (d, 1H), 8.22 (d, 1H), 8.14 (s, 1H), 7.84 (s, 1H), 7.65 (dd, 1H), 7.16 (dd, 1H), 5.33-5.21 (m, 1H), 3.26-3.14 (m, 2H), 2.93-2.78 (m, 2H). LCMS $R_t$=1.09 min in 2.0 min chromatography, 10-80AB, purity 100%, MS ESI calcd. for $C_{15}H_{12}F_3N_4O$ [M+H]⁺ 321.1, found 321.0.

Example 12. Synthesis of Compound 12

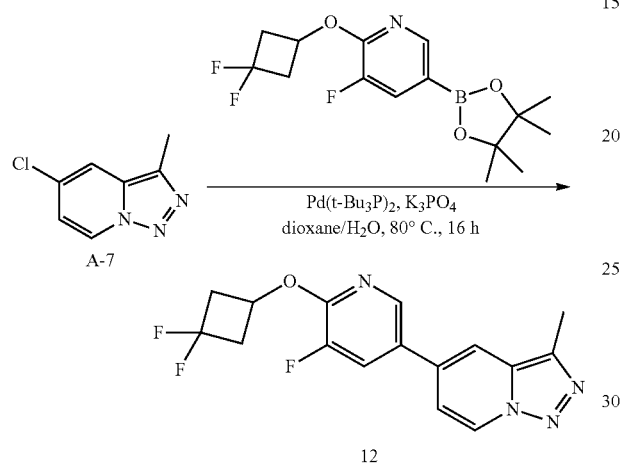

A mixture of 2-(3,3-difluorocyclobutoxy)-3-fluoro-5-(4,4,5,5-tetramethyl-1,3,2-dioxaborolan-2-yl)pyridine (106.04 mg, 0.32 mmol), 5-chloro-3-methyl-triazolo[1,5-a]pyridine (30 mg, 0.18 mmol), Pd(t-Bu₃P)₂ (13.72 mg, 0.03 mmol) and K₃PO₄ (76 mg, 0.36 mmol) in 1,4-Dioxane (3 mL) and Water (0.50 mL) was stirred at 80° C. for 16 hours under N₂. After cooling to room temperature, the mixture was diluted with H₂O (10 mL) and extracted with EtOAc (20 mL×2). The combined organic phase was washed with brine (10 mL), dried over Na₂SO₄, filtered and concentrated to give the crude product. The crude product was purified by Prep-TLC (silica gel, PE:EtOAc=2:1) to give the product (32.01 mg, 0.10 mmol, 53% yield) as a solid. NMR (400 MHz, CDCl₃) $\delta_H$=8.72 (d, 1H), 8.22 (d, 1H), 7.71 (s, 1H), 7.66 (dd, 1H), 7.10 (dd, 1H), 5.30-5.16 (m, 1H), 3.27-3.12 (m, 2H), 2.94-2.78 (m, 2H), 2.68 (s, 3H). LCMS $R_t$=1.21 min in 2.0 min chromatography, 10-80AB, purity 100%, MS ESI calcd. for $C_{16}H_{14}F_3N_4O$ [M+H]⁺ 335.1, found 334.8.

Example 13. Synthesis of Compound 13

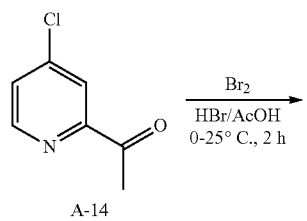

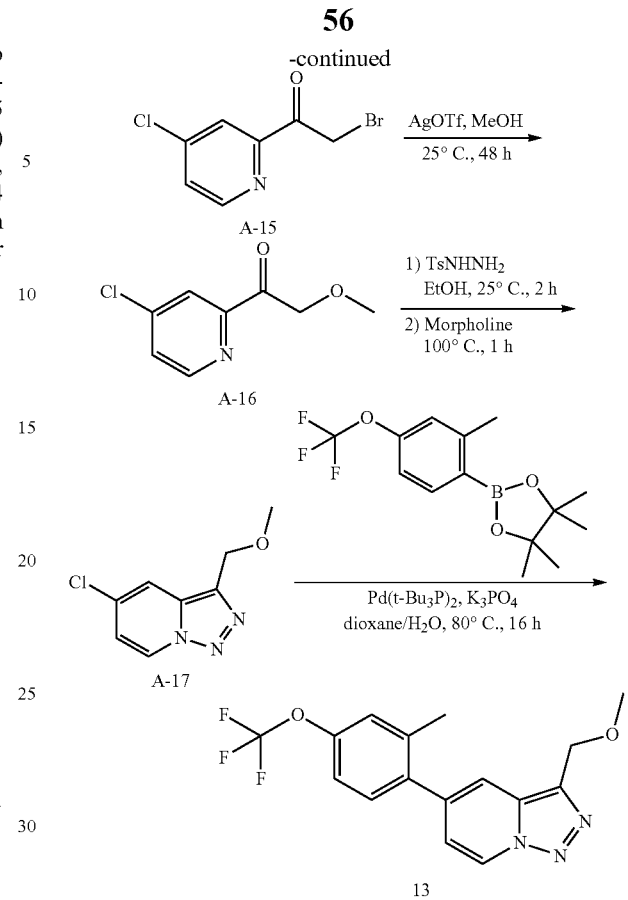

Synthesis of A-15: To a mixture of 1-(4-chloro-2-pyridyl)ethanone (400 mg, 2.57 mmol) in HBr/AcOH (5 mL) was added Br₂ (0.2 mL, 3.86 mmol) at 0° C., then the mixture was stirred at 25° C. for 2 hours. The mixture was quenched with water (20 mL), then the mixture was extracted with EtOAc (30 mL×2). The combined organic phase was washed with sat.Na₂CO₃ (15 mL×3) and brine (15 mL), dried over Na₂SO₄, filtered and concentrated to give the crude product (500 mg, 1.30 mmol, 51% yield) as a solid. LCMS Rt=0.75 min in 1.5 min chromatography, 5-95AB, purity 61.04%, MS ESI calcd. for $C_7H_6BrClNO$ [M+H+2]⁺ 235.9, found 235.8.

Synthesis of A-16: A mixture of 2-bromo-1-(4-chloro-2-pyridyl)ethanone (100 mg, 0.43 mmol) and AgOTf (547.89 mg, 2.13 mmol) in Methanol (5 mL) was stirred at 25° C. for 48 hours. The mixture was filtered through Celite, and the filtrate was concentrated to give the crude product (80 mg, 0.22 mmol) as a solid. The crude product was used next step without further purification. LCMS $R_t$=0.63 min in 1.5 min chromatography, 5-95AB, purity 51.01%, MS ESI calcd. for $C_8H_9ClNO_2$ [M+H]⁺ 186.0, found 185.9.

Synthesis of A-17: A mixture of 1-(4-chloro-2-pyridyl)-2-methoxy-ethanone (80 mg, 0.43 mmol) in Ethanol (1.5 mL) was added 4-methylbenzenesulfonohydrazide (120.4 mg, 0.65 mmol), then the mixture was stirred at 25° C. for 2 hours. The mixture was added into Morpholine (2.5 mL, 28.7 mmol) at 100° C., then the mixture was stirred at 100° C. for 1 hour. After cooling to room temperature, the mixture was concentrated to the residue. The residue was diluted with H₂O (10 mL), and the mixture was extracted with EtOAc (20 mL×2). The combined organic phase was washed with water (10 mL) and brine (10 mL), dried over Na₂SO₄, filtered and concentrated to give the crude product.

The crude product was purified by Prep-TLC (silica gel, PE:EtOAc=3:1) to give the product (32 mg, 0.16 mmol, 36% yield) as a solid. ¹H NMR (400 MHz, CDCl₃) δ$_H$=8.63 (d, 1H), 7.83 (d, 1H), 6.95 (dd, 1H), 4.88 (s, 2H), 3.44 (s, 3H). LCMS Rt=0.62 min in 1.5 min chromatography, 5-95AB, purity 96.30%, MS ESI calcd. for C₈H₉ClN₃O [M+H]⁺ 198.0, found 197.9.

Synthesis of 13: A mixture of 5-chloro-3-(methoxymethyl)triazolo[1,5-a]pyridine (30 mg, 0.15 mmol), 4,4,5,5-tetramethyl-2-[2-methyl-4-(trifluoromethoxy)phenyl]-1,3,2-dioxaborolane (91.72 mg, 0.30 mmol), Pd(t-Bu₃P)₂ (11.64 mg, 0.02 mmol) and K₃PO₄ (64.46 mg, 0.30 mmol) in 1,4-Dioxane (3 mL) and Water (0.50 mL) was stirred at 80° C. for 16 hours under N₂. After cooling to room temperature, the mixture was diluted with H₂O (20 mL), and the mixture was extracted with EtOAc (30 mL×2). The combined organic phase was washed with water (20 mL) and brine (20 mL), dried over Na₂SO₄, filtered and concentrated to give the crude product. The crude product was purified by Prep-TLC (silica gel, PE:DCM:EtOAc=5:5:1) to give the product (14.31 mg, 0.04 mmol, 28% yield) as a solid. ¹H NMR (400 MHz, CDCl₃)=8.75 (dd, 1H), 7.72 (s, 1H), 7.31 (d, 1H), 7.21-7.13 (m, 2H), 6.97 (dd, 1H), 4.93 (s, 2H), 3.45 (s, 3H), 2.34 (s, 3H). LCMS R$_t$=1.27 min in 2.0 min chromatography, 10-80AB, purity 100%, MS ESI calcd. for C₁₆H₁₅F₃N₃O₂[M+H]⁺ 338.1, found 337.8.

Example 14. Synthesis of Compound 14

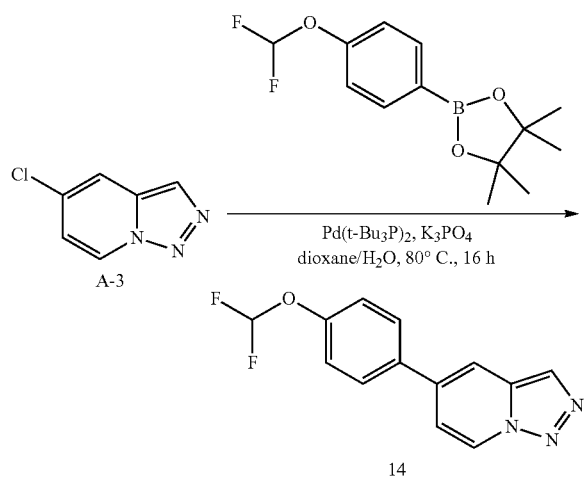

A mixture of 5-chlorotriazolo[1,5-a]pyridine (100 mg, 0.65 mmol), 2-[4-(difluoromethoxy)phenyl]-4,4,5,5-tetramethyl-1,3,2-dioxaborolane (211.04 mg, 0.78 mmol), Pd(t-Bu₃P)₂ (49.92 mg, 0.10 mmol) and K₃PO₄ (276.49 mg, 1.30 mmol) in Water (0.50 mL) and 1,4-Dioxane (5 mL) was stirred at 80° C. for 16 hours to give a brown mixture. After cooling to room temperature, the suspension was diluted with EtOAc (10 mL), filtered through silica gel, eluted with EtOAc (20 mL). The combined filtrates were concentrated to afford crude product. The crude product was purified by Prep-HPLC (Waters Xbridge (150 mm×25 mm, 10 μm) A=H₂O (10 mM NH₄HCO₃) and B=CH₃CN; 35-55% B over 6 minutes) to give the product (56.29 mg, 33% yield) as a solid. ¹H NMR (400 MHz, DMSO-d₆) δ$_H$=9.15 (d, 1H), 8.31-8.21 (m, 2H), 7.96-7.89 (m, 2H), 7.55-7.15 (m, 4H). LCMS R$_t$=1.01 min in 2 min chromatography, 10-80AB, purity 98.63%, MS ESI calcd. for C₁₃H₁₀F₂N₃O [M+H]⁺ 262.1, found 261.9.

Example 15. Synthesis of Compound 15

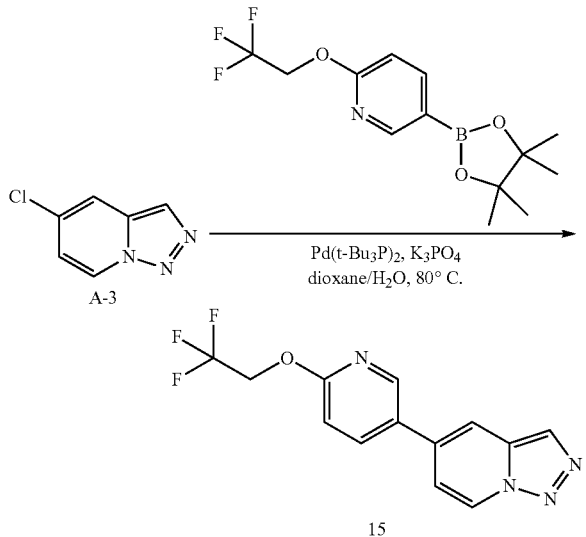

A mixture of 5-(4,4,5,5-tetramethyl-1,3,2-dioxaborolan-2-yl)-2-(2,2,2-trifluoroethoxy)pyridine (236.84 mg, 0.78 mmol), Pd(t-Bu₃P)₂ (49.92 mg, 0.10 mmol), K₃PO₄ (276.49 mg, 1.3 mmol) and 5-chlorotriazolo[1,5-a]pyridine (100 mg, 0.65 mmol) in Water (0.50 mL) and 1,4-Dioxane (5 mL) was stirred at 80° C. for 16 hours to give a brown mixture. After cooling to room temperature, the suspension was diluted with EtOAc (10 mL), filtered through silica gel, eluted with EtOAc (15 mL). The combined filtrates were concentrated to afford crude product. The crude product was purified by flash chromatography on silica gel (EtOAc in PE=20% to 70%) to give impure product. The impure product was also purified by Prep-TLC (silica gel, PE:EA=2:1) to give the product (13.96 mg, 7% yield) as a solid. ¹H NMR (400 MHz, DMSO-d₆) δ$_H$=9.17 (d, 1H), 8.72 (s, 1H), 8.34-8.28 (m, 2H), 8.24 (s, 1H), 7.63-7.53 (m, 1H), 7.21-7.11 (m, 1H), 5.08 (q, 2H). LCMS R$_t$=1.04 min in 2 min chromatography, 10-80AB, purity 100%, MS ESI calcd. for C₁₃H₁₀F₃N₄O [M+H]⁺ 295.1, found 294.9.

Example 16. Synthesis of Compound 16

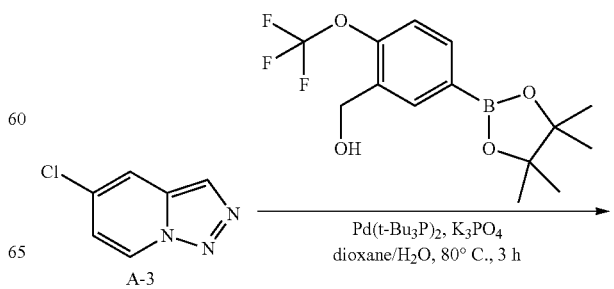

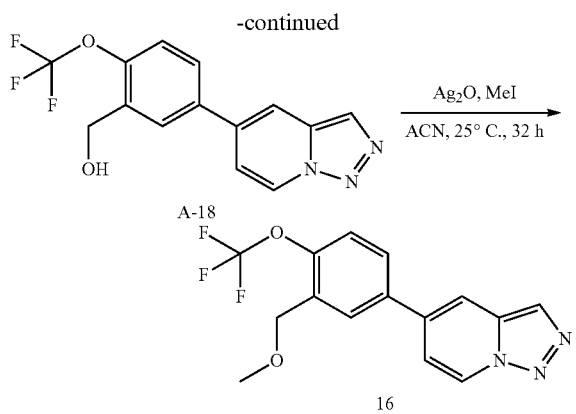

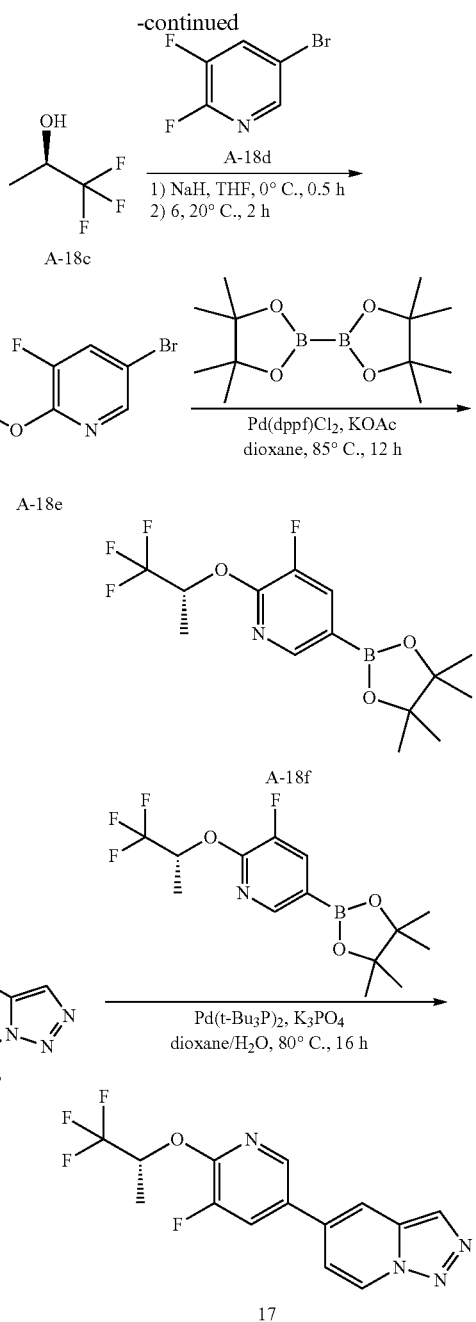

Synthesis of A-18: A mixture of 5-chlorotriazolo[1,5-a]pyridine (150 mg, 0.98 mmol), [5-(4,4,5,5-tetramethyl-1,3,2-dioxaborolan-2-yl)-2-(trifluoromethoxy)phenyl]methanol (372.85 mg, 1.17 mmol), Pd(t-Bu$_3$P)$_2$ (74.88 mg, 0.15 mmol) and K$_3$PO$_4$ (414.73 mg, 1.95 mmol) in 1,4-Dioxane (2 mL) and Water (0.20 mL) was stirred under N$_2$ at 80° C. for 3 hours to give the brown mixture. The mixture was cooled to room temperature, diluted with EtOAc (10 mL), filtered with silica gel, eluted with EtOAc (20 mL) and concentrated to give the crude product. The crude product was purified by flash chromatograph on silica gel (EtOAc in PE=20% to 50% to 80%) to give the product (60 mg, 0.19 mmol, 20% yield) as a solid. $^1$H NMR (400 MHz, CDCl$_3$) $\delta_H$=8.81 (d, 1H), 8.13 (s, 1H), 7.94-7.87 (m, 2H), 7.61 (dd, 1H), 7.39 (dd, 1H), 7.27-7.24 (m, 1H), 4.90 (s, 2H), 1.99 (br s, 1H).

Synthesis of Compound 16: To a mixture of [5-(triazolo[1,5-a]pyridin-5-yl)-2-(trifluoromethoxy)phenyl]methanol (50 mg, 0.16 mmol) in MeCN (2 mL) was added Ag$_2$O (187.35 mg, 0.81 mmol) and iodomethane (114.75 mg, 0.81 mmol), and the mixture was keep out of the light and stirred at 25° C. for 32 hours to give the black suspension. The mixture was diluted with MeCN (10 mL), filtered through Celite, eluted with MeCN (20 mL) and the filtrated was concentrated to give the crude product. The crude product was purified by Prep-HPLC (Waters Xbridge (150 mm×25 mm, 5 μm) A=H$_2$O (10 mM NH$_4$HCO$_3$) and B=CH$_3$CN; 40-70% B over 7 minutes) to give the product (18.43 mg, 56.8 mmol, 35% yield) as a solid. $^1$H NMR (400 MHZ, DMSO-d$_6$) $\delta_H$=9.17 (d, 1H), 8.32 (s, 1H), 8.26 (s, 1H), 7.98 (s, 1H), 7.92 (d, 1H), 7.59-7.45 (m, 2H), 4.56 (s, 2H), 3.38 (s, 3H). LCMS R$_t$=1.09 min in 2.0 min chromatography, 10-80AB, purity 100%, MS ESI calcd. for C$_{15}$H$_{13}$F$_3$N$_3$O$_2$ [M+H]$^+$ 324.1, found 323.9.

Example 17. Synthesis of Compound 17

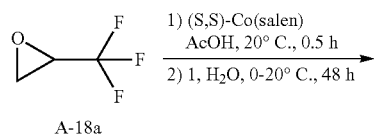

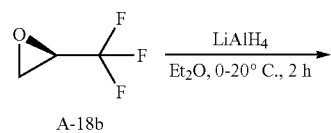

To a mixture of (S,S)—Co(salen) (107.76 mg, 0.18 mmol) (Jacobsen's catalyst, cas: 188264-84-8) in Toluene (3 mL) was added AcOH (0.11 mL, 1.87 mmol). The mixture was stirred at 20° C. for 30 minutes. The solution was concentrated in vacuum to give a crude brown solid. The resulting catalyst residue was dissolved in 2-(trifluoromethyl)oxirane (10 g, 89.25 mmol). To the mixture was added H$_2$O (803.66 mg, 44.6 2 mmol) at 0° C., then the mixture was stirred at 20° C. for 48 hours. The mixture was distilled at ~15° C. under reduced vacuum (~100 mm Hg), and the product was collected with a cold trap (−78° C.) to give (2R)-2-(trifluoromethyl)oxirane (3700 mg, 33.02 mmol, 37% yield) as colorless oil. $^1$H NMR (400 MHz, CDCl$_3$) $\delta_H$=3.49-3.39 (m, 1H), 3.03-2.97 (m, 1H), 2.96-2.90 (m, 1H).

To a mixture of (2R)-2-(trifluoromethyl)oxirane (2 g, 17.85 mmol) in Ether (30 mL) was added LiAlH$_4$ (338.69 mg, 8.92 mmol) at 0° C., then the mixture was stirred at 20° C. for 2 hours. After cooled to 0° C., the mixture was quenched with water (0.64 g), the mixture was stirred at 20° C. for 30 minutes. The mixture was filtered through Celite, eluted with Et$_2$O (30 mL×2), the organic phase was dried over Na$_2$SO$_4$, filtered and concentrated to give the crude product of (2R)-1,1,1-trifluoropropan-2-ol (1100 mg, 9.64 mmol, 54% yield) as colorless oil. $^1$H NMR (400 MHz, DMSO-d$_6$) $\delta_H$=6.03 (d, 1H), 4.16-3.99 (m, 1H), 1.20 (d, 3H).

To a solution of (2R)-1,1,1-trifluoropropan-2-ol (1.10 g, 9.64 mmol) in THF (30 mL) was added NaH (490.93 mg, 12.27 mmol) at 0° C., and the mixture was stirred at 0° C. for 30 mins. Then to the mixture was added 5-bromo-2,3-difluoro-pyridine (1.70 g, 8.77 mmol), and the mixture was stirred at 20° C. for 2 hours. From LCMS, desired MS was observed and no starting material was remained. The mixture was quenched with sat. NH$_4$Cl (20 mL), then the mixture was extracted with EtOAc (50 mL×2). The combined organic phase was washed with water (30 mL) and brine (30 mL), dried over Na$_2$SO$_4$, filtered and concentrated to give the crude product of 5-bromo-3-fluoro-2-[(1R)-2,2,2-trifluoro-1-methyl-ethoxy]pyridine (2300 mg, 7.99 mmol, 91% yield) as oil. $^1$H NMR (400 MHz, CDCl$_3$) $\delta_H$=7.99 (d, 1H), 7.56 (dd, 1H), 5.82-5.69 (m, 1H), 1.54 (d, 3H).

A mixture of 5-bromo-3-fluoro-2-[(1R)-2,2,2-trifluoro-1-methyl-ethoxy]pyridine (2.3 g, 7.99 mmol), 4,4,5,5-tetramethyl-2-(4,4,5,5-tetramethyl-1,3,2-dioxaborolan-2-yl)-1,3,2-dioxaborolane (6.08 g, 23.96 mmol), KOAc (1.57 g, 15.97 mmol) and Pd(dppf)Cl$_2$ (876.39 mg, 1.2 mmol) in 1,4-Dioxane (60 mL) was stirred at 85° C. for 12 hours under N$_2$. From LCMS, desired MS was observed and no starting material was remained. After cooled to r.t., the mixture was concentrated to give the residue. The residue was diluted with H$_2$O (30 mL), and the mixture was extracted with EtOAc (50 mL×2). The combined organic phase was washed with water (20 mL) and brine (20 mL), dried over Na$_e$ SO$_4$, filtered and concentrated to give the crude product. The crude product was purified by flash chromatography on silica gel (EtOAc in PE=0% to 2%) to give the product of 3-fluoro-5-(4,4,5,5-tetramethyl-1,3,2-dioxaborolan-2-yl)-2-[(1R)-2,2,2-trifluoro-1-methyl-ethoxy]pyridine (4200 mg, 12.53 mmol) as oil. $^1$H NMR (400 MHz, CDCl$_3$) $\delta_H$=8.25 (d, 1H), 7.70 (dd, 1H), 5.95-5.82 (m, 1H), 1.54 (d, 3H), 1.34 (s, 12H).

A mixture of 5-chlorotriazolo[1,5-a]pyridine (100 mg, 0.65 mmol), 3-fluoro-5-(4,4,5,5-tetramethyl-1,3,2-dioxaborolan-2-yl)-2-[(1R)-2,2,2-trifluoro-1-methyl-ethoxy]pyridine (327.31 mg, 0.98 mmol), Pd(t-Bu$_3$P)$_2$ (49.92 mg, 0.10 mmol) and K$_3$PO$_4$ (276.49 mg, 1.3 mmol) in 1,4-Dioxane (2 mL) and Water (0.20 mL) was stirred under N$_2$ at 80° C. for 16 hours to give the brown mixture. The mixture was cooled to room temperature, diluted with EtOAc (10 mL), filtered with silica gel, eluted with EtOAc (20 mL) and concentrated to give the crude product. The crude product was purified by Prep-HPLC (Boston Prime C18 (150 mm×30 mm, 5 µm) A=H$_2$O (0.05% NH$_4$OH) and B=CH$_3$CN; 60-90% B over 7 minutes) to give the product (87.3 mg, 41% yield) as a solid. $^1$H NMR (400 MHz, DMSO-d$_6$) $\delta_H$=9.20 (d, 1H), 8.57 (d, 1H), 8.43-8.34 (m, 2H), 8.27 (s, 1H), 7.61 (dd, 1H), 6.07-5.93 (m, 1H), 1.54 (d, 3H). LCMS R$_t$=1.10 min in 2.0 min chromatography, 10-80AB, purity 100%, MS ESI calcd. for C$_{14}$H$_{11}$F$_4$N$_4$O [M+H]$^+$ 327.1, found 326.9.

Example 18. Synthesis of Compound 18

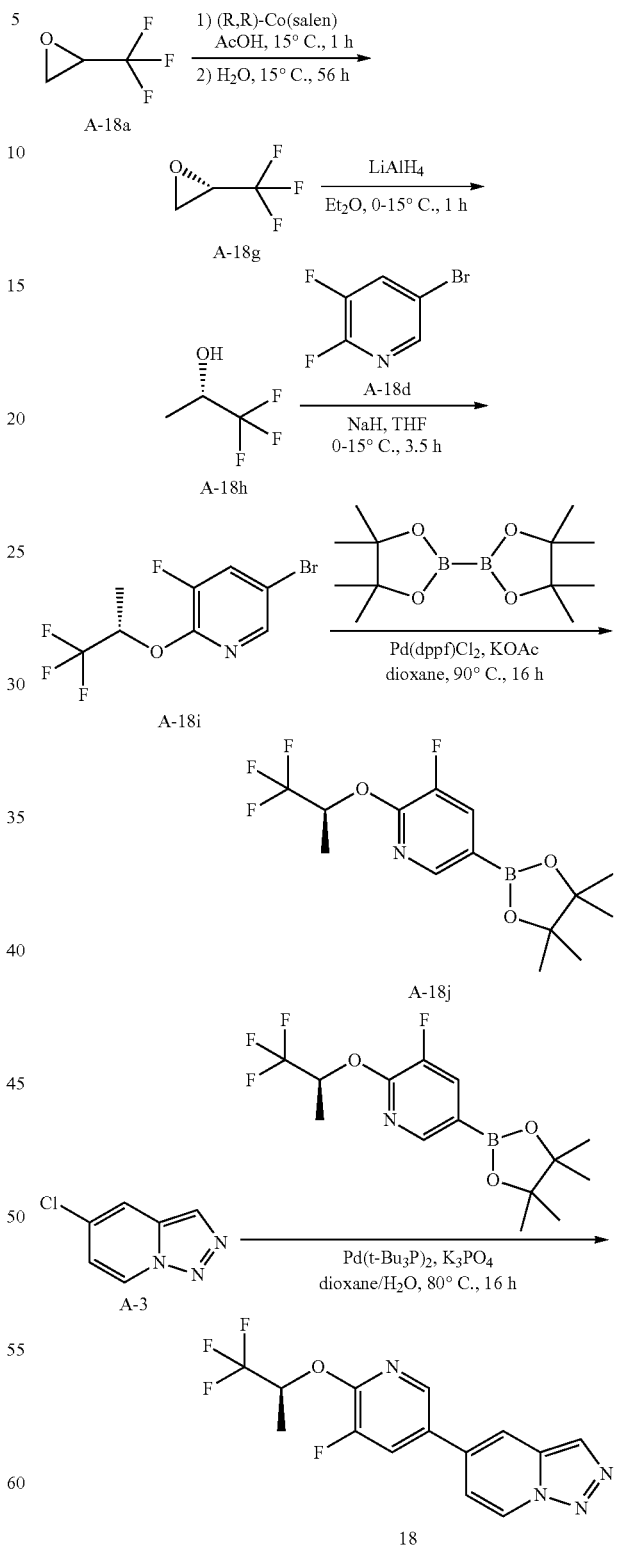

To a solution of (R,R)—Co(salen) (550 mg, 0.91 mmol) (Jacobsen's catalyst, cas: 176763-62-5) in Toluene (10 mL) was added AcOH (0.5 5 mL, 9.6 mmol), and the mixture was stirred at 15° C. open to air for 1 hour. Then the mixture was concentrated, and the brown residue was dissolved in 2-(trifluoromethyl)oxirane (50 g, 446.23 mmol). To the mixture was added H$_2$O (4.4 mL, 244.44 mmol) at 0° C. and the mixture was stirred at 15° C. for 56 hours. The mixture was distilled at ~15° C. under reduced vacuum (~100 mm Hg), and the product was collected with a cold trap (−78° C.) to give the product of (2S)-2-(trifluoromethyl)oxirane (18000 mg, 160.64 mmol, 36% yield) as colorless liquid.

Note: the product was ring-opened with BnNH$_2$ (1 eq), and the resulted solid triturated from n-hexane and analyzed by SFC to show the ee % was about 86%. Method: Column: Chiral CD-Ph 250×4.6 mm I.D., 5 µm; Mobile phase: from 10% to 80% of B in A; A: Water with 0.069% TFA B: Acetonitrile; Flow rate: 0.8 mL/min; Column Temperature: 30° C.

$^1$H NMR (400 MHz, CDCl$_3$) $\delta_H$=3.47-3.40 (m, 1H), 3.02-2.97 (m, 1H), 2.96-2.91 (m, 1H).

To a mixture of (2S)-2-(trifluoromethyl)oxirane (18 g, 160.64 mmol) in Ether (150 mL) was added LiAlH$_4$ (3.05 g, 80.32 mmol) at 0° C., then the mixture was stirred at 15° C. for 1 hours. After cooled to 0° C., the mixture was quenched with water (4 mL), and the mixture was stirred at 20° C. for 30 minutes. The mixture was filtered through Celite, eluted with Et$_2$O (100 mL×3), and the organic phase was dried over Na$_2$SO$_4$, filtered and concentrated to give the crude product of (2S)-1,1,1-trifluoropropan-2-ol (8000 mg, 70.13 mmol, 44% yield) as colorless oil. $^1$H NMR (400 MHz, DMSO-d$_6$) $\delta_H$=6.03 (d, 1H), 4.14-3.97 (m, 1H), 1.20 (d, 3H).

To a solution of (2S)-1,1,1-trifluoropropan-2-ol (8 g, 70.13 mmol) in THF (100 mL) was added NaH (2.81 g, 70.13 mmol) at 0° C., and the mixture was stirred at 0° C. for 30 mins. Then to the mixture was added 5-bromo-2,3-difluoro-pyridine (13.6 g, 70.13 mmol), and the mixture was stirred at 15° C. for 3 hours. From TLC (PE), no starting material (Rf=0.5, UV) was remained and a new spot (Rf=0.6, UV) was observed. The mixture was diluted with sat.NH$_4$Cl (50 mL) and extracted with EtOAc (100 mL×2). The combined organic phase was washed with H$_2$O (30 mL) and brine (30 mL), dried over Na$_2$SO$_4$, filtered and concentrated to give the crude product of 5-bromo-3-fluoro-2-[(1S)-2,2,2-trifluoro-1-methyl-ethoxy]pyridine (18000 mg, 62.49 mmol, 89% yield) as oil.

A mixture of 5-bromo-3-fluoro-2-[(1S)-2,2,2-trifluoro-1-methyl-ethoxy]pyridine (3 g, 10.42 mmol), 4,4,5,5-tetramethyl-2-(4,4,5,5-tetramethyl-1,3,2-dioxaborolan-2-yl)-1,3,2-dioxaborolane (7.93 g, 31.25 mmol), KOAc (3.07 g, 31.25 mmol) and Pd(dppf)Cl$_2$ (1.14 g, 1.56 mmol) in 1,4-Dioxane (150 mL) was stirred at 90° C. for 16 hours. From LCMS, desired MS was observed and no starting material was remained. After cooled to r.t., the mixture was concentrated to give the crude product. The crude product was diluted with PE (200 mL), filtered through silica gel and eluted with PE (150 mL×2). The filtrate was concentrated to give the crude product of 3-fluoro-5-(4,4,5,5-tetramethyl-1,3,2-dioxaborolan-2-yl)-2-[(1S)-2,2,2-trifluoro-1-methyl-ethoxy]pyridine (5000 mg, 14.92 mmol, crude) as oil. $^1$H NMR (400 MHz, CDCl$_3$) $\delta_H$=8.17 (d, 1H), 7.62 (dd, 1H), 5.89-5.72 (m, 1H), 1.46 (d, 3H), 1.26 (s, 12H).

A mixture of 5-chlorotriazolo[1,5-a]pyridine (80 mg, 0.52 mmol), 3-fluoro-5-(4,4,5,5-tetramethyl-1,3,2-dioxaborolan-2-yl)-2-[(1S)-2,2,2-trifluoro-1-methyl-ethoxy]pyridine (261.85 mg, 0.78 mmol), Pd(t-Bu$_3$P)$_2$ (39.93 mg, 0.08 mmol) and K$_3$PO$_4$ (221.19 mg, 1.04 mmol) in 1,4-Dioxane (2 mL) and Water (0.20 mL) was stirred at 80° C. for 16 hours to give the brown mixture. The mixture was cooled to room temperature, diluted with EtOAc (10 mL), filtered through silica gel, eluted with EtOAc (20 mL) and concentrated to give the crude product. The crude product was purified by Prep-HPLC (Waters Xbridge (150 mm×25 mm, 5 µm), A=H$_2$O (10 mM NH$_4$HCO$_3$) and B=CH$_3$CN; 48-68% B over 6 minutes) to give the product (81.84 mg, 0.24 mmol, 47% yield) as a solid. $^1$H NMR (400 MHz, DMSO-d$_6$) $\delta_H$=9.20 (d, 1H), 8.57 (d, 1H), 8.42-8.35 (m, 2H), 8.27 (s, 1H), 7.61 (dd, 1H), 6.08-5.94 (m, 1H), 1.54 (d, 3H). LCMS R$_t$=1.10 min in 2.0 min chromatography, 10-80AB, purity 97.94%, MS ESI calcd. for C$_{14}$H$_{11}$F$_4$N$_4$O [M+H]$^+$ 327.1, found 326.9.

Example 19. Synthesis of Compound 19

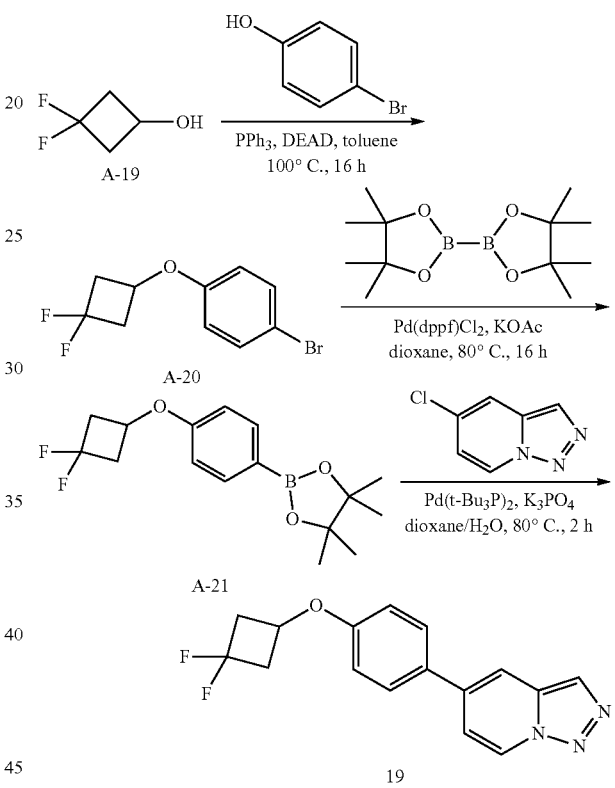

Synthesis of A-20: To a mixture of 4-bromophenol (384.15 mg, 2.22 mmol), 3,3-difluorocyclobutanol (200 mg, 1.85 mmol) and Ph$_3$P (1.46 g, 5.55 mmol) in Toluene (15 mL) was added DEAD (966.69 mg, 5.55 mmol) under N$_2$. Then the mixture was heated and stirred at 100° C. for 16 hours. The mixture was concentrated, and the residue was diluted with EtOAc (10 mL), then washed with H$_2$O (10 mL) and brine (10 mL). The organic phase was dried over Na$_2$SO$_4$, filtered and concentrated to give the crude product. The crude product was purified by Prep-TLC (EtOAc in PE=10:1) to give the product (80 mg, 0.30 mmol, 16% yield) as an oil. $^1$H NMR (400 MHz, CDCl$_3$) $\delta_H$=7.39 (d, 2H), 6.70 (d, 2H), 4.70-4.53 (m, 1H), 3.17-2.99 (m, 2H), 2.84-2.64 (m, 2H).

Synthesis of A-21: A brown mixture of 1-bromo-4-(3,3-difluorocyclobutoxy)benzene (80 mg, 0.30 mmol), 4,4,5,5-tetramethyl-2-(4,4,5,5-tetramethyl-1,3,2-dioxaborolan-2-yl)-1,3,2-dioxaborolane (115.83 mg, 0.46 mmol), Pd(dppf)Cl$_2$ (33.38 mg, 0.05 mmol) and KOAc (59.69 mg, 0.61 mmol) in 1,4-Dioxane (2 mL) was stirred at 80° C. for 16 hours under N₂. The mixture was cooled to room temperature, diluted with EtOAc (5 mL), filtered with silica gel, eluted with EtOAc (10 mL) and concentrated to give the crude product. The crude product was purified by Prep-TLC (EtOAc in PE=10:1) to give the product (80 mg, 0.26 mmol, 85% yield) as an oil. NMR (400 MHz, CDCl₃) $\delta_H$=7.76 (d, 2H), 6.80 (d, 2H), 4.74-4.63 (m, 1H), 3.16-3.04 (m, 2H), 2.83-2.69 (m, 2H), 1.34 (s, 12H).

Synthesis of 19: A mixture of 5-chlorotriazolo[1,5-a]pyridine (40 mg, 0.26 mmol), 2-[4-(3,3-difluorocyclobutoxy)phenyl]-4,4,5,5-tetramethyl-1,3,2-dioxaborolane (80 mg, 0.26 mmol), Pd(t-Bu₃P)₂ (19.97 mg, 0.04 mmol) and K₃PO₄ (110.59 mg, 0.52 mmol) in 1,4-Dioxane (2 mL) and Water (0.20 mL) was stirred at 80° C. for 2 hours to give the brown mixture. The mixture was cooled to room temperature, diluted with EtOAc (10 mL), filtered with silica gel, eluted with EtOAc (20 mL) and concentrated to give the crude product. The crude product was purified by Prep-TLC (EtOAc in PE=1:1) to give the product (3.36 mg, 0.011 mmol, 4.3% yield) as a solid. ¹H NMR (400 MHz, CDCl₃) $\delta_H$=8.79 (d, 1H), 8.10 (s, 1H), 7.84 (s, 1H), 7.62 (d, 2H), 7.24 (dd, 1H), 6.96 (d, 2H), 4.81-4.68 (m, 1H), 3.22-3.10 (m, 2H), 2.90-2.76 (m, 2H). LCMS $R_t$=1.10 min in 2.0 min chromatography, 10-80AB, purity 100%, MS ESI calcd. for $C_{16}H_{14}F_2N_3O$ [M+H]⁺ 302.1, found 301.9.

Example 20. Synthesis of Compound 20

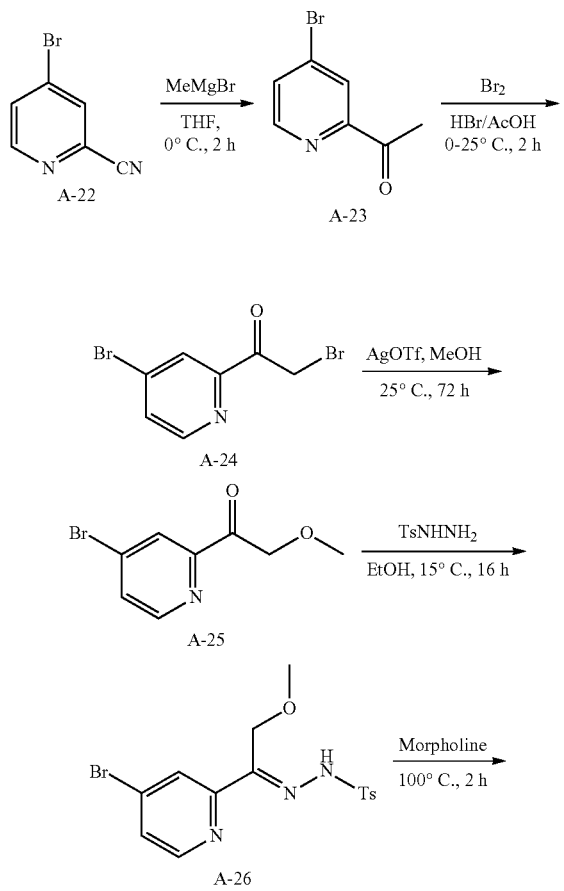

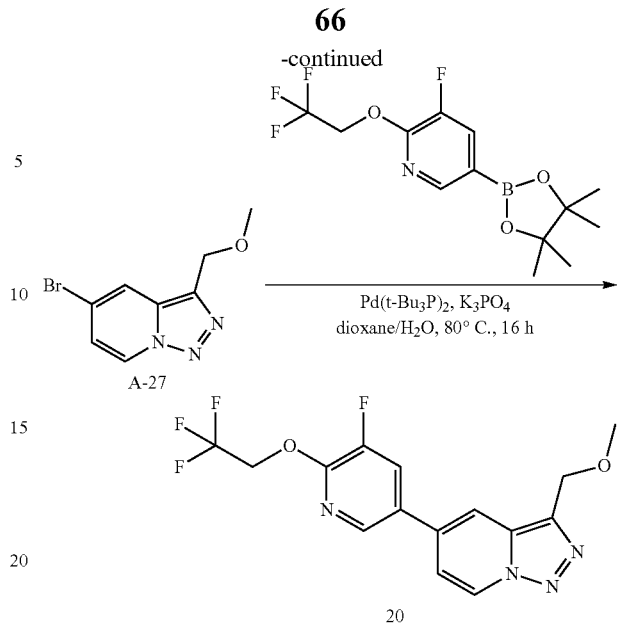

Synthesis of A-23: To a solution of 4-bromopyridine-2-carbonitrile (5 g, 27.32 mmol) in THF (80 mL) at 0° C. was added MeMgBr (18.21 mL, 54.64 mmol) dropwise. The reaction mixture was stirred at 0° C. for 2 hours to give a brown mixture. The reaction mixture was quenched with 1N HCl (150 mL), extracted with EtOAc (100 mL×2). The combined organic phase was washed with brine (100 mL), dried over Na₂SO₄, filtered and concentrated to give the crude product (4700 mg, 86% yield) as a solid. ¹H NMR (400 MHz, CDCl₃) $\delta_H$=8.50 (d, 1H), 8.20 (d, 1H), 7.64 (dd, 1H), 2.71 (s, 3H).

Synthesis of A-24: To a mixture of 1-(4-bromo-2-pyridyl)ethanone (2 g, 10 mmol) in HBr/AcOH (20 mL, 10 mmol) was added Br₂ (0.67 mL, 13 mmol) at 0° C., then the mixture was stirred at 15° C. for 2 hours. The mixture was quenched with water (50 mL), then the mixture was extracted with EtOAc (30 mL×2). The combined organic phase was washed with sat. Na₂CO₃ (30 mL×3) and brine (15 mL), dried over Na₂SO₄, filtered and concentrated to give the crude product (2200 mg, 7.89 mmol, 79% yield) as a solid. LCMS $R_t$=0.82 min in 1.5 min chromatography, 5-95AB, purity 70.74%, MS ESI calcd. for $C_7H_6Br_2NO$ [M+H+2]⁺ 279.9, found 279.7.

Synthesis of A-25: A mixture of 2-bromo-1-(4-bromo-2-pyridyl)ethanone (2.2 g, 7.89 mmol) and AgOTf (10.13 g, 39.44 mmol) in Methanol (30 mL) was stirred at 25° C. for 72 hours to give a black mixture. The mixture was treated with brine (200 mL) and EtOAc (200 mL). The organic phase was separated, then washed with brine (50 mL), dried over Na₂SO₄, filtered and concentrated. The residue was purified by flash chromatography on silica gel (EtOAc in PE=0% to 10% to 25%) to give the product (900 mg, 3.91 mmol, 50% yield) as a solid. ¹H NMR (400 MHz, CDCl₃) $\delta_H$=8.46 (d, 1H), 8.24 (d, 1H), 7.71-7.65 (m, 1H), 5.02 (s, 2H), 3.55 (s, 3H).

Synthesis of A-26: A mixture of 1-(4-bromo-2-pyridyl)-2-methoxy-ethanone (800 mg, 3.48 mmol) and 4-methylbenzenesulfonohydrazide (971.38 mg, 5.22 mmol) in Ethanol (20 mL) was stirred at 15° C. for 16 hours to give a mixture. The reaction mixture was concentrated to give the crude product (1600 mg, 1.46 mmol, 42% yield) as a solid. LCMS $R_t$=0.86 min in 1.5 min chromatography, 5-95AB, purity 36.40%, MS ESI calcd. for $C_{15}H_{17}BrN_3O_3S$ [M+H+2]⁺ 400.0, found 399.8.

Synthesis of A-27: A mixture of N-[[1-(4-bromo-2-pyridyl)-2-methoxy-ethylidene]amino]-4-methyl-benzenesulfonamide (1.6 g, 4.02 mmol) in morpholine (20 mL, 229.57 mmol) was stirred at 100° C. for 2 hours to give a mixture. After cooling to room temperature, the reaction mixture was concentrated. The residue was purified by flash chromatography on silica gel (EtOAc in PE=0% to 10% to 20%) to give the product (450 mg, 1.86 mmol, 46% yield) as a solid. $^1$H NMR (400 MHz, CDCl$_3$) $\delta_H$=8.57 (d, 1H), 8.06-7.99 (m, 1H), 7.06 (dd, 1H), 4.88 (s, 2H), 3.44 (s, 3H).

Synthesis of 20: A mixture of 5-bromo-3-(methoxymethyl)triazolo[1,5-a]pyridine (150 mg, 0.62 mmol), 3-fluoro-5-(4,4,5,5-tetramethyl-1,3,2-dioxaborolan-2-yl)-2-(2,2,2-trifluoroethoxy)pyridine (397.92 mg, 1.24 mmol), K$_3$PO$_4$ (263.11 mg, 1.24 mmol) and Pd(t-Bu$_3$P)$_2$ (63.33 mg, 0.12 mmol) in 1,4-Dioxane (4 mL) and Water (0.40 mL) under N$_2$ was stirred at 80° C. for 16 hours to give a brown mixture. After cooling to room temperature, the reaction mixture was diluted with EtOAc (10 mL), and filtered through a Celite pad, eluted with EtOAc (10 mL). The filtrate was concentrated. The residue was purified by Prep-HPLC (Waters Xbridge (150 mm×25 mm, 5 μm) A=H$_2$O (10 mM NH$_4$HCO$_3$) and B=CH$_3$CN; 40-55% B over 7 minutes) to give the product (79.72 mg, 0.22 mmol, 79% yield) as a solid. $^1$H NMR (400 MHz, CDCl$_3$) $\delta_H$=8.79 (d, 1H), 8.25 (d, 1H), 7.94 (s, 1H), 7.72 (dd, 1H), 7.17 (dd, 1H), 4.98-4.88 (m, 4H), 3.47 (s, 3H). LCMS R$_f$=1.10 min in 2.0 min chromatography, 10-80AB, purity 100%, MS ESI calcd. for C$_{15}$H$_{13}$F$_4$N$_4$O$_2$ [M+H]$^+$ 357.1, found 357.0.

Example 21. Synthesis of Compound 21

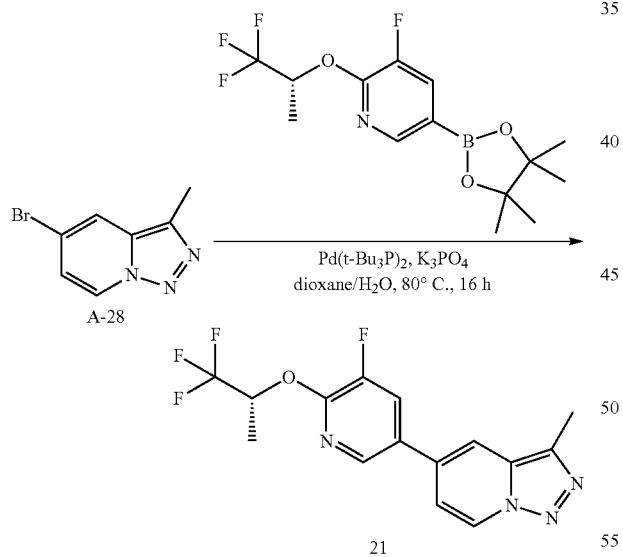

A mixture of 5-bromo-3-methyl-triazolo[1,5-a]pyridine (200 mg, 0.94 mmol), 3-fluoro-5-(4,4,5,5-tetramethyl-1,3,2-dioxaborolan-2-yl)-2-[(1R)-2,2,2-trifluoro-1-methyl-ethoxy]pyridine (379.27 mg, 1.13 mmol), K$_3$PO$_4$ (400.47 mg, 1.89 mmol) and Pd(t-Bu$_3$P)$_2$ (96.4 mg, 0.19 mmol) in 1,4-Dioxane (4 mL) and Water (0.40 mL) under N$_2$ was stirred at 80° C. for 16 hours to give a brown mixture. After cooling to room temperature, the reaction mixture was diluted with EtOAc (10 mL), and filtered through a Celite pad, eluted with EtOAc (10 mL). The filtrate was concentrated. The residue was purified by Prep-HPLC (Agela DuraShell (150 mm×25 mm 5 μm), A=H$_2$O (0.04% NH$_3$H$_2$O+10 mM NH$_4$HCO$_3$) and B=CH$_3$CN; 45-75% B over 8.5 minutes) to give impure product, the impure was triturated from CH$_2$Cl$_2$/n-haxane (1 mL: 4 mL) to give the product (44.27 mg, 0.13 mmol, 14% yield) as a solid. $^1$H NMR (400 MHz, DMSO-d$_6$) $\delta_H$=9.06 (d, 1H), 8.59 (d, 1H), 8.46-8.34 (m, 2H), 7.55 (dd, 1H), 6.08-5.95 (m, 1H), 2.59 (s, 3H), 1.54 (d, 3H). LCMS R$_f$=1.08 min in 2.0 min chromatography, 10-80AB, purity 98.52%, MS ESI calcd. for C$_{15}$H$_{13}$F$_4$N$_4$O [M+H]$^+$ 341.1, found 340.9.

Example 22. Synthesis of Compound 22

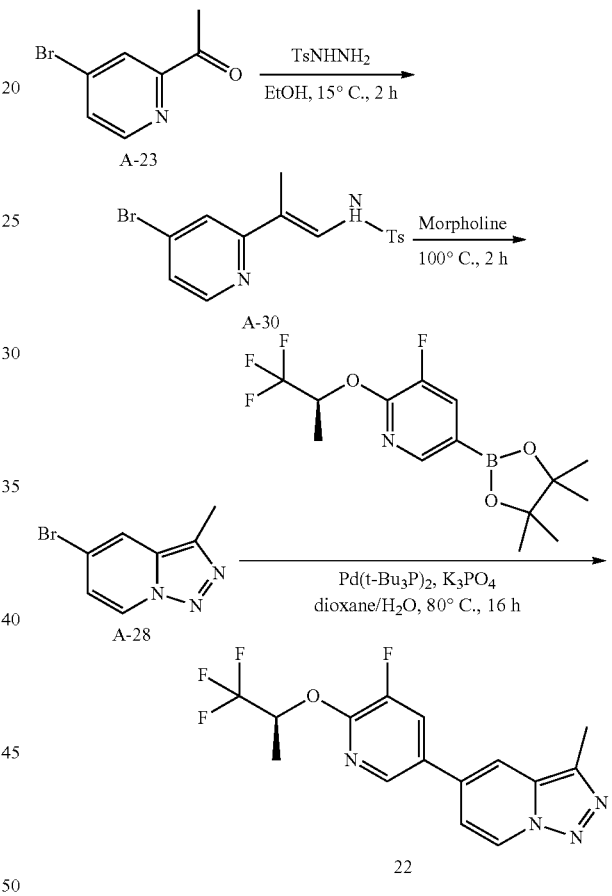

Synthesis of A-30: A mixture of 1-(4-bromo-2-pyridyl)ethanone (2.7 g, 13.5 mmol) and 4-methylbenzenesulfonohydrazide (3.77 g, 20.25 mmol) in Ethanol (30 mL) was stirred at 15° C. for 2 hours to give a brown mixture. The reaction mixture was concentrated to give the crude product (6000 mg, 12.35 mmol, 92% yield) as a solid. LCMS R$_f$=0.84 min in 1.5 min chromatography, 5-95AB, purity 75.82%, MS ESI calcd. for C$_{14}$H$_{15}$BrN$_3$O$_2$S [M+H+2]$^+$ 370.0, found 369.9.

Synthesis of A-28: A mixture of N-[1-(4-bromo-2-pyridyl)ethylideneamino]-4-methyl-benzenesulfonamide (6 g, 16.29 mmol) in Morpholine (30 mL, 344.35 mmol) was stirred at 100° C. for 2 hours to give a brown mixture. After cooling to room temperature, the reaction mixture was concentrated. The residue was purified by flash chromatography on silica gel (EtOAc in PE=0% to 20% to 30%) to give the product (2200 mg, 10.38 mmol, 64% yield) as a solid. $^1$H NMR (400 MHz, CDCl$_3$) $\delta_H$=8.52 (d, 1H), 7.81 (s, 1H), 7.00-6.98 (m, 1H), 2.60 (s, 3H).

Synthesis of 22: A mixture of 5-bromo-3-methyl-triazolo[1,5-a]pyridine (200 mg, 0.94 mmol), 3-fluoro-5-(4,4,5,5-tetramethyl-1,3,2-dioxaborolan-2-yl)-2-[(1S)-2,2,2-trifluoro-1-methyl-ethoxy]pyridine (379.27 mg, 1.13 mmol), K$_3$PO$_4$ (400.47 mg, 1.89 mmol) and Pd(t-Bu$_3$P)$_2$ (96.4 mg, 0.19 mmol) in 1,4-Dioxane (4 mL) and Water (0.40 mL) under N$_2$ was stirred at 80° C. for 16 hours to give a brown mixture. After cooling to room temperature, the reaction mixture was diluted with EtOAc (10 mL), and filtered through a Celite pad, eluted with EtOAc (10 mL). The filtrate was concentrated. The residue was purified by Prep-HPLC (Waters Xbridge (150 mm×25 mm, 5 µm) A=H$_2$O (10 mM NH$_4$HCO$_3$) and B=CH$_3$CN; 46-66% B over 6 minutes) to give the product (190.14 mg, 0.55 mmol, 58% yield) as a solid. $^1$H NMR (400 MHz, DMSO-d$_6$) $\delta_H$=9.07 (d, 1H), 8.59 (d, 1H), 8.46-8.35 (m, 2H), 7.56 (dd, 1H), 6.07-5.96 (m, 1H), 2.59 (s, 3H), 1.54 (d, 3H). LCMS R$_t$=1.21 min in 2.0 min chromatography, 10-80AB, purity 100%, MS ESI calcd. for C$_{15}$H$_{13}$F$_4$N$_4$O [M+H]$^+$ 341.1, found 340.9.

Example 23. Synthesis of Compound 23-1 and 23-2

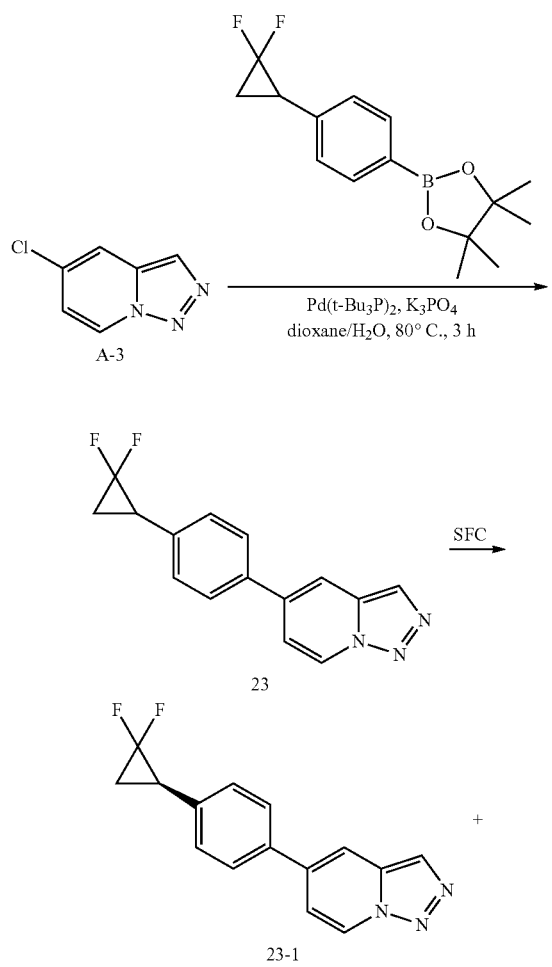

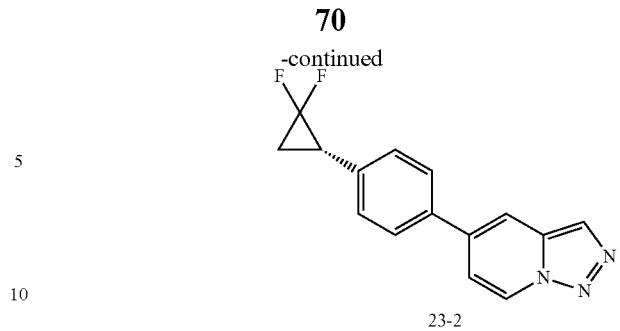

A mixture of 2-[4-(2,2-difluorocyclopropyl)phenyl]-4,4,5,5-tetramethyl-1,3,2-dioxaborolane (437.77 mg, 1.56 mmol), Pd(t-Bu$_3$P)$_2$ (99.83 mg, 0.20 mmol), K$_3$PO$_4$ (552.97 mg, 2.60 mmol), and 5-chlorotriazolo[1,5-a]pyridine (200 mg, 1.30 mmol) in 1,4-Dioxane (3 mL) and Water (0.30 mL) was stirred at 80° C. for 16 hours. After cooling to room temperature, the mixture was concentrated to the residue. The residue was diluted with H$_2$O (20 mL) and extracted with EtOAc (20 mL×2). The combined organic phase was washed with brine (10 mL), dried over Na$_2$SO$_4$, filtered and concentrated to give the crude product. The crude product was purified by purified by Prep-HPLC (Waters Xbridge (150 mm×25 mm, 5 µm), A=H$_2$O (10 mM NH$_4$HCO$_3$) and B=CH$_3$CN; 37-57% B over 7 minutes) to give the product (30 mg, 0.11 mmol, 8% yield) as a solid. The product was analyzed by SFC and showed two peaks (Peak 1: Rt=4.89 min, Peak 2: Rt=5.47 min).

Method: Column: Chiralpak AD-3 150×4.6 mm I.D, 3 µm Mobile phase: A: CO$_2$ B:ethanol (0.05% DEA), Gradient: from 5% to 40% of B in 5 min and hold 40% for 2.5 min, then 5% of B for 2.5 min Flow rate: 2.5 mL/min Column temp.: 35° C. $^1$H NMR CDCl$_3$ 400 MHz $\delta_H$=8.80 (d, 1H), 8.11 (s, 1H), 7.88 (s, 1H), 7.63 (d, 2H), 7.38 (d, 2H), 7.26-7.23 (m, 1H), 2.93-2.77 (m, 1H), 1.98-1.85 (m, 1H), 1.76-1.64 (m, 1H). The product was analyzed by SFC showed two peaks (Peak 1: Rt=4.89 min, Peak 2: Rt=5.47 min). Method: Column: Chiralpak AD-3 150×4.6 mm I.D, 3 µm Mobile phase: A: CO$_2$ B:ethanol (0.05% DEA), Gradient: from 5% to 40% of B in 5 min and hold 40% for 2.5 min, then 5% of B for 2.5 min Flow rate: 2.5 mL/min Column temp.: 35° C.

The product was purified by SFC (Phenomenex-Amylose-1 (250 mm×30 mm, 5 µm); A=CO$_2$ and B=MEOH (0.1% NH$_3$H$_2$O); 38° C.; 50 mL/min; 40% B; 8 min run; 7 injections, Rt of peak 1=5.5 min, Rt of peak 2=6.5 min) to give the product of 5-[4-[(1R)-2,2-difluorocyclopropyl]phenyl]triazolo[1,5-a]pyridine (5.48 mg, 0.02 mmol, 21.68% yield, 98.92% purity) (Peak 1, Rt=4.89 min in SFC: 23-1) as a solid and 5-[4-[(1S)-2,2-difluorocyclopropyl]phenyl]triazolo[1,5-a]pyridine (8.78 mg, 32.20 µmol, 29.11% yield, 99.45% purity) (Peak 2: Rt=5.47 min in SFC: 23-2) as a solid.

23-1: $^1$H NMR (400 MHz, MeOD-d$_4$) $\delta_H$=8.94 (d, 1H), 8.22-8.12 (m, 2H), 7.76 (d, 2H), 7.51 (dd, 1H), 7.41 (d, 2H), 3.00-2.85 (m, 1H), 1.99-1.87 (m, 1H), 1.86-1.75 (m, 1H). LCMS R$_t$=1.00 min in 2 min chromatography, 10-80AB, purity 100%, MS ESI calcd. for C$_{15}$H$_{12}$F$_2$N$_3$ [M+H]$^+$ 272.1, found 271.9. 23-2: $^1$H NMR (400 MHz, DMSO-d$_6$) $\delta_H$=9.14 (d, 1H), 8.27 (s, 1H), 8.23 (s, 1H), 7.83 (d, 2H), 7.55-7.53 (m, 1H), 7.43 (d, 2H), 2.07-2.00 (m, 1H), 3.11-3.05 (m, 2H). LCMS R$_t$=1.05 min in 2 min chromatography, 10-80AB, purity 100%, MS ESI calcd. for C$_{15}$H$_{12}$F$_2$N$_3$ [M+H]$^+$ 272.1, found 271.9.

Note: the enantiomers were randomly assigned.

Example 24. Synthesis of Compound 24

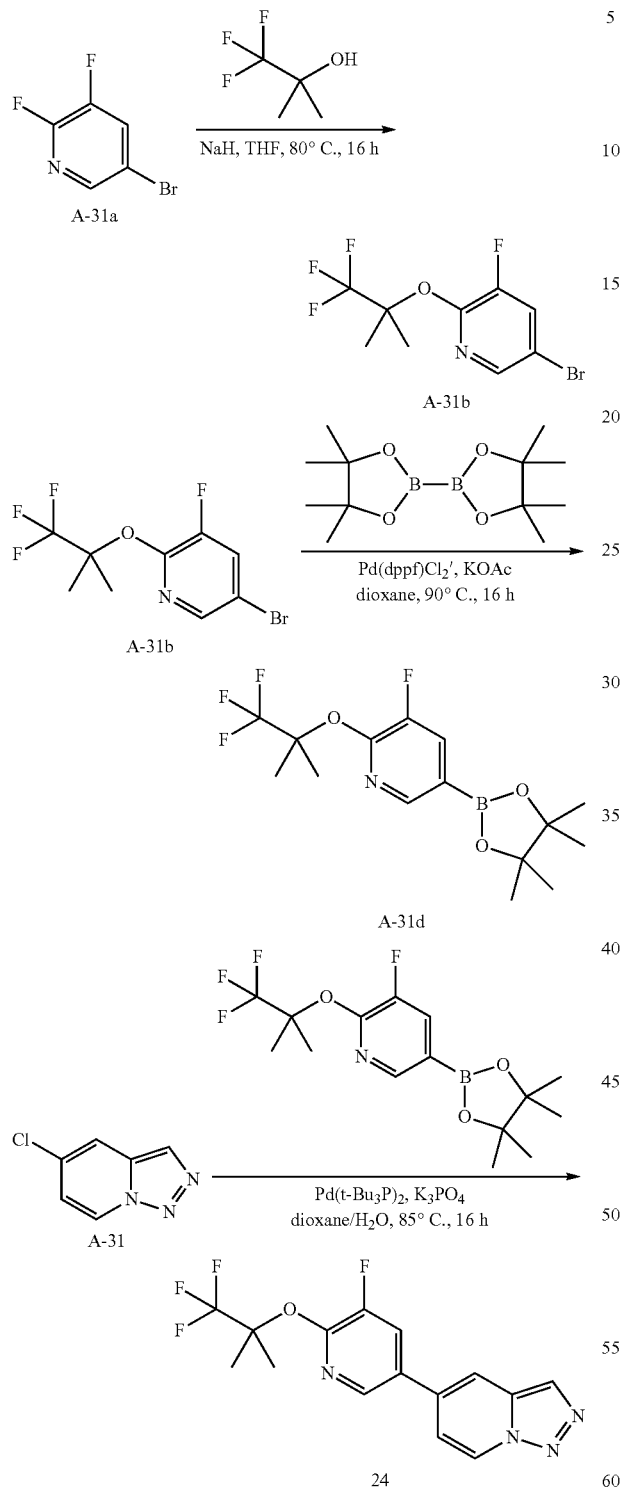

To a solution of 1,1,1-trifluoro-2-methyl-propan-2-ol (3 g, 23.42 mmol) in THF (10 mL) was added NaH (936.84 mg, 23.42 mmol). Then to the mixture was added 5-bromo-2,3-difluoro-pyridine (4.54 g, 23.42 mmol), and the mixture was stirred at 80° C. for 16 hours. After cooled to r.t., the mixture was diluted with H₂O (10 mL) and extracted with EtOAc (10 mL×2). The combined organic phase was washed with brine (10 mL), dried over Na₂SO₄, filtered and concentrated to give the crude product. The crude product was purified by flash chromatography on silica gel (EtOAc in PE=0% to 2%) to give A-31b (2800 mg, 9.27 mmol, 40% yield) as colorless oil. ¹H NMR (400 MHz, CDCl₃) δ$_H$=7.99 (d, 1H), 7.54 (dd, 1H), 1.80 (d, 6H).

A mixture of 5-bromo-3-fluoro-2-(2,2,2-trifluoro-1,1-dimethyl-ethoxy)pyridine (1.5 g, 4.97 mmol), 4,4,5,5-tetramethyl-2-(4,4,5,5-tetramethyl-1,3,2-dioxaborolan-2-yl)-1,3,2-dioxaborolane (1.89 g, 7.45 mmol), Pd(dppf)Cl₂ (545.03 mg, 0.74 mmol) and KOAc (974.71 mg, 9.93 mmol) in 1,4-Dioxane (20 mL) was stirred at 90° C. for 16 hours to give a brown mixture. After cooling to r.t., the suspension was diluted with EtOAc (10 mL), filtered through silica gel, eluted with EtOAc (20 mL). The filtrate was concentrated to give the crude product. The crude product was purified by flash chromatography on silica gel (EtOAc in PE=0% to 10%) to give A-31d (1000 mg, 2.86 mmol, 58% yield) as an off-white solid. ¹H NMR (400 MHz, CDCl₃) δ$_H$=8.26 (d, 1H), 7.67 (dd, 1H), 1.83 (s, 6H), 1.34 (s, 12H).

A mixture of 3-fluoro-5-(4,4,5,5-tetramethyl-1,3-dioxolan-2-yl)-2-(2,2,2-trifluoro-1,1-dimethyl-ethoxy)pyridine (411.81 mg, 1.17 mmol), 5-chlorotriazolo[1,5-a]pyridine (150 mg, 0.98 mmol), Pd(t-Bu₃P)₂ (74.88 mg, 0.15 mmol) and K₃PO₄ (414.73 mg, 1.95 mmol) in 1,4-Dioxane (3 mL) and Water (0.30 mL) was stirred at 85° C. for 16 hours. After cooling to room temperature, the suspension was diluted with EtOAc (10 mL), filtered through silica gel, eluted with EtOAc (20 mL). The combined filtrates were concentrated to afford crude product. The crude product was purified by Prep-HPLC (Waters Xbridge (150 mm×25 mm, 5 μm) A=H₂O (10 mM NH₄HCO₃) and B=CH₃CN; 48-68% B over 7 minutes) to give the product (127.17 mg, 0.37 mmol, 38% yield) as a solid. ¹H NMR (400 MHz, CDCl₃) δ$_H$=8.83 (d, 1H), 8.23 (d, 1H), 8.15 (s, 1H), 7.85 (s, 1H), 7.66 (dd, 1H), 7.17 (dd, 1H), 1.88 (s, 6H). LCMS R$_t$=1.22 min in 2 min chromatography, 10-80AB, purity 100%, MS ESI calcd. for C₁₅H₁₃F₄N₄O [M+H]⁺ 341.1, found 340.9.

Example 25. Synthesis of Compound 25

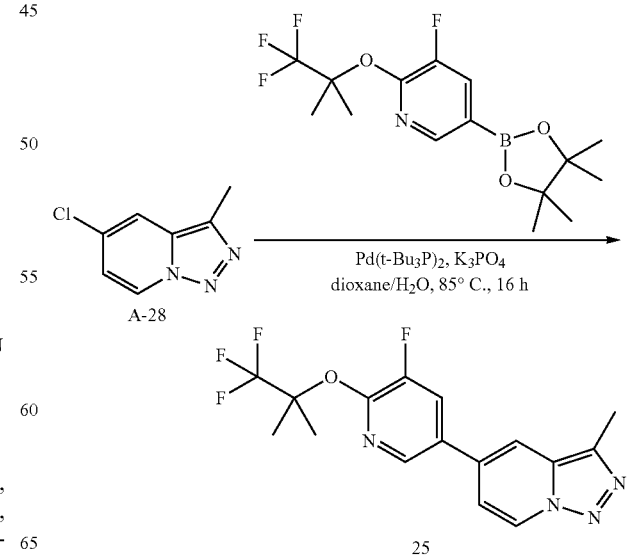

A mixture of 3-fluoro-5-(4,4,5,5-tetramethyl-1,3-dioxolan-2-yl)-2-(2,2,2-trifluoro-1,1-dimethyl-ethoxy)pyridine (262.04 mg, 0.75 mmol), 5-chloro-3-methyl-triazolo[1,5-a]pyridine (150 mg, 0.89 mmol), Pd(t-Bu₃P)₂ (68.61 mg, 0.13 mmol), and K₃PO₄ (380.01 mg, 1.79 mmol) in 1,4-Dioxane (2 mL) and Water (0.20 mL) was stirred at 85° C. for 16 hours. After cooling to room temperature, the suspension was diluted with EtOAc (10 mL), filtered through silica gel, eluted with EtOAc (15 mL). The combined filtrates were concentrated to afford crude product. The crude product was purified by Prep-HPLC (Xtimate C18 (150 mm×25 mm, 5 μm) A=H₂O (10 mM NH₄HCO₃) and B=CH₃CN; 54-70% B over 9 minutes) to give the product (92.98 mg, 0.26 mmol, 29% yield) as a solid. ¹H NMR (400 MHz, CDCl₃) $\delta_H$=8.73 (d, 1H), 8.24 (d, 1H), 7.72 (s, 1H), 7.67 (dd, 1H), 7.11 (d, 1H), 2.68 (s, 3H), 1.88 (s, 6H). LCMS $R_t$=1.33 min in 2 min chromatography, 10-80AB, purity 100%, MS ESI calcd. for $C_{16}H_{15}F_4N_4O$ [M+H]⁺ 355.1, found 355.0.

Example 26. Synthesis of Compound 26

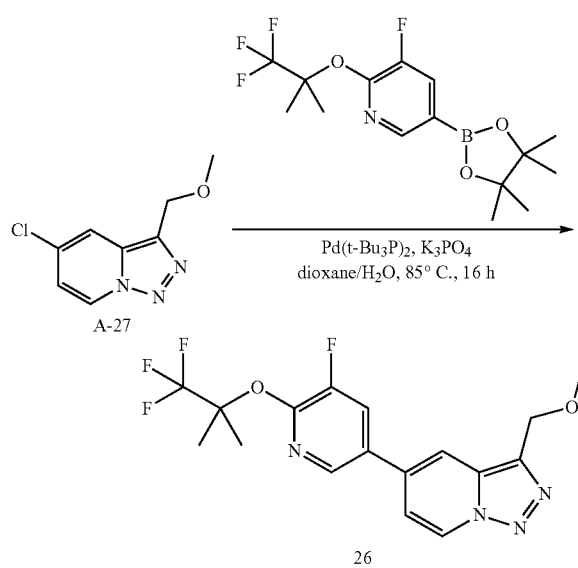

A mixture of 3-fluoro-5-(4,4,5,5-tetramethyl-1,3-dioxolan-2-yl)-2-(2,2,2-trifluoro-1,1-dimethyl-ethoxy)pyridine (149.34 mg, 0.43 mmol), 5-bromo-3-(methoxymethyl)triazolo[1,5-a]pyridine (85.74 mg, 0.35 mmol), Pd(t-Bu₃P)₂ (27.15 mg, 0.05 mmol), and K₃PO₄ (150.40 mg, 0.71 mmol) in 1,4-Dioxane (2 mL) and Water (0.20 mL) was stirred at 85° C. for 16 hours. After cooling to room temperature, the suspension was diluted with EtOAc (10 mL), filtered through silica gel, eluted with EtOAc (15 mL). The combined filtrates were concentrated to afford crude product. The crude product was purified by Prep-HPLC (Waters Xbridge (150 mm×25 mm, 5 μm) A=H₂O (10 mM NH₄HCO₃) and B=CH₃CN; 46-66% B over 9 minutes) to give the product of (50.31 mg, 0.13 mmol, 37% yield) as a solid. ¹H NMR (400 MHz, CDCl₃) $\delta_H$=8.78 (d, 1H), 8.25 (d, 1H), 7.93 (s, 1H), 7.68 (dd, 1H), 7.17 (dd, 1H), 4.96 (s, 2H), 3.47 (s, 3H), 1.88 (s, 6H). LCMS $R_t$=1.32 min in 2 min chromatography, 10-80AB, purity 100%, MS ESI calcd. for $C_{17}H_{17}F_4N_4O_2$ [M+H]⁺ 385.1, found 385.0.

Example 27. Synthesis of Compound 27

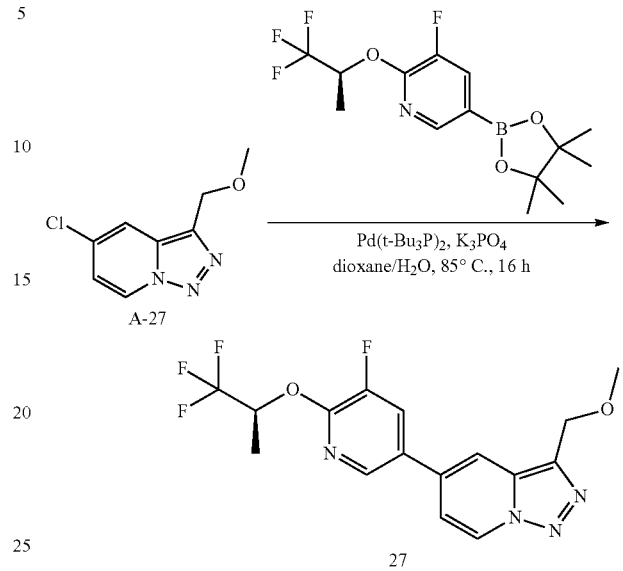

A mixture of 3-fluoro-5-(4,4,5,5-tetramethyl-1,3,2-dioxaborolan-2-yl)-2-[(1S)-2,2,2-trifluoro-1-methyl-ethoxy]pyridine (122.09 mg, 0.36 mmol), 5-chloro-3-(methoxymethyl)triazolo[1,5-a]pyridine (60 mg, 0.30 mmol), Pd(t-Bu₃P)₂ (23.27 mg, 0.05 mmol), and K₃PO₄ (128.91 mg, 0.61 mmol) in 1,4-Dioxane (2 mL) and Water (0.20 mL) was stirred at 85° C. for 16 hours. After cooling to room temperature, the suspension was diluted with EtOAc (10 mL), filtered through silica gel, eluted with EtOAc (20 mL). The combined filtrates were concentrated to afford crude product. The crude product was purified by purified by Prep-HPLC (Xtimate C18 (150 mm×25 mm, 5 μm) A=H₂O (10 mM NH₄HCO₃) and B=CH₃CN; 41-66% B over 9 minutes) to give the product (20.87 mg, 56.30 μmol, 19% yield) as a solid. ¹H NMR (400 MHz, CDCl₃+D₂O) $\delta_H$=8.79 (d, 1H), 8.24 (d, 1H), 7.94 (s, 1H), 7.78-7.65 (m, 1H), 7.18 (d, 1H), 6.03-5.75 (m, 1H), 4.96 (s, 2H), 3.47 (s, 3H), 1.60 (d, 3H). LCMS $R_t$=1.27 min in 2 min chromatography, 10-80AB, purity 100%, MS ESI calcd. for $C_{16}H_{15}F_4N_4O_2$ [M+H]⁺ 371.1, found 371.0.

Example 28. Synthesis of Compound 28

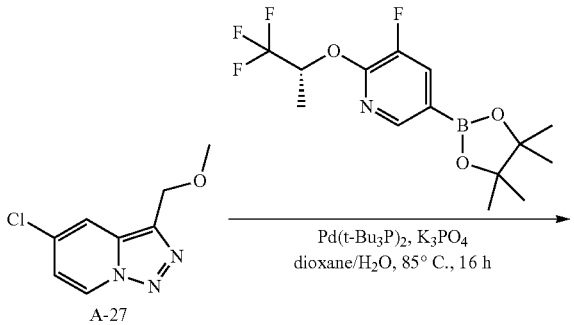

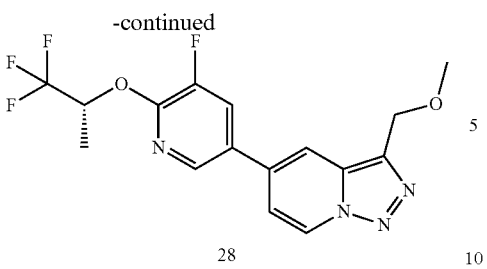

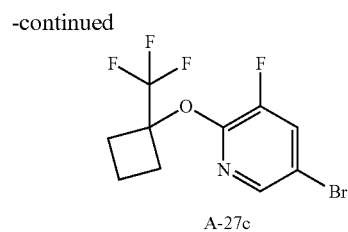

A mixture of 3-fluoro-5-(4,4,5,5-tetramethyl-1,3,2-dioxaborolan-2-yl)-2-[(1S)-2,2,2-trifluoro-1-methyl-ethoxy]pyridine (99.67 mg, 0.30 mmol), 5-bromo-3-(methoxymethyl)triazolo[1,5-a]pyridine (60 mg, 0.25 mmol), Pd(t-Bu$_3$P)$_2$ (19 mg, 0.04 mmol), and K$_3$PO$_4$ (105.24 mg, 0.50 mmol) in 1,4-Dioxane (2 mL) and Water (0.20 mL) was stirred at 85° C. for 16 hours. After cooling to room temperature, the suspension was diluted with EtOAc (10 mL), filtered through silica gel, eluted with EtOAc (20 mL). The combined filtrates were concentrated to afford crude product. The crude product was purified by purified by Prep-HPLC (Xtimate C18 (150 mm×25 mm, 5 μm) A=H$_2$O (10 mM NH$_4$HCO$_3$) and B=CH$_3$CN; 41-66% B over 9 minutes) to give the product (13.98 mg, 0.04 mmol, 15% yield) as a solid. $^1$H NMR (400 MHz, CDCl$_3$+D$_2$O) $\delta_H$=8.79 (d, 1H), 8.24 (d, 1H), 7.93 (s, 1H), 7.71 (dd, 1H), 7.18 (d, 1H), 5.98-5.79 (m, 1H), 4.96 (s, 2H), 3.47 (s, 3H), 1.60 (d, 3H). LCMS R$_t$=1.22 min in 2 min chromatography, 10-80AB, purity 100%, MS ESI calcd. for C$_{16}$H$_{15}$F$_4$N$_4$O$_2$ [M+H]$^+$ 371.1, found 371.0.

Example 29. Synthesis of Compound 29

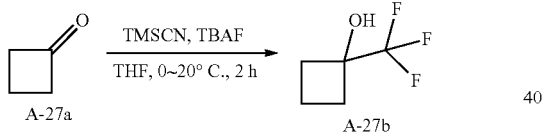

To a colorless mixture of cyclobutanone (500 mg, 7.13 mmol) and trimethyl(trifluoromethyl)silane (1.32 g, 9.27 mmol) in THF (10 mL) was added TBAF (0.07 mL, 0.07 mmol) at 0° C., then the mixture was stirred at 20° C. for 2 hours. The mixture was neutralized with 1M HCl (10 mL), then the mixture was stirred at 20° C. for 1 hours. Later on the mixture was extracted with DCM (30 mL×2). The combined organic phase was washed with water (10 mL) and brine (10 mL), dried over Na$_2$SO$_4$, filtered and concentrated to give the crude product A-27b (450 mg, 3.21 mmol, 45% yield) as oil. $^1$H NMR (400 MHz, DMSO-d$_6$) $\delta_H$=6.40 (s, 1H), 2.38-2.27 (m, 2H), 2.18-2.04 (m, 2H), 1.90-1.79 (m, 1H), 1.74-1.60 (m, 1H).

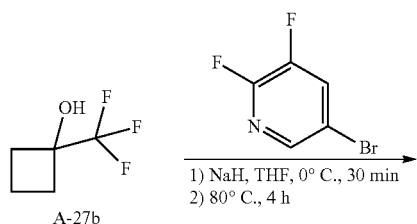

To a solution of 1-(trifluoromethyl)cyclobutanol (216.67 mg, 1.55 mmol) in THF (10 mL) was added NaH (61.86 mg, 1.55 mmol) at 0° C., and the mixture was stirred for 30 min. Then to the mixture was added 5-bromo-2,3-difluoro-pyridine (300 mg, 1.55 mmol), and the mixture was stirred at 80° C. for 4 hours. After cooling to r.t., the mixture was pour into ice water and stirred for 30 mins. Then the mixture was diluted with sat.NH$_4$Cl (20 mL) and extracted with EtOAc (50 mL×2). The combined organic phase was washed with brine (20 mL), dried over Na$_2$SO$_4$, filtered and concentrated to give the crude product A-27c. $^1$H NMR (400 MHz, DMSO-d$_6$) $\delta_H$=8.21 (dd, 1H), 8.16 (d, 1H), 2.88-2.76 (m, 2H), 2.65-2.56 (m, 2H), 1.97-1.88 (m, 1H), 1.87-1.76 (m, 11-1).

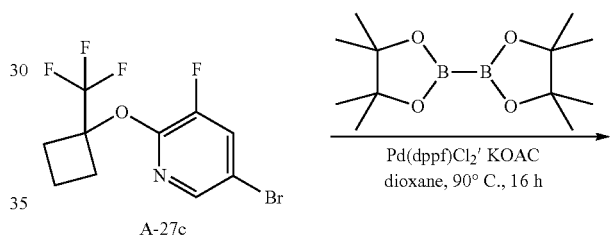

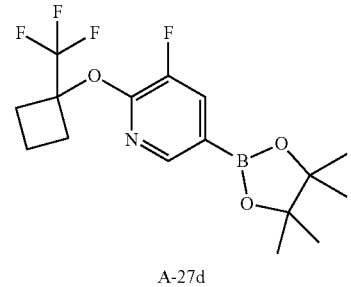

A brown mixture of 5-bromo-3-fluoro-2-[1-(trifluoromethyl)cyclobutoxy]pyridine (400 mg, 1.27 mmol), 4,4,5,5-tetramethyl-2-(4,4,5,5-tetramethyl-1,3,2-dioxaborolan-2-yl)-1,3,2-dioxaborolane (323.42 mg, 1.27 mmol), Pd(dppf)Cl$_2$ (139.78 mg, 0.19 mmol) and KOAc (249.98 mg, 2.55 mmol) in 1,4-Dioxane (20 mL) was stirred at 90° C. for 16 hours under N$_2$. The mixture was cooled to r.t. and concentrated. The residue was diluted with EtOAc/PE (1:10, 20 mL), filtered through silica gel, eluted with EtOAc/PE (1:10, 50 mL) and concentrated to give the crude product A-27d (500 mg, crude) as oil. $^1$H NMR (400 MHz, CDCl$_3$) $\delta_H$=8.27 (d, 1H), 7.68 (dd, 1H), 2.99-2.84 (m, 2H), 2.77-2.64 (m, 2H), 2.02-1.91 (m, 2H), 1.36-1.33 (m, 12H).

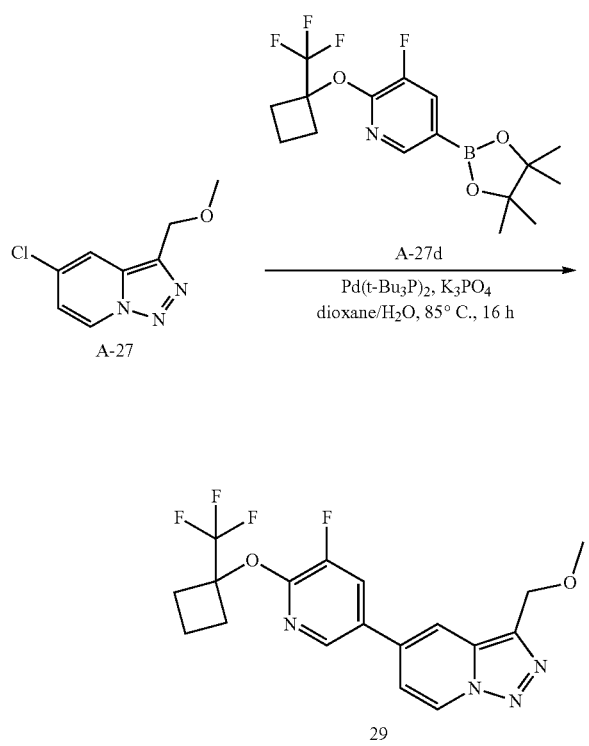

A mixture of 3-fluoro-5-(4,4,5,5-tetramethyl-1,3,2-dioxaborolan-2-yl)-2-[1-(trifluoromethyl)cyclobutoxy]pyridine (175.43 mg, 0.49 mmol), 5-chloro-3-(methoxymethyl)triazolo[1,5-a]pyridine (80 mg, 0.40 mmol), Pd(t-Bu$_3$P)$_2$ (31.03 mg, 0.06 mmol), and K$_3$PO$_4$ (171.89 mg, 0.81 mmol) in 1,4-Dioxane (4 mL) and Water (0.40 mL) was stirred at 85° C. for 16 hours. After cooling to room temperature, the suspension was diluted with EtOAc (10 mL), filtered through silica gel, eluted with EtOAc (20 mL). The combined filtrates were concentrated to afford crude product. The crude product was purified by Prep-HPLC (Xtimate C18 (150 mm×25 mm, 5 μm) A=H$_2$O (10 mM NH$_4$HCO$_3$) and B=CH$_3$CN; 48-78% B over 7 minutes) to give the product (32.94 mg, 0.08 mmol, 21% yield) as a solid. $^1$H NMR (400 MHz, CDCl$_3$) $\delta_H$=8.78 (dd, 1H), 8.26 (d, 1H), 7.94 (d, 1H), 7.68 (dd, 1H), 7.17 (dd, 1H), 4.95 (s, 2H), 3.47 (s, 3H), 2.99-2.86 (m, 2H), 2.81-2.71 (m, 2H), 2.10-1.92 (m, 2H). LCMS R$_t$=1.31 min in 2 min chromatography, 10-80AB, purity 100%, MS ESI calcd. for C$_{18}$H$_{17}$F$_4$N$_4$O$_2$ [M+H]$^+$ 397.1, found 397.1.

Example 30. Synthesis of Compound 30

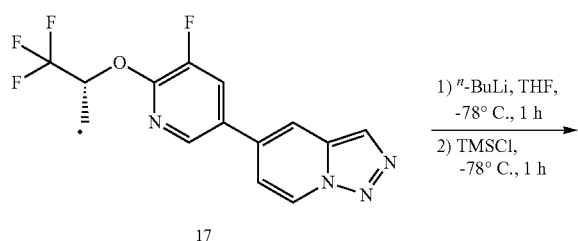

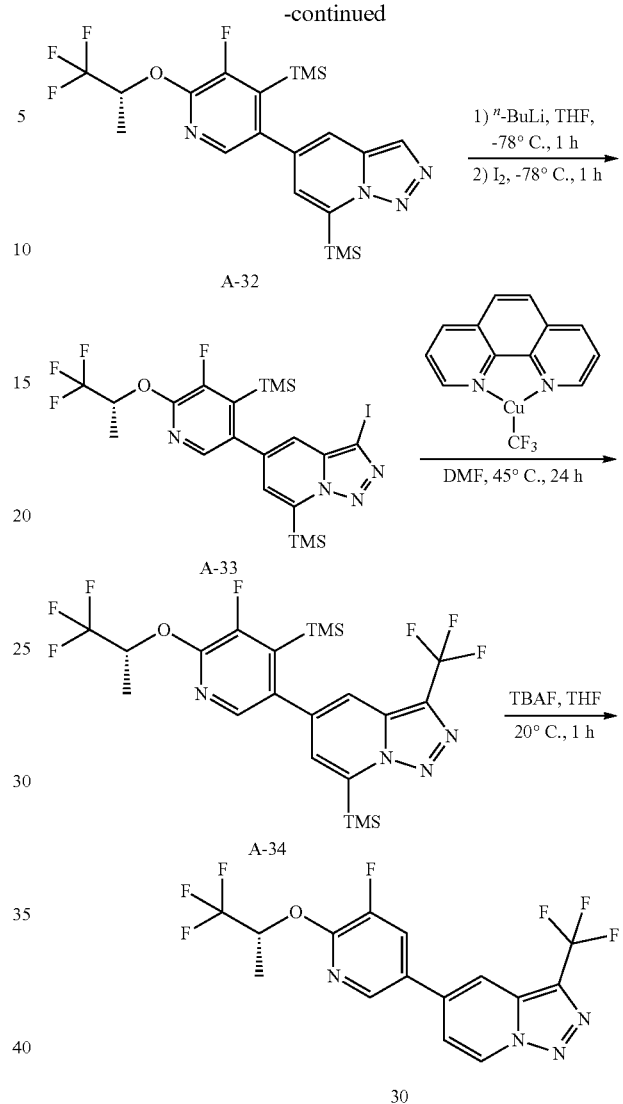

Synthesis of A-32: To a mixture of 5-[5-fluoro-6-[(1R)-2,2,2-trifluoro-1-methyl-ethoxy]-3-pyridyl]triazolo[1,5-a]pyridine (1.6 g, 4.9 mmol) in THF (70 mL) was added n-BuLi (4.9 mL, 12.26 mmol) at −78° C. under N$_2$, then the mixture was stirred at −78° C. for 1 hour. To the mixture was added chloro(trimethyl)silane (1.86 g, 17.16 mmol), then the mixture was stirred at −78° C. for 1 hour. The mixture was quenched with sat. NH$_4$Cl (100 mL), then the mixture was extracted with EtOAc (50 mL×2). The combined organic phase was washed with brine (20 mL), dried over Na$_2$SO$_4$, filtered and concentrated to give the crude product. The crude product was purified by silica gel column (EtOAc in PE=0% to 5% to 10%) to give the product (1120 mg, 2.30 mmol, 47% yield) as a solid. LCMS R$_t$=1.05 min in 1.5 min chromatography, 5-95AB, purity 96.60%, MS ESI calcd. for C$_{20}$H$_{27}$F$_4$N$_4$OSi$_2$ [M+H]$^+$ 471.2, found 471.2.

Synthesis of A-33: To a mixture of [5-[5-fluoro-6-[(1R)-2,2,2-trifluoro-1-methyl-ethoxy]-4-trimethylsilyl-3-pyridyl]triazolo[1,5-a]pyridin-7-yl]-trimethyl-silane (700 mg, 1.49 mmol) in THF (40 mL) was added n-BuLi (0.71 mL, 1.78 mmol) at −78° C. under N$_2$. Then the mixture was stirred at −78° C. for 1 hour. To the mixture was added I$_2$ (755.05 mg, 2.97 mmol), then the mixture was stirred at −78° C. for 1 hour. The mixture was quenched with sat. NH₄Cl (30 mL), then the mixture was extracted with EtOAc (50 mL×2). The combined organic phase was washed with brine (30 mL), dried over Na₂SO₄, filtered and concentrated to give the crude product. The crude product was purified by flash chromatography on silica gel (EtOAc in PE=0% to 2% to 5%) to give the product (430 mg, 0.50 mmol, 34% yield) as an oil. LCMS $R_t$=1.17 min in 1.5 min chromatography, 5-95AB, purity 69.42%, MS ESI calcd. for $C_{20}H_{26}F_4IN_4OSi_2$ [M+H]⁺ 597.1, found 597.1.

Synthesis of A-34: A mixture of 1,10-phenanthroline, triflnoromethy copper (225.46 mg, 0.72 mmol) and [3-fluoro-5-(3-iodo-7-trimethylsilyl-triazolo[1,5-a]pyridin-5-yl)-2-[(1R)-2,2,2-trifluoro-1-methyl-ethoxy]-4-pyridyl]-trimethyl-silane (430 mg, 0.72 mmol) in DMF (4.81 mL) was stirred at 45° C. for 24 hours in sealed tube under N₂. After cooling to room temperature, the mixture was diluted with H₂O (10 mL), and the mixture was extracted with EtOAc (20 mL×2). The combined organic phase was washed with water (10 mL×2) and brine (10 mL), dried over Na₂SO₄, filtered and concentrated to give the crude product. The crude product was purified by Prep-TLC (silica gel, PET/EtOAc=5/1) to give the impure product (200 mg, 0.37 mmol) as an oil, which was used directly without any further purification.

Synthesis of 30: To a mixture of [3-fluoro-2-[(1R)-2,2,2-trifluoro-1-methyl-ethoxy]-5-[3-(trifluoromethyl)-7-trimethylsilyl-triazolo[1,5-a]pyridin-5-yl]-4-pyridyl]-trimethyl-silane (200 mg, 0.37 mmol) in THF (20 mL) was added TBAF (1.86 mL, 1.86 mmol), then the mixture was stirred at 20° C. for 1 hour. The mixture was diluted with H₂O (20 mL), and the mixture was extracted with EtOAc (30 mL×2). The combined organic phase was washed with water (20 mL) and brine (20 mL), dried over Na₂SO₄, filtered and concentrated to give the crude product. The crude product was purified by Prep-TLC (silica gel, PE:EtOAc=4:1) to give the impure product, which was purified by Prep-HPLC [Boston Prime C18 (150 mm×30 mm, 5 μm), A=H₂O (0.05% NH₄OH) and B=CH₃CN; 64-94% B over 8 minutes] to give the product (13.78 mg, 34.2 μmol, 9% yield) as a solid. ¹H NMR (400 MHz, CDCl₃) $\delta_H$=8.90 (dd, 1H), 8.27 (d, 1H), 7.94 (s, 1H), 7.72 (dd, 1H), 7.32 (dd, 1H), 5.97-5.85 (m, 1H), 1.60 (d, 3H). LCMS $R_t$=2.10 min in 3.0 min chromatography, 30-90CD, purity 98.18%, MS ESI calcd. for $C_{15}H_{13}F_7N_4O$ [M+H]⁺ 395.1, found 395.1.

Example 31. Synthesis of Compound 31

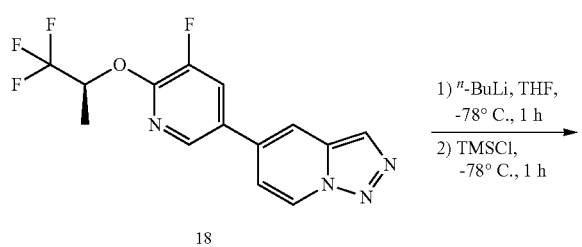

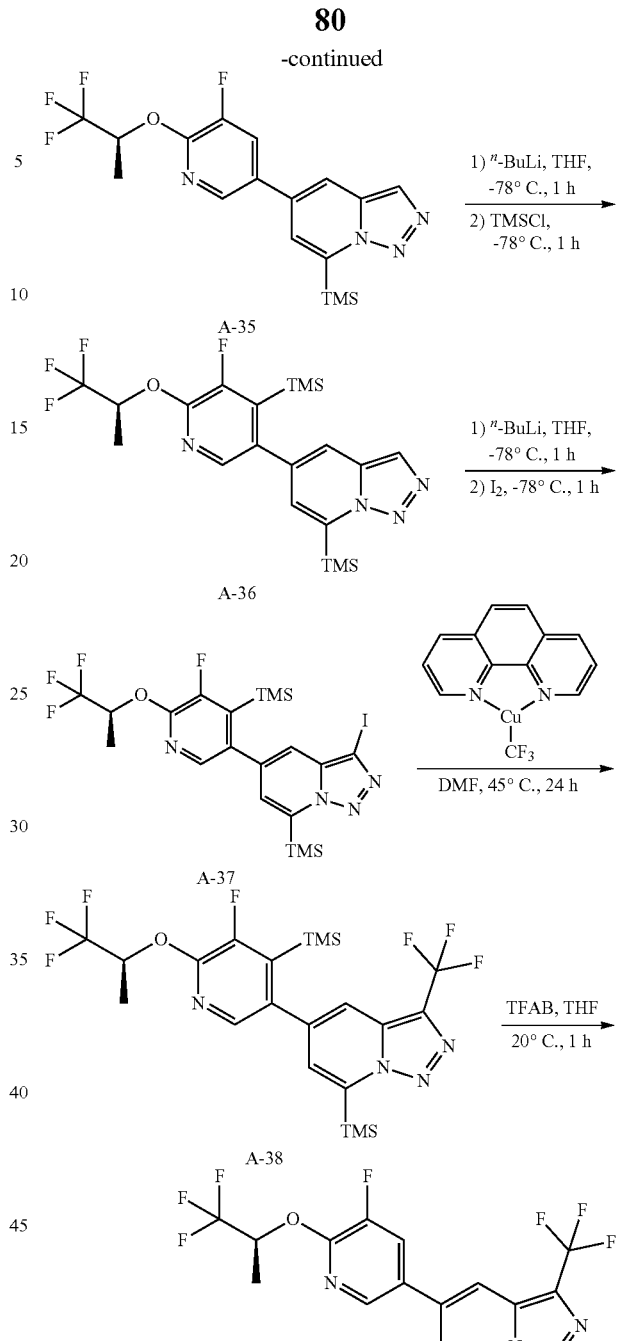

Synthesis of A-35: To a mixture of 5-[5-fluoro-6-[(1S)-2,2,2-trifluoro-1-methyl-ethoxy]-3-pyridyl]triazolo[1,5-a]pyridine (1.1 g, 3.37 mmol) in THF (40 mL) was added n-BuLi (3.37 mL, 8.43 mmol) at −78° C. under N₂, then the mixture was stirred at −78° C. for 2 hours. To the mixture was added chloro(trimethyl)silane (1.28 g, 11.8 mmol), then the mixture was stirred at −78° C. for 2 hours. The mixture was quenched with sat. NH₄Cl (100 mL), then the mixture was extracted with EtOAc (100 mL×2). The combined organic phase was washed with brine (50 mL), dried over Na₂SO₄, filtered and concentrated to give the crude product. The crude product was purified by silica gel column (EtOAc in PE=0% to 10% to 20%) to give the product (800 mg, 1.86 mmol, 55% yield) as a solid. LCMS $R_t$=0.95 min in 1.5 min chromatography, 5-95AB, purity 92.57%, MS ESI calcd. for $C_{17}H_{19}F_4N_4OSi$ [M+H]$^+$ 399.1, found 399.1.

Synthesis of A-36: To a mixture of [5-[5-fluoro-6-[(1S)-2,2,2-trifluoro-1-methyl-ethoxy]-3-pyridyl]triazolo[1,5-a]pyridin-7-yl]-trimethyl-silane (800 mg, 2.01 mmol) in THF (40 mL) was added n-BuLi (0.96 mL, 2.41 mmol) at −78° C. under N$_2$, then the mixture was stirred at −78° C. for 1 hour. To the mixture was added chloro(trimethyl)silane (654.41 mg, 6.02 mmol), then the mixture was stirred at −78° C. for 1 hour. The mixture was quenched with sat. NH$_4$Cl (30 mL), then the mixture was extracted with EtOAc (50 mL×2). The combined organic phase was washed with brine (30 mL), dried over Na$_2$SO$_4$, filtered and concentrated to give the crude product. The crude product was purified by silica gel column (EtOAc in PE=0% to 10% to 15%) to give the product (660 mg, 1.30 mmol, 65% yield) as a solid. LCMS $R_t$=1.04 min in 1.5 min chromatography, 5-95AB, purity 92.38%, MS ESI calcd. for $C_{20}H_{27}F_4N_4OSi_2$[M+H]$^+$ 471.2, found 471.2.

Synthesis of A-37: To a mixture of [5-[5-fluoro-6-[(1S)-2,2,2-trifluoro-1-methyl-ethoxy]-4-trimethylsilyl-3-pyridyl]triazolo[1,5-a]pyridin-7-yl]-trimethyl-silane (500 mg, 1.06 mmol) in THF (30 mL) was added n-BuLi (0.51 mL, 1.27 mmol) at −78° C. under N$_2$. Then the mixture was stirred at −78° C. for 1 hour. To the mixture was added I$_2$ (539.32 mg, 2.12 mmol), then the mixture was stirred at −78° C. for 1 hour. The mixture was quenched with sat. NH$_4$Cl (30 mL), then the mixture was extracted with EtOAc (50 mL×2). The combined organic phase was washed with brine (30 mL), dried over Na$_2$SO$_4$, filtered and concentrated to give the crude product. The crude product was purified by flash chromatography on silica gel (EtOAc in PE=0% to 2% to 5%) to give the product (320 mg, 0.36 mmol, 33% yield) as an oil. LCMS $R_t$=1.17 min in 1.5 min chromatography, 5-95AB, purity 66.24%, MS ESI calcd. for $C_{20}H_{26}F_4IN_4OSi_2$ [M+H]$^+$ 597.1, found 597.1.

Synthesis of A-38: A mixture of 1,10-phenanthroline, triflnoromethy copper (167.78 mg, 0.54 mmol) and [3-fluoro-5-(3-iodo-7-trimethylsilyl-triazolo[1,5-a]pyridin-5-yl)-2-[(1S)-2,2,2-trifluoro-1-methyl-ethoxy]-4-pyridyl]-trimethyl-silane (320 mg, 0.54 mmol) in DMF (3.58 mL) was stirred at 45° C. for 24 hours in 20 m L sealed tube under N$_2$. After cooling to room temperature, the mixture was diluted with H$_2$O (10 mL), and the mixture was extracted with EtOAc (20 mL×2). The combined organic phase was washed with water (10 mL×2) and brine (10 mL), dried over Na$_2$SO$_4$, filtered and concentrated to give the crude product. The crude product was purified by Prep-TLC (PE/EtOAc=5/1) to give the product (130 mg, 0.24 mmol, 45% yield) as an oil, which was used directly without any further purification.

Synthesis of 31: To a mixture of [3-fluoro-2-[(1S)-2,2,2-trifluoro-1-methyl-ethoxy]-5-[3-(trifluoromethyl)-7-trimethylsilyl-triazolo[1,5-a]pyridin-5-yl]-4-pyridyl]-trimethyl-silane (130 mg, 0.24 mmol) in THF (20 mL) was added TBAF (1.21 mL, 1.21 mmol), then the mixture was stirred at 20° C. for 1 hour. The mixture was diluted with H$_2$O (20 mL), and the mixture was extracted with EtOAc (30 mL×2). The combined organic phase was washed with water (20 mL) and brine (20 mL), dried over Na$_e$ SO$_4$, filtered and concentrated to give the crude product. The crude product was purified by Prep-TLC (silica gel, PE:EtOAc=4:1) to give the impure product. The impure product was purified by Prep-HPLC [Boston Prime C18 (150 mm×30 mm, 5 µm) A=H$_2$O (0.05% NH$_4$OH) and B=CH$_3$CN; 64-94% B over 8 minutes] to give the product (2.84 mg, 7.1 µmol, 3% yield) as a solid. $^1$H NMR (400 MHz, CDCl$_3$) $\delta_H$=8.90 (d, 1H), 8.27 (d, 1H), 7.94 (s, 1H), 7.72 (dd, 1H), 7.32 (dd, 1H), 5.97-5.85 (m, 1H), 1.60 (d, 3H). LCMS $R_t$=2.10 min in 3.0 min chromatography, 30-90CD, purity 100%, MS ESI calcd. for $C_{15}H_{10}F_7N_4O$ [M+H]$^+$ 395.1, found 395.0.

Example 32. Synthesis of Compound 32

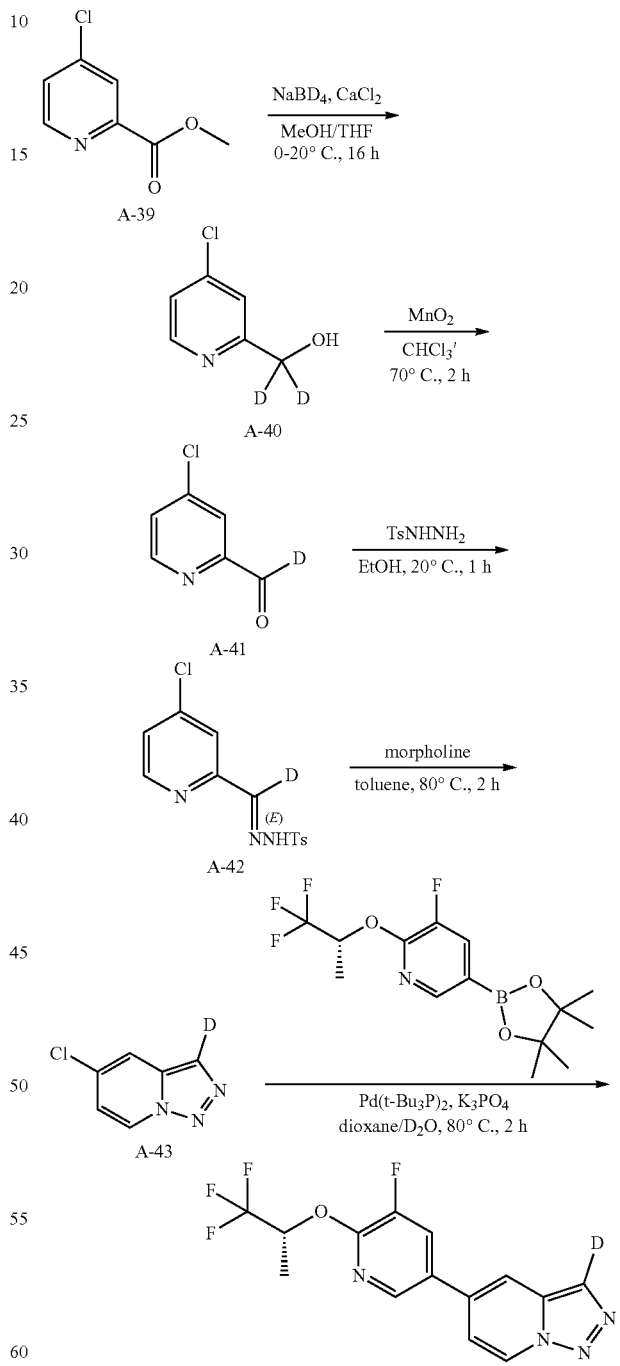

To a mixture of methyl 4-chloropyridine-2-carboxylate (10 g, 58.28 mmol) and CaCl$_2$ (25.87 g, 233.13 mmol) in Methanol (100 mL) and THF (50 mL) was added NaBD$_4$ (6.1 g, 145.7 mmol) at 0° C., then the mixture was stirred at 20° C. for 16 hours. The mixture was quenched with sat. NH₄Cl (50 mL), the mixture was extracted with EtOAc (100 mL×3). The combined organic phase was washed with brine (50 mL), dried over Na₂SO₄, filtered and concentrated to give the crude product. The crude product was purified by flash chromatography on silica gel (EtOAc in PE=0% to 35% to 70%) to give the product (6500 mg, 44.394 mmol) as oil. ¹H NMR (400 MHz, DMSO-d₆) 400 MHz $\delta_H$=8.45 (d, 1H), 7.50 (d, 1H), 7.39 (dd, 1H), 5.60-5.47 (m, 1H). LCMS $R_t$=0.13 min in 1.5 min chromatography, 5-95AB, purity 99.43%, MS ESI calcd. for C₆H₅D₂ClNO [M+H]⁺ 146.0, found 145.8.

To a mixture of (4-chloro-2-pyridyl)-dideuterio-methanol (6.5 g, 44.65 mmol) in Chloroform (150 mL) was added MnO₂ (58.23 g, 669.73 mmol), then the mixture was stirred at 70° C. for 2 hours. The mixture was filtered through Celite, eluted with CHCl₃ (100 mL×2), the filtrate was concentrated give the product (3700 mg, 25.95 mmol) as a solid. ¹H NMR (400 MHZ, DMSO-d₆) $\delta_H$=8.80 (d, 1H), 7.97 (d, 1H), 7.87 (dd, 1H).

A mixture of (4-chloro-2-pyridyl)-deuterio-methanone (3.65 g, 25.6 mmol) and 4-methylbenzenesulfonohydrazide (4.77 g, 25.6 mmol) in Ethanol (30 mL) was stirred at 20° C. for 1 hour. The solid was collected by filtration, then washed with EtOH (5 mL), dried in oven to give the product (6700 mg, 20.89 mmol) as a solid. ¹H NMR (400 MHz, DMSO-d₆) $\delta_H$=11.97 (s, 1H), 8.53 (d, 1H), 7.78 (d, 2H), 7.71 (d, 1H), 7.54 (dd, 1H), 7.43 (d, 2H), 2.37 (s, 3H). LCMS $R_t$=0.77 min in 1.5 min chromatography, 5-95AB, purity 96.89%, MS ESI calcd. for C₁₃H₁₂DClN₃O₂S [M+H]⁺ 311.0, found 311.0.

A mixture of N-[[(4-chloro-2-pyridyl)-deuterio-methylene]amino]-4-methyl-benzenesulfonamide (1 g, 3.22 mmol) and morpholine (0.56 mL, 6.44 mmol) in Toluene (40 mL) was stirred at 80° C. for 2 hours. After cooling to room temperature, the mixture was washed with water (20 mL×2) and brine (20 mL), dried over Na₂SO₄, filtered and concentrated to give the crude product. The crude product was purified by flash chromatography on silica gel (EtOAc in PE=0% to 40% to 70%) to give the product (460 mg, 2.94 mmol) as a solid. ¹H NMR (400 MHz, DMSO-d₆) $\delta_H$=8.68 (dd, 1H), 7.74 (dd, 1H), 6.96 (dd, 1H). LCMS $R_t$=0.66 min in 1.5 min chromatography, 5-95AB, purity 98.86%, MS ESI calcd. for C₆H₄DClN₃ [M+H]⁺ 155.0, found 154.8.

A mixture of 5-chloro-3-deuterio-triazolo[1,5-a]pyridine (80 mg, 0.51 mmol), 3-fluoro-5-(4,4,5,5-tetramethyl-1,3,2-dioxaborolan-2-yl)-2-[(1R)-2,2,2-trifluoro-1-methyl-ethoxy]pyridine (232.26 mg, 0.56 mmol), Pd(t-Bu₃P)₂ (39.22 mg, 80.0 μmol) and K₃PO₄ (217.24 mg, 1.02 mmol) in 1,4-Dioxane (5 mL) and D₂O (1 mL) was stirred at 80° C. for 2 hours under N₂. After cooling to room temperature, the mixture was diluted with H₂O (10 mL), and the mixture was extracted with EtOAc (20 mL×2). The combined organic phase was washed with water (10 mL) and brine (10 mL), dried over Na₂SO₄, filtered and concentrated to give the crude product. The crude product was purified by Prep-TLC (silica gel, PE:EtOAc=2:1) to give the product (71.64 mg, 217.1 μmol) as a solid. ¹H NMR (400 MHz, DMSO-d₆) $\delta_H$=9.20 (dd, 1H), 8.57 (d, 1H), 8.47-8.33 (m, 2H), 7.61 (dd, 1H), 6.09-5.95 (m, 1H), 1.54 (d, 3H). LCMS $R_t$=1.25 min in 2.0 min chromatography, 10-80AB, purity 99.49%, MS ESI calcd. for C₁₄H₁₀DF₁₀N₄O [M+H]⁺ 328.1, found 327.9. ESI calcd. for C₁₄H₁₀DF₄N₄O [M+H]⁺ 328.0926, found 328.0882.

Example 33. Synthesis of Compound 33

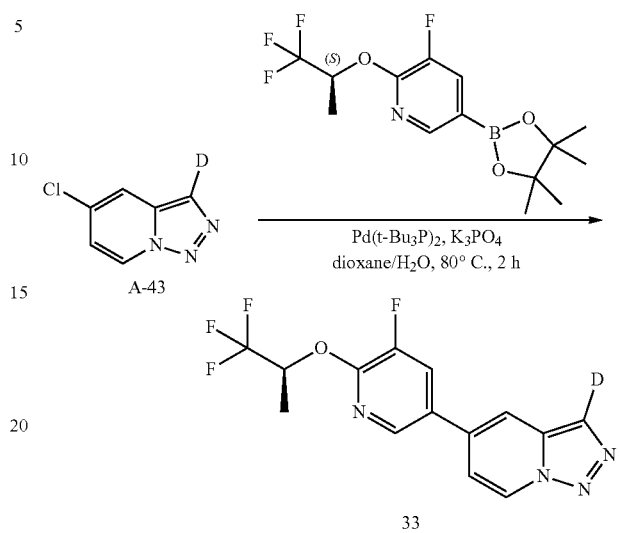

A mixture of 5-chloro-3-deuterio-triazolo[1,5-a]pyridine (80 mg, 0.51 mmol), 3-fluoro-5-(4,4,5,5-tetramethyl-1,3,2-dioxaborolan-2-yl)-2-[(1S)-2,2,2-trifluoro-1-methyl-ethoxy]pyridine (188.59 mg, 0.56 mmol), Pd(t-Bu₃P)₂ (39.22 mg, 80.0 mol) and K₃PO₄ (217.24 mg, 1.02 mmol) in 1,4-Dioxane (5 mL) and D₂O (1 mL) was stirred at 80° C. for 2 hours under N₂. After cooling to room temperature, the mixture was diluted with H₂O (10 mL), and the mixture was extracted with EtOAc (20 mL×2). The combined organic phase was washed with water (10 mL) and brine (10 mL), dried over Na₂SO₄, filtered and concentrated to give the crude product. The crude product was purified by Prep-TLC (silica gel, PE:EtOAc=2:1) to give the product (79.72 mg, 241.5 μmop) as a solid. ¹H NMR (400 MHz, DMSO-d₆) $\delta_H$=9.20 (dd, 1H), 8.57 (d, 1H), 8.47-8.33 (m, 2H), 7.61 (dd, 1H), 6.09-5.95 (m, 1H), 1.54 (d, 3H). LCMS $R_t$=1.24 min in 2.0 min chromatography, 10-80AB, purity 100%, MS ESI calcd. for C₁₄H₁₀DF₄N₄O [M+H]⁺ 328.1, found 327.9. MS ESI calcd. for C₁₄H₁₀DF₄N₄O [M+H]⁺ 328.0926, found 328.0881.

Example 34. Synthesis of Compound 34

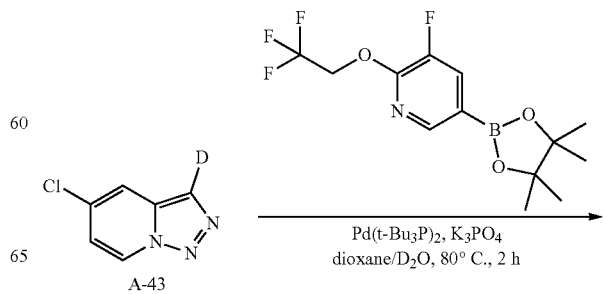

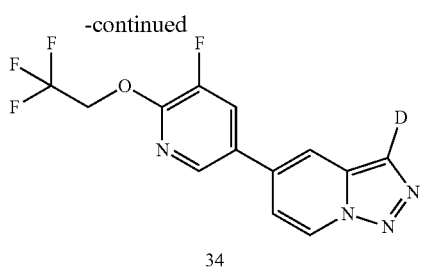

34

A mixture of 5-chloro-3-deuterio-triazolo[1,5-a]pyridine (70 mg, 0.45 mmol), 3-fluoro-5-(4,4,5,5-tetramethyl-1,3,2-dioxaborolan-2-yl)-2-(2,2,2-trifluoroethoxy)pyridine (158.11 mg, 0.49 mmol), Pd(t-Bu$_3$P)$_2$ (34.32 mg, 0.07 mmol) and K$_3$PO$_4$ (190.08 mg, 0.90 mmol) in 1,4-Dioxane (5 mL) and D$_2$O (0.88 mL, 43.68 mmol) was stirred at 80° C. for 2 hours under N$_2$. After cooling to room temperature, the mixture was filtered through Celite, and eluted with EtOAc (10 mL×2), and the filtrate was concentrated to give the crude product. The crude product was purified by Prep-HPLC (Waters Xbridge 150 mm×25 mm 5 μm) A=H$_2$O (10 mM NH$_4$HCO$_3$) and B=CH$_3$CN; 40-60% B over 7 minutes) to give the product (74.05 mg, 0.24 mmol) as a solid. $^1$H NMR (400 MHz, DMSO-d$_6$) δ$_H$=9.20 (d, 1H), 8.59 (d, 1H), 8.44-8.36 (m, 2H), 7.62 (dd, 1H), 5.17 (q, 2H). LCMS R$_t$=1.17 min in 2.0 min chromatography, 10-80AB, purity 100%, MS ESI calcd. for C$_{13}$H$_8$DF$_4$N$_4$O [M+H]$^+$ 314.1, found 313.9.

Example 35. Synthesis of Compound 35

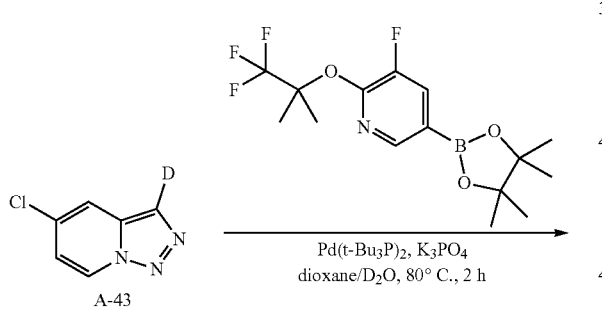

35

A mixture of 5-chloro-3-deuterio-triazolo[1,5-a]pyridine (70 mg, 0.45 mmol), 3-fluoro-5-(4,4,5,5-tetramethyl-1,3,2-dioxaborolan-2-yl)-2-(2,2,2-trifluoro-1,1-dimethyl-ethoxy)pyridine (171.93 mg, 0.49 mmol), Pd(t-Bu$_3$P)$_2$ (34.32 mg, 0.07 mmol) and K$_3$PO$_4$ (190.08 mg, 0.90 mmol) in 1,4-Dioxane (5 mL) and D$_2$O (0.88 mL, 43.68 mmol) was stirred at 80° C. for 2 hours under N$_2$. After cooling to room temperature, the mixture was diluted with H$_2$O (10 mL), and the mixture was extracted with EtOAc (20 mL×2). The organic phase was washed with brine (30 mL), dried over Na$_2$SO$_4$, filtered and concentrated to give the crude product. The crude product was purified by Prep-HPLC (Boston Prime C18 (150×30 mm, 5 μm), A=H$_2$O (0.05% NH$_4$OH) and B=CH$_3$CN; 53-83% B over 8 minutes) to give the product (43.05 mg, 126.1 μmol) as a solid $^1$H NMR (400 MHz, DMSO-d$_6$) δ$_H$=9.19 (d, 1H), 8.60-8.54 (m, 1H), 8.40-8.33 (m, 2H), 7.64-7.58 (m, 1H), 1.82 (s, 6H). LCMS R$_t$=1.30 min in 2.0 min chromatography, 10-80AB, purity 99.41%, MS ESI calcd. for C$_{15}$H$_{12}$DF$_4$N$_4$O [M+H]$^+$ 342.1, found 341.9.

Example 36. Synthesis of Compound 36

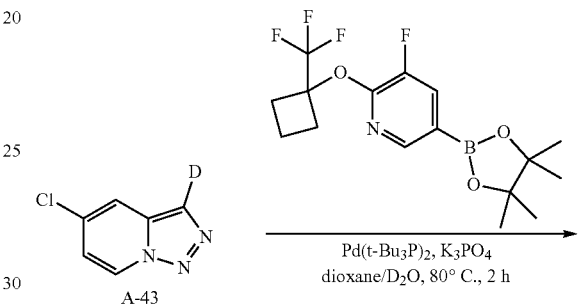

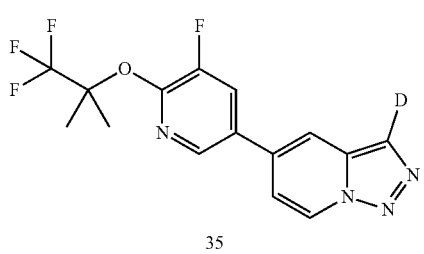

36

A mixture of 5-chloro-3-deuterio-triazolo[1,5-a]pyridine (100 mg, 0.65 mmol), 3-fluoro-5-(4,4,5,5-tetramethyl-1,3,2-dioxaborolan-2-yl)-2-[1-(trifluoromethyl)cyclobutoxy]pyridine (303.71 mg, 0.84 mmol), Pd(t-Bu$_3$P)$_2$ (49.59 mg, 0.10 mmol) and K$_3$PO$_4$ (274.68 mg, 1.29 mmol) in 1,4-Dioxane (5 mL) and D$_2$O (1 mL) was stirred at 80° C. for 2 hours under N$_2$. After cooling to room temperature, the mixture was diluted with H$_2$O (10 mL), and the mixture was extracted with EtOAc (20 mL×2). The combined organic phase was washed with water (10 mL) and brine (10 mL), dried over Na$_2$SO$_4$, filtered and concentrated to give the crude product. The crude product was purified by Prep-TLC (silica gel, PE:EtOAc=2:1) to give the product (33.79 mg, 94.7 μmol) as a solid. $^1$H NMR (400 MHz, DMSO-d$_6$) δ$_H$=9.18 (d, 1H), 8.56 (d, 1H), 8.42-8.32 (m, 2H), 7.61 (dd, 1H), 2.96-2.82 (m, 2H), 2.72-2.61 (m, 2H), 2.06-1.79 (m, 2H). LCMS R$_t$=1.32 min in 2.0 min chromatography, 10-80AB, purity 100%, MS ESI calcd. for C$_{16}$H$_{12}$DF$_4$N$_4$O [M+H]$^+$ 354.1, found 353.9. MS ESI calcd. for C$_{16}$H$_{12}$DF$_4$N$_4$O [M+H]$^+$ 354.1083, found 354.1093.

Example 37. Synthesis of Compound 37

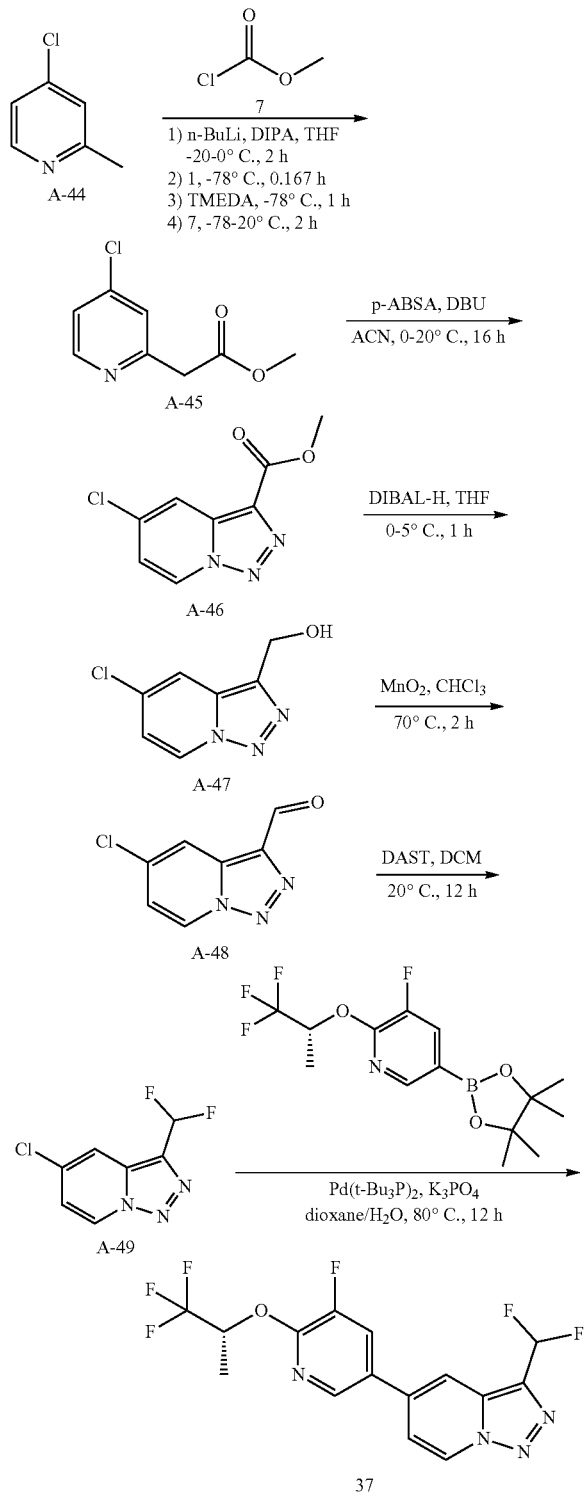

To a mixture of DIPA (6.35 g, 62.71 mmol) in THF (150 mL) was added n-BuLi (27.59 mL, 68.98 mmol) at −20° C., then the mixture was stirred at −20-0° C. for 2 hours. To the mixture was added 4-chloro-2-methyl-pyridine (4 g, 31.36 mmol) at −78° C., after 10 minutes, to the mixture was added TMEDA (7.29 g, 62.71 mmol). Then the mixture was stirred at −78° C. for 1 hour. To the mixture was added methyl carbonochloridate (6.3 g, 66.67 mmol), then the mixture was stirred at −78° C. to 20° C. for 2 hours. The mixture was quenched with sat. NH$_4$Cl (100 mL), then the mixture was extracted with EtOAc (100 mL×2). The combined organic phase was washed with water (50 mL) and brine (50 mL), dried over Na$_2$SO$_4$, filtered and concentrated to give the crude product. The crude product was purified by flash chromatography on silica gel (EtOAc in PE=0% to 15% to 30%) to give the product (4300 mg, 11.35 mmol) as an oil. LCMS R$_t$=0.58 min in 1.5 min chromatography, 5-95AB, purity 49.00%, MS ESI calcd. for C$_8$H$_9$ClNO$_2$ [M+H]$^+$ 186.0, found 186.0.

To a mixture of methyl 2-(4-chloro-2-pyridyl)acetate (5.2 g, 28.02 mmol) and p-ABSA (7.4 g, 30.82 mmol) in MeCN (130 mL) was added DBU (4.69 g, 30.82 mmol) at 0° C., then the mixture was stirred at 20° C. for 16 hours. The mixture was quenched with sat. NH$_4$Cl (100 mL), and the mixture was extracted with EtOAc (100 mL×2). The combined organic phase was washed with water (50 mL×2) and brine (50 mL), dried over Na$_2$SO$_4$, filtered and concentrated to give the crude product. The crude product was purified by flash chromatography on silica gel (EtOAc in PE=0% to 20% to 35%) to give the impure product, which was triturated from EtOAc/PET (20 mL/20 mL) and dried in an oven to give the product (2720 mg, 12.45 mmol) as a solid. $^1$H NMR (400 MHz, CDCl$_3$) δ$_H$=8.76 (d, 1H), 8.29 (d, 1H), 7.13 (dd, 1H), 4.06 (s, 3H). LCMS R$_t$=0.71 min in 1.5 min chromatography, 5-95AB, purity 96.87%, MS ESI calcd. for C$_8$H$_7$ClN$_3$O$_2$ [M+H]$^+$ 212.0, found 212.0.

To the mixture of methyl 5-chlorotriazolo[1,5-a]pyridine-3-carboxylate (2.2 g, 10.4 mmol) in THF (150 mL) was added DIBAL-H (26 mL, 26.00 mmol) at 0° C., then the mixture was stirred at 5° C. for 1 hour. To the mixture was added saturated solution of potassium sodium tartrate (~100 mL) and EtOAc (100 mL), and the mixture was stirred at 20° C. for 1 hour. After separation, the aqueous phase was extracted with EtOAc (100 mL). The combined organic phase was washed with brine (50 mL×2), dried over Na$_2$SO$_4$, filtered and concentrated to give the product (1800 mg, 9.70 mmol) as a solid. $^1$H NMR (400 MHz, CDCl$_3$) δ$_H$=8.64 (d, 1H), 7.87 (d, 1H), 6.97 (dd, 1H), 5.10 (d, 2H), 2.15 (t, 1H). LCMS R$_t$=0.51 min in 1.5 min chromatography, 5-95AB, purity 98.96%, MS ESI calcd. for C$_7$H$_7$ClN$_3$O [M+H]$^+$ 184.0, found 184.0.

To a mixture of (5-chlorotriazolo[1,5-a]pyridin-3-yl)methanol (1.3 g, 7.08 mmol) in Chloroform (100 mL) was add MnO$_2$ (9.23 g, 106.21 mmol), then the mixture was stirred at 70° C. for 2 hours. The mixture was filtered through Celite, eluted with CHCl$_3$ (50 mL×2), the filtrate was concentrated to give the crude product (1150 mg, 6.07 mmol, 86% yield, 95.90% purity) as a solid. $^1$H NMR (400 MHz, CDCl$_3$) δ$_H$=10.34 (s, 1H), 8.80 (d, 1H), 8.39 (d, 1H), 7.21 (dd, 1H). LCMS R$_t$=0.64 min in 1.5 min chromatography, 5-95AB, purity 95.90%, MS ESI calcd. for C$_7$H$_5$ClN$_3$O [M+H]$^+$ 182.0, found 182.0.

To a mixture of 5-chlorotriazolo[1,5-a]pyridine-3-carbaldehyde (500 mg, 2.75 mmol) in DCM (30 mL) was added DAST (1.83 mL, 13.77 mmol), then the mixture was stirred at 20° C. for 12 hours. The mixture was poured into ice-water (30 mL) and the mixture was basified with NaHCO$_3$ (solid) to pH~9 and extracted with EtOAc (50 mL×2). The combined organic phase was washed with water (30 mL×2) and brine (30 mL), dried over Na$_2$SO$_4$, filtered and concentrated to give the crude product. The crude product was purified by flash chromatography on silica gel (EtOAc in PE=0% to 10% to 20%) to give the product (500 mg, 2.38 mmol) as a solid. $^1$H NMR (400 MHz, DMSO-d$_6$) $\delta_H$=9.27 (dd, 1H), 8.24 (d, 1H), 7.71-7.37 (m, 2H). LCMS R$_t$=0.76 min in 1.5 min chromatography, 5-95AB, purity 97.00%, MS ESI calcd. for C$_7$H$_5$ClF$_2$N$_3$ [M+H]$^+$ 204.0, found 204.0.

A mixture of 5-chloro-3-(difluoromethyl)triazolo[1,5-a]pyridine (70 mg, 0.34 mmol), 3-fluoro-5-(4,4,5,5-tetramethyl-1,3,2-dioxaborolan-2-yl)-2-[(1R)-2,2,2-trifluoro-1-methyl-ethoxy]pyridine (138.27 mg, 0.41 mmol), Pd(t-Bu$_3$P)$_2$ (26.36 mg, 50.0 μmol) and K$_3$PO$_4$ (146 mg, 0.69 mmol) in 1,4-Dioxane (5 mL) and Water (0.70 mL) was stirred 80° C. for 12 hours under N$_2$. After cooling to room temperature, the mixture was diluted with H$_2$O (10 mL), and the mixture was extracted with EtOAc (20 mL×2). The combined organic phase was washed with water (10 mL) and brine (10 mL), dried over Na$_2$SO$_4$, filtered and concentrated to give the crude product. The crude product was purified by Prep-TLC (silica gel, PE:EtOAc=5:1) to give the impure product, which was triturated from i-Pr$_2$O/Hexane (1 mL/2 mL) to give the product (37.39 mg, 99.2 μmol) as a solid. $^1$H NMR (400 MHz, DMSO-d$_6$) $\delta_H$=9.34 (d, 1H), 8.62 (d, 1H), 8.48 (dd, 1H), 8.43 (s, 1H), 7.77 (dd, 1H), 7.57 (t, 1H), 6.11-5.98 (m, 1H), 1.54 (d, 3H).

LCMS R$_t$=1.32 min in 2.0 min chromatography, 10-80AB, purity 100%, MS ESI calcd. for C$_{15}$H$_{11}$F$_6$N$_4$O [M+H]$^+$ 377.1, found 376.9.

Example 38. Synthesis of Compound 38

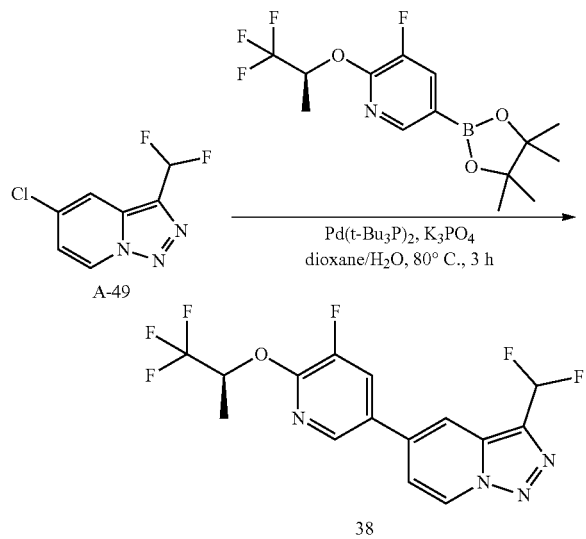

A mixture of 5-chloro-3-(difluoromethyl)triazolo[1,5-a]pyridine (70 mg, 0.34 mmol), 3-fluoro-5-(4,4,5,5-tetramethyl-1,3,2-dioxaborolan-2-yl)-2-[(1S)-2,2,2-trifluoro-1-methyl-ethoxy]pyridine (149.79 mg, 0.45 mmol), Pd(t-Bu$_3$P)$_2$ (26.36 mg, 50.0 μmol) and K$_3$PO$_4$ (146 mg, 0.69 mmol) in 1,4-Dioxane (5 mL) and Water (0.70 mL) was stirred 80° C. for 3 hours under N$_2$. After cooling to room temperature, the mixture was diluted with H$_2$O (10 mL), and the mixture was extracted with EtOAc (20 mL×2). The combined organic phase was washed with water (10 mL) and brine (10 mL), dried over Na$_2$SO$_4$, filtered and concentrated to give the crude product. The crude product was purified by Prep-TLC (silica gel, PE:EtOAc=5:1) to give the impure product, which was triturated from i-Pr$_2$O/Hexane (2 mL/2 mL) to give the product (50.28 mg, 133.3 μmop as a solid. $^1$H NMR (400 MHz, DMSO-d$_6$) O$_H$=9.34 (d, 1H), 8.62 (d, 1H), 8.48 (dd, 1H), 8.43 (s, 1H), 7.77 (dd, 1H), 7.57 (t, 1H), 6.10-5.98 (m, 1H), 1.54 (d, 3H). LCMS R$_t$=1.32 min in 2.0 min chromatography, 10-80AB, purity 100%, MS ESI calcd. for C$_5$H$_{11}$F$_6$N$_4$O [M+H]$^+$ 377.1, found 376.9.

Example 39. Synthesis of Compound 39

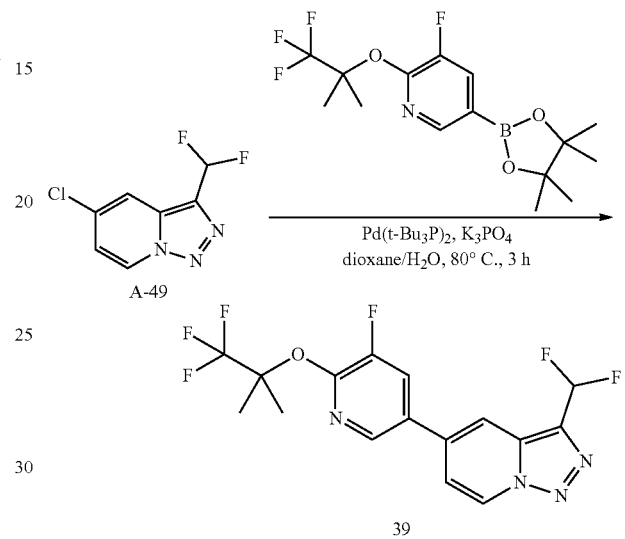

A mixture of 5-chloro-3-(difluoromethyl)triazolo[1,5-a]pyridine (70 mg, 0.34 mmol), 3-fluoro-5-(4,4,5,5-tetramethyl-1,3,2-dioxaborolan-2-yl)-2-(2,2,2-trifluoro-1,1-dimethyl-ethoxy)pyridine (156.06 mg, 0.45 mmol), Pd(t-Bu$_3$P)$_2$ (26.36 mg, 50.0 μmol) and K$_3$PO$_4$ (146 mg, 0.69 mmol) in 1,4-Dioxane (5 mL) and Water (0.70 mL) was stirred 80° C. for 3 hours under N$_2$. After cooling to room temperature, the mixture was diluted with H$_2$O (10 mL), and the mixture was extracted with EtOAc (20 mL×2). The combined organic phase was washed with water (10 mL) and brine (10 mL), dried over Na$_2$SO$_4$, filtered and concentrated to give the crude product. The crude product was purified by Prep-TLC (silica gel, PE:EtOAc=4:1) to give the impure product, which was triturated from i-Pr$_2$O/Hexane (3 mL/1 mL) to give the product (46.99 mg, 119.8 μmol) as a solid. $^1$H NMR (400 MHz, DMSO-d$_6$) $\delta_H$=9.33 (d, 1H), 8.62 (d, 1H), 8.50-8.38 (m, 2H), 7.77 (dd, 1H), 7.57 (t, 1H), 1.83 (s, 6H). LCMS R$_t$=1.35 min in 2.0 min chromatography, 10-80AB, purity 100%, MS ESI calcd. for C$_{16}$H$_{13}$F$_6$N$_4$O [M+H]$^+$ 391.1, found 390.9.

Example 40. Synthesis of Compound 40

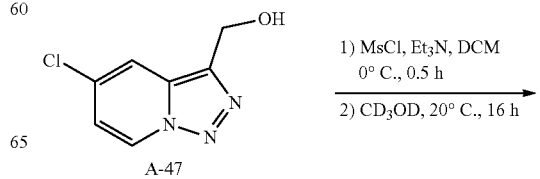

-continued

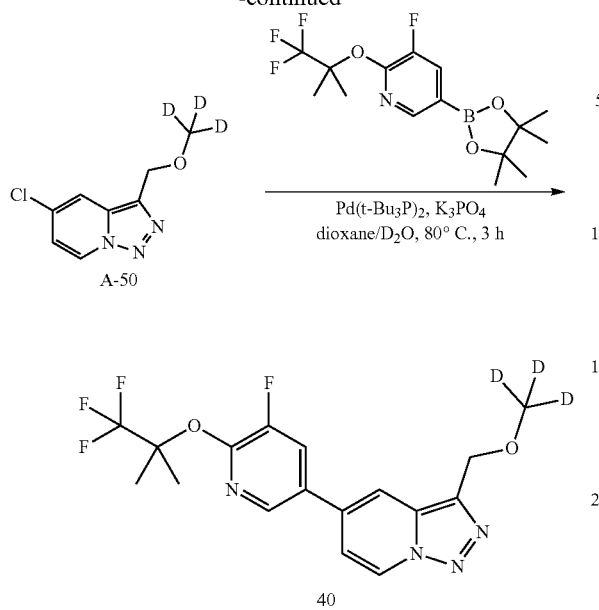

To a mixture of (5-chlorotriazolo[1,5-a]pyridin-3-yl)methanol (350 mg, 1.91 mmol) in DCM (20 mL) was added MsCl (0.26 mL, 3.4 mmol) at 0° C., to the mixture was added Et$_3$N (0.36 mL, 2.6 mmol), then the mixture was stirred at 0° C. for 30 minutes. To the mixture was added CD$_3$OD (15 mL) then the mixture was stirred at 20° C. for 16 hours. The mixture was quenched with sat. NH$_4$Cl (30 mL), then the mixture was extracted with EtOAc (50 mL×2). The combined organic phase was washed with brine (15 mL), dried over Na$_2$SO$_4$, filtered and concentrated to give the crude product. The crude product was purified by flash chromatography on silica gel (EtOAc in PE=0% to 20% to 40%) to give the product (300 mg, 1.50 mmol) as oil. $^1$H NMR (400 MHz, CDCl$_3$) $\delta_H$=8.63 (d, 1H), 7.83 (d, 1H), 6.96 (dd, 1H), 4.88 (s, 2H). LCMS R$_t$=0.66 min in 1.5 min chromatography, 5-95AB, purity 100%, MS ESI calcd. for C$_8$H$_6$D$_3$ClN$_3$O [M+H]$^+$ 201.1, found 201.0.

A mixture of 5-chloro-3-(trideuteriomethoxymethyl)triazolo[1,5-a]pyridine (100 mg, 0.50 mmol), 3-fluoro-5-(4,4,5,5-tetramethyl-1,3,2-dioxaborolan-2-yl)-2-(2,2,2-trifluoro-1,1-dimethyl-ethoxy)pyridine (191.41 mg, 0.55 mmol), Pd(t-Bu$_3$P)$_2$ (38.21 mg, 70.0 µmol) and K$_3$PO$_4$ (211.62 mg, 1 mmol) in 1,4-Dioxane (5 mL) and D$_2$O (1 mL) was stirred at 80° C. for 3 hours under N$_2$. After cooling to room temperature, the mixture was diluted with H$_2$O (10 mL), and the mixture was extracted with EtOAc (20 mL×2). The combined organic phase was washed with water (10 mL) and brine (20 mL), dried over Na$_2$SO$_4$, filtered and concentrated to give the crude product. The crude product was purified by Prep-TLC (silica gel, PE:EtOAc=2:1) to give the impure product, which was triturated from Hexane (5 mL) to give the product (110 mg, 0.28 mmol)) as a solid. $^1$H NMR (400 MHz, CDCl$_3$) $\delta_H$=8.78 (d, 1H), 8.25 (d, 1H), 7.94 (s, 1H), 7.68 (dd, 1H), 7.18 (dd, 1H), 4.96 (s, 2H), 1.88 (s, 6H). LCMS R$_t$=1.27 min in 2.0 min chromatography, 10-80AB, purity 98.01%, MS ESI calcd. for C$_{17}$H$_{14}$D$_3$F$_4$N$_4$O$_2$ [M+H]$^+$ 388.1, found 387.9. MS ESI calcd. for C$_{17}$H$_{14}$D$_3$F$_4$N$_4$O$_2$ [M+H]$^+$ 388.1470, found 388.1500.

Example 41. Synthesis of Compound 41

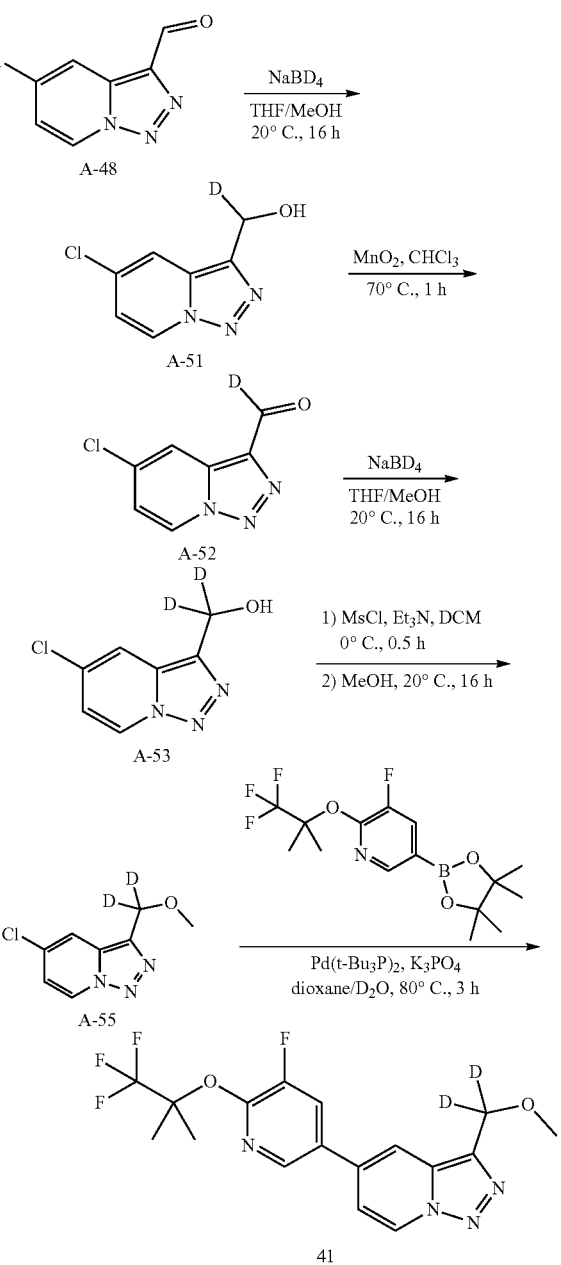

To a mixture of 5-chlorotriazolo[1,5-a]pyridine-3-carbaldehyde (670 mg, 3.69 mmol) in THF (15 mL) and Methanol (15 mL) was added NaBD$_4$ (308.91 mg, 7.38 mmol) at 0° C., then the mixture was stirred at 20° C. for 16 hours. The mixture was quenched with sat. NH$_4$Cl (10 mL), then the mixture was extracted with EtOAc (20 mL×2). The combined organic phase was washed with brine (10 mL), dried over Na$_2$SO$_4$, filtered and concentrated to give the crude product (650 mg, 3.52 mmol, 95% yield) as a solid. $^1$H NMR (400 MHz, CDCl$_3$) $\delta_H$=8.63 (d, 1H), 7.87 (d, 1H), 6.96 (dd, 1H), 5.08 (s, 1H), 2.29 (br s, 1H).

A mixture of (5-chlorotriazolo[1,5-a]pyridin-3-yl)-deuterio-methanol (650 mg, 3.52 mmol) and MnO$_2$ (3.67 g, 42.25 mmol) in Chloroform (30 mL) was stirred at 70° C. for 1 hour. After cooling to room temperature, the mixture was filtered through Celite, eluted with CHCl₃ (15 mL×2), the filtrate was concentrated to give the crude product (550 mg, 3.01 mmol, 86% yield) as a solid. ¹H NMR (400 MHz, CDCl₃) $\delta_H$=8.80 (d, 1H), 8.39 (d, 1H), 7.21 (dd, 1H).

To a mixture of (5-chlorotriazolo[1,5-a]pyridin-3-yl)-deuterio-methanone (550 mg, 3.01 mmol) in THF (10 mL) and Methanol (10 mL) was added NaBD₄ (252.18 mg, 6.02 mmol) at 0° C., then the mixture was stirred at 20° C. for 16 hours. The mixture was quenched with sat. NH₄Cl (20 mL), then the mixture was extracted with EtOAc (50 mL×2). The combined organic phase was washed with brine (30 mL×2), dried over Na₂SO₄, filtered and concentrated to give the crude product (400 mg, 2.16 mmol, 72% yield) as a solid. NMR (400 MHz, CDCl₃) $\delta_H$=8.64 (dd, 1H), 7.87 (d, 1H), 6.97 (dd, 1H), 2.04 (br s, 1H).

To a mixture of (5-chlorotriazolo[1,5-a]pyridin-3-yl)-dideuterio-methanol (250 mg, 1.35 mmol) in DCM (15 mL) was added MSCl (0.17 mL, 2.16 mmol) at 0° C., followed by Et₃N (0.24 mL, 1.75 mmol), then the mixture was stirred at 0° C. for 30 minutes. To the mixture was added Methanol (10 mL) then the mixture was stirred at 20° C. for 16 hours. The mixture was quenched with sat. NH₄Cl (30 mL), then the mixture was extracted with EtOAc (50 mL×2). The combined organic phase was washed with brine (15 mL), dried over Na₂SO₄, filtered and concentrated to give the crude product. The crude product was purified by flash chromatography on silica gel (EtOAc in PE=0% to 20% to 40%) to give the product (130 mg, 0.63 mmol) as an oil. ¹H NMR (400 MHz, CDCl₃) $\delta_H$=8.64 (dd, 1H), 7.83 (dd, 1H), 6.96 (dd, 1H), 3.44 (s, 3H). LCMS R$_t$=0.67 min in 1.5 min chromatography, 5-95AB, purity 96.12%, MS ESI calcd. for C₈H₇D₂ClN₃O [M+H]⁺ 200.0, found 200.0.

A mixture of 5-chloro-3-[dideuterio(methoxy)methyl]triazolo[1,5-a]pyridine (120 mg, 0.60 mmol), 3-fluoro-5-(4,4,5,5-tetramethyl-1,3,2-dioxaborolan-2-yl)-2-(2,2,2-trifluoro-1,1-dimethyl-ethoxy)pyridine (230.85 mg, 0.66 mmol), Pd(t-Bu₃P)₂ (46.08 mg, 90.0 μmol) and K₃PO₄ (255.23 mg, 1.2 mmol) in 1,4-Dioxane (7 mL) and D₂O (1 mL) was stirred at 80° C. for 3 hours under N₂. After cooling to room temperature, the mixture was diluted with H₂O (10 mL), and the mixture was extracted with EtOAc (20 mL×2). The combined organic phase was washed with water (10 mL) and brine (20 mL), dried over Na₂SO₄, filtered and concentrated to give the crude product. The crude product was purified by Prep-TLC (silica gel, PE:EtOAc=2:1) to give the product (92.01 mg, 0.24 mmol) as a solid. ¹H NMR (400 MHz, CDCl₃) $\delta_H$=8.78 (d, 1H), 8.25 (d, 1H), 7.93 (s, 1H), 7.68 (dd, 1H), 7.18 (dd, 1H), 3.46 (s, 3H), 1.88 (s, 6H). LCMS R, =1.30 min in 2.0 min chromatography, 10-80AB, purity 100%, MS ESI calcd. for C₁₇H₁₅D₂F₄N₄O₂ [M+H]⁺ 387.1, found 387.0. MS ESI calcd. for C₁₇H₁₅D₂F₄N₄O₂ [M+H]⁺ 387.1408, found 387.1481.

Example 42. Synthesis of Compound 42

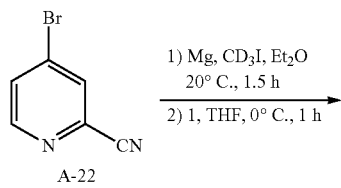

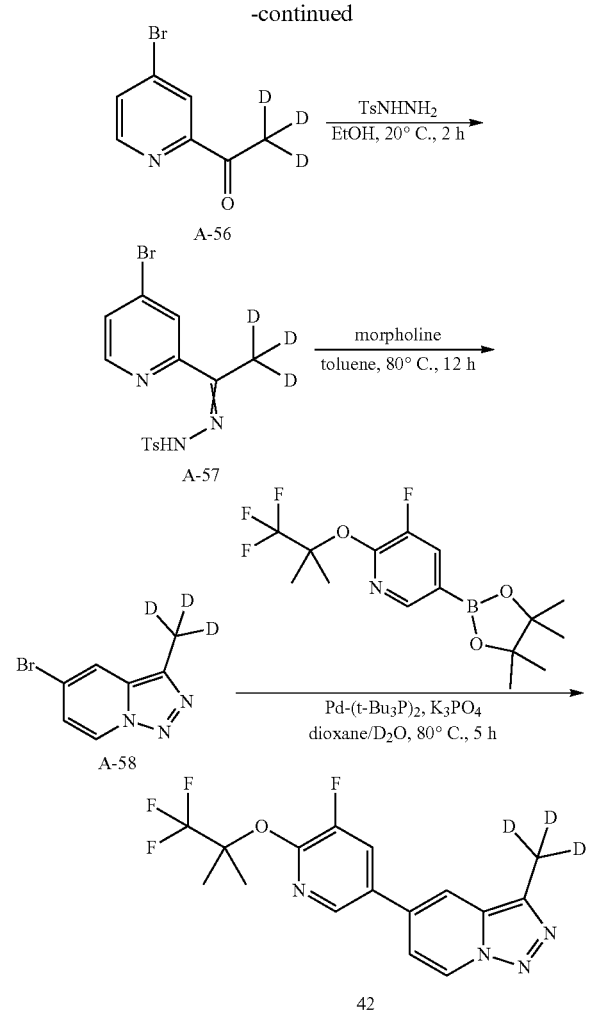

To a mixture of I₂ (50 mg, 0.20 mmol) and Mg (451.64 mg, 18.58 mmol) in Ether (5 mL) was added a solution of CD₃I (3 g, 20.7 mmol) in Ether (6 mL) dropwise under N₂ over 30 minutes. Then the reaction mixture was stirred at 20° C. for 1 hour to give a silver gray solution. To the mixture 4-bromopyridine-2-carbonitrile (1.7 g, 9.29 mmol) in THF (34 mL) was added the solution of CD₃MgI at 0° C., then the mixture was stirred at 0° C. for 1 hour. The reaction mixture was poured into 1N HCl (50 mL) and ice (30 g), then basified with Na₂CO₃ (solid) to pH~8, the mixture was extracted with EtOAc (50 mL×2). The combined organic phase was washed with brine (50 mL), dried over Na₂SO₄, filtered and concentrated to give the crude product. The crude product was purified by flash chromatography on silica gel (EtOAc in PE=0% to 10% to 20%) to give the product (1500 mg, 7.25 mmol, 78% yield) as a solid. ¹H NMR (400 MHz, CDCl₃) $\delta_H$=8.50 (d, 1H), 8.20 (d, 1H), 7.65 (dd, 1H). LCMS R$_t$=0.74 min in 1.5 min chromatography, 5-95AB, purity 98.13%, MS ESI calcd. for C₇H₄D₃BrNO [M+H]⁺ 203.0, found 202.9.

A mixture 4-methylbenzenesulfonohydrazide (1.51 g, 8.13 mmol) and 1-(4-bromo-2-pyridyl)-2,2,2-trideuterio-ethanone (1.5 g, 7.39 mmol) in Ethanol (10 mL) was stirred at 20° C. for 2 hours. The solid was collected by filtered, then was washed with PET (3 mL), dried in oven to give the product (2600 mg, 7.0 mmol, 95% yield) as a solid. ¹H NMR (400 MHz, DMSO-d₆) $\delta_H$=10.98 (s, 1H), 8.44 (d, 1H), 7.87-7.77 (m, 3H), 7.66 (dd, 1H), 7.43 (d, 2H), 2.37 (s, 3H). LCMS $R_t$=0.87 min in 1.5 min chromatography, 5-95AB, purity 100%, MS ESI calcd. for $C_{14}H_{12}D_3BrN_3O_2S$ [M+H+2]$^+$ 373.0, found 373.1.

A mixture of morpholine (0.7 mL, 8.08 mmol) and N-[[1-(4-bromo-2-pyridyl)-2,2,2-trideuterio-ethylidene]amino]-4-methyl-benzenesulfonamide (600 mg, 1.62 mmol) in Toluene (20 mL) was stirred at 80° C. for 12 hours. After cooling to room temperature, the mixture was diluted with EtOAc (30 mL), then washed with 0.5N HCl (20 mL), water (20 mL) and brine (20 mL), dried over Na$_2$SO$_4$, filtered and concentrated to give the crude product. The crude product was purified by flash chromatography on silica gel (EtOAc in PE=0% to 40% to 70%) to give the product (310 mg, 1.43 mmol, 89% yield) as a solid. $^1$H NMR (400 MHz, CDCl$_3$) $\delta_H$=8.52 (dd, 1H), 7.81 (dd, 1H), 6.99 (dd, 1H). LCMS $R_t$=0.61 min in 1.5 min chromatography, purity 99.52%, MS ESI calcd. for $C_7H_4D_3BrN_3$ [M+H]$^+$ 215.0, found 214.9.

A mixture of 5-bromo-3-(trideuteriomethyl)triazolo[1,5-a]pyridine (70 mg, 0.33 mmol), 3-fluoro-5-(4,4,5,5-tetramethyl-1,3,2-dioxaborolan-2-yl)-2-(2,2,2-trifluoro-1,1-dimethyl-ethoxy)pyridine (125 mg, 0.36 mmol), Pd(t-Bu$_3$P)$_2$ (24.95 mg, 50.0 μmop and K$_3$PO$_4$ (138.2 mg, 0.65 mmol) in 1,4-Dioxane (8 mL) and D$_2$O (0.88 mL, 43.68 mmol) was stirred at 80° C. for 5 hours under N$_2$. After cooled to room temperature, the mixture was diluted with H$_2$O (20 mL), and the mixture was extracted with EtOAc (30 mL×2). The combined organic phase was washed with water (20 mL) and brine (20 mL), dried over Na$_2$SO$_4$, filtered and concentrated to give the crude product. The crude product was purified by Prep-TLC (silica gel, PE:EtOAc=3:1) to give the product (51.06 mg, 142.9 μmol, 44% yield) as a solid. $^1$H NMR (400 MHz, CDCl$_3$) $\delta_H$=8.73 (d, 1H), 8.24 (d, 1H), 7.72 (s, 1H), 7.67 (d, 1H), 7.11 (d, 1H), 1.87 (s, 6H). LCMS $R_t$=1.32 min in 2.0 min chromatography, 5-95AB, purity 100%, MS ESI calcd. for $C_{16}H_{12}D_3F_4N_4O$ [M+H]$^+$ 358.1, found 358.1. MS MS ESI calcd. for $C_{16}H_{12}D_3F_4N_4O$ [M+H]$^+$ 358.1365, found 358.1383.

Example 43. Synthesis of Compound 43

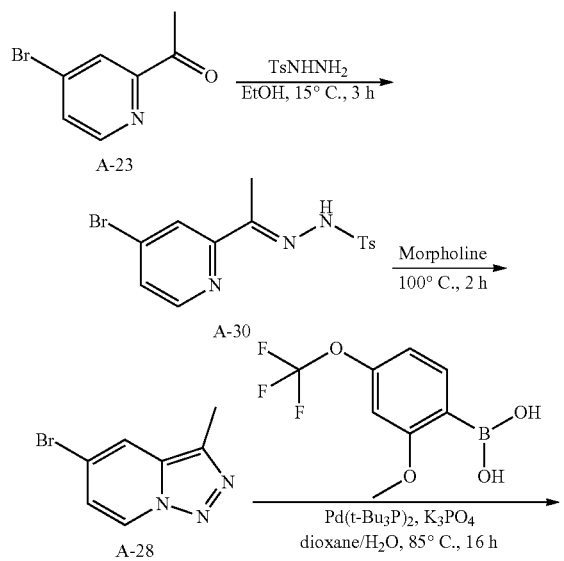

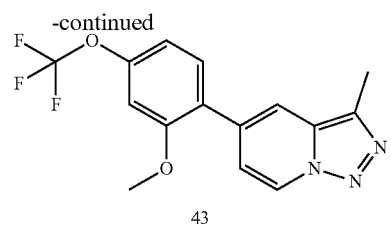

A mixture of 1-(4-bromo-2-pyridyl)ethanone (2 g, 10 mmol) and 4-methylbenzenesulfonohydrazide (2.79 g, 15 mmol) in Ethanol (30 mL) was stirred at 15° C. for 3 hours to give a mixture. The reaction mixture was concentrated to give the crude product (3700 mg, 7.34 mmol, 73% yield) as a solid. LCMS $R_t$=0.86 min in 1.5 min chromatography, 5-95AB, purity 73.06%, MS ESI calcd. for $C_{14}H_{15}BrN_3O_2S$ [M+H+2]$^+$ 470.0, found 370.0.

A mixture of N-[1-(4-bromo-2-pyridyl)ethylideneamino]-4-methyl-benzenesulfonamide (3.7 g, 10.05 mmol) in morpholine (30 g, 344.35 mmol) was stirred at 100° C. for 2 hours. After cooling to room temperature, the reaction mixture was concentrated. The residue was purified by flash chromatography on silica gel (EtOAc in PE=0% to 10% to 20%) to give the product (2100 mg, 9.35 mmol, 93% yield) as a solid. $^1$H NMR (400 MHz, CDCl$_3$) $\delta_H$=8.51 (dd, 1H), 7.81 (d, 1H), 6.99 (dd, 1H), 2.59 (s, 3H). LCMS $R_1$=0.70 min in 1.5 min chromatography, 5-95AB, purity 94.46%, MS ESI calcd. for $C_7H_7BrN_3$ [M+H]$^+$ 212.0, found 211.7.

A mixture of 5-bromo-3-methyl-triazolo[1,5-a]pyridine (100 mg, 0.47 mmol), [2-methoxy-4-(trifluoromethoxy)phenyl]boronic acid (133.53 mg, 0.57 mmol), Pd(t-Bu$_3$P)$_2$ (36.15 mg, 0.07 mmol), and K$_3$PO$_4$ (200.24 mg, 0.94 mmol) in 1,4-Dioxane (6 mL) and Water (1 mL) was stirred at 85° C. for 16 hours. After cooling to room temperature, the suspension was diluted with EtOAc (10 mL), filtered through silica gel, eluted with EtOAc (20 mL). The combined filtrates were concentrated to give the crude product. The crude product was purified by flash chromatography on silica gel (EtOAc in PE=0% to 30% to 50%) to give the product (142.76 mg, 0.44 mmol, 94% yield) as a solid. $^1$H NMR (400 MHz, CDCl$_3$) $\delta_H$=8.64 (d, 1H), 7.67 (s, 1H), 7.40 (d, 1H), 7.13 (dd, 1H), 6.96 (dd, 1H), 6.87 (s, 1H), 3.88 (s, 3H), 2.65 (s, 3H). LCMS $R_t$=1.28 min in 2 min chromatography, 10-80AB, purity 100%, MS ESI calcd. for $C_{15}H_{13}F_3N_3O_2$ [M+H]$^+$ 324.1, found 423.9.

Example 44. Synthesis of Compound 44

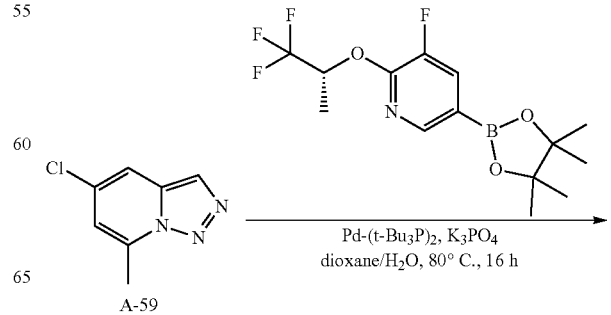

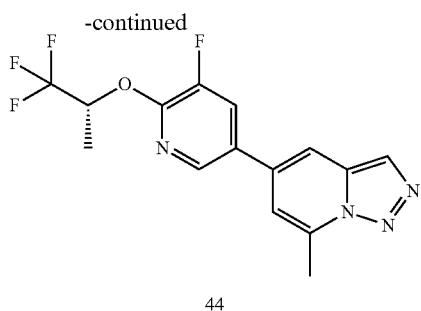

44

A mixture of 3-fluoro-5-(4,4,5,5-tetramethyl-1,3,2-dioxaborolan-2-yl)-2-[(1R)-2,2,2-trifluoro-1-methyl-ethoxy]pyridine (285.91 mg, 0.85 mmol), 5-chloro-7-methyl-triazolo[1,5-a]pyridine (130 mg, 0.78 mmol), Pd(t-Bu₃P)₂ (59.46 mg, 0.12 mmol) and K₃PO₄ (329.34 mg, 1.55 mmol) in 1,4-Dioxane (5 mL) and Water (1 mL) was stirred at 80° C. for 16 hours under N₂. After cooling to room temperature, the mixture was filtered through Celite and eluted with EtOAc (20 mL×2), and the filtrate was concentrated to give the crude product. The crude product was purified by flash chromatography on silica gel (EtOAc in PE=0% to 30%) to give the impure product. The impure product was triturated from n-hexane/CH₂Cl₂ (2:1, 3 ml) to give the product 10.28 mg, 29.6 µmol, 4% yield) as a solid. ¹H NMR (400 MHz, CDCl₃+D₂O) δ$_H$=8.24-8.21 (m, 1H), 8.18 (s, 1H), 7.75 (s, 1H), 7.68 (dd, 1H), 6.98 (s, 1H), 5.94-5.84 (m, 1H), 2.99 (s, 3H), 1.59 (d, 3H). LCMS R$_f$=1.26 min in 2.0 min chromatography, purity, 100%, MS ESI calcd. for C₁₅H₁₃F₄N₄O [M+H]⁺ 341.1, found 340.9.

Example 45. Synthesis of Compound 45

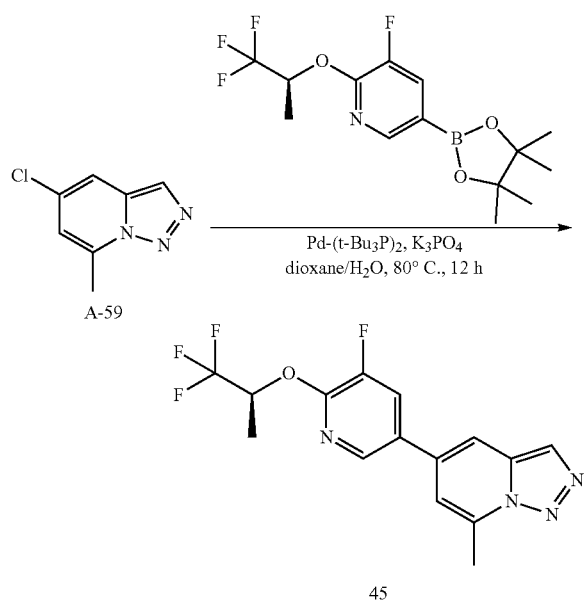

45

A mixture of 5-chloro-7-methyl-triazolo[1,5-a]pyridine (150 mg, 0.89 mmol), 3-fluoro-5-(4,4,5,5-tetramethyl-1,3,2-dioxaborolan-2-yl)-2-[(1S)-2,2,2-trifluoro-1-methyl-ethoxy]pyridine (359.89 mg, 1.07 mmol), K₃PO₄ (379.96 mg, 1.79 mmol), Pd(t-Bu₃P)₂ (68.61 mg, 0.13 mmol) in 1,4-Dioxane (5 mL) and Water (0.50 mL) was stirred at 80° C. for 12 hours. After cooling to room temperature, the reaction mixture was diluted with water (15 mL) and extracted with ethyl acetate (15 mL×2). The combined organic phase was washed with water (30 mL), brine (30 mL), dried over Na₂SO₄ and concentrated to give the crude product. The crude product was purified by Prep-HPLC (Boston Prime C18 (150×30 mm, 5 urn), A=H₂O (0.05% NH₄OH) and B=CH₃CN; 54-74% B over 9 minutes) to give the product (8.4 mg, 24.7 µmol, 3% yield) as a solid. ¹H NMR (400 MHz, CDCl₃) δ$_H$=8.22 (d, 1H), 8.18 (s, 1H), 7.75 (s, 1H), 7.68 (dd, 1H), 6.98 (s, 1H), 5.95-53.84 (m, 1H), 2.99 (s, 3H), 1.60 (s, 3H). LCMS R$_f$=1.29 min in 2.0 min chromatography, 10-80AB, purity 100%, MS ESI calcd. C₁₅H₁₃F₄N₄O [M+H]⁺ 341.09, found 341.0.

Example 46. Synthesis of Compound 46

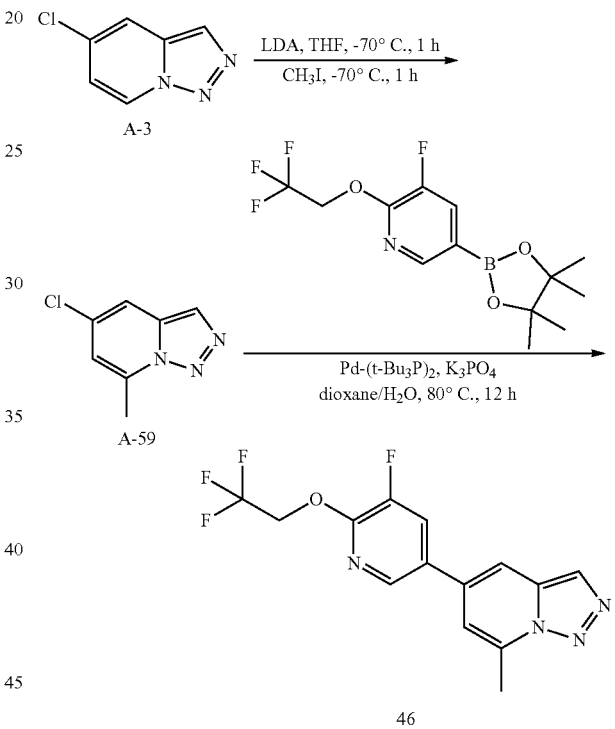

46

To a solution of 5-chlorotriazolo[1,5-a]pyridine (500 mg, 3.26 mmol) in THF (30 mL) was added LDA (2.44 mL, 4.88 mmol) at −70° C. After the addition, the solution was stirred at −70° C. for 1 hours. To the mixture was added CH₃I (1.57 mL, 25.15 mmol) at −70° C., and the mixture was stirred at −70° C. for 1 hour. The mixture was quenched with sat. NH₄Cl (50 mL), then the mixture was extracted with EtOAc (50 mL×2). The combined organic phase was washed with brine (30 mL), dried over Na₂SO₄, filtered and concentrated to give the crude product. The crude product was purified by flash chromatography on silica gel (EtOAc in PE=0% to 20% to 40%) to give the product (470 mg, 2.80 mmol, 86% yield) as a solid. ¹H NMR (400 MHz, CDCl₃) δ$_H$=8.08-8.03 (m, 1H), 7.64 (d, 1H), 6.79 (d, 1H), 2.90 (s, 3H).

A mixture of 5-chloro-7-methyl-triazolo[1,5-a]pyridine (150 mg, 0.89 mmol), 3-fluoro-5-(4,4,5,5-tetramethyl-1,3,2-dioxaborolan-2-yl)-2-(2,2,2-trifluoroethoxy)pyridine (344.84 mg, 1.07 mmol), K₃PO₄ (379.96 mg, 1.79 mmol), Pd(t-Bu₃P)₂ (68.61 mg, 0.13 mmol) in 1,4-Dioxane (5 mL)

and Water (0.50 mL) was stirred at 80° C. for 12 hours. After cooling to room temperature, the reaction mixture was diluted with water (15 mL) and extracted with ethyl acetate (15 mL×2). The combined organic phase was washed with water (30 mL), brine (30 mL), dried over $Na_2SO_4$ and concentrated to give the crude product. The crude product was purified by Prep-HPLC (Boston Prime C18 (150 mm×30 mm, 5 μm), A=$H_2O$ (0.05% $NH_4OH$) and B=$CH_3CN$; 60-80% B over 9 minutes) to give the product (14.72 mg, 44.4 μmol, 5% yield) as a solid. $^1H$ NMR (400 MHz, $CDCl_3$) $\delta_H$=8.23 (d, 1H), 8.19 (s, 1H), 7.76 (d, 1H), 7.70 (dd, 1H), 6.98 (d, 1H), 4.92 (q, 2H), 2.99 (s, 3H). LCMS $R_t$=1.22 min in 2.0 min chromatography, 10-80AB, purity 99.23%, MS ESI calcd. $C_{14}H_{11}F_4N_4O$ $[M+H]^+$ 327.08, found 326.9.

Example 47. Efficacy of Exemplary Compounds in the Modulation of Late Sodium Current (INaL)

Functional characterization of exemplary compounds to modulate INaL expressed by the $Na_v1.6$ voltage-gated sodium channel was accomplished using the PatchXpress™ high throughput electrophysiology platform (Molecular Devices, Sunnyvale, CA). HEK-293 cells expressing recombinant, human $Na_v1.6$ ($hNa_v1.6$) were grown in DMEM/high-glucose Dulbecco's modified, 10% FBS, 2 mM sodium pyruvate, 10 mM HEPES and 400 μg/mL G418. Cells were grown to 50%-80% confluency prior to harvesting. Trypsinized cells were washed, allowed to recover for 1 hour and then resuspended in extracellular recording solution at a concentration of $1\times10^6$ cells/ml. The onboard liquid handling facility of the PatchXpress was used for dispensing cells and applying test compounds. Nav late currents were evoked by the application of 300 nM ATX-II. INaL was evoked by depolarizing pulses to 0 mV for 200 ms from a non-inactivating holding potential (e.g., −120 mV) at a frequency of 0.1 Hz. INaL amplitude and stability were determined by analyzing the mean current amplitude over the final 20 ms of the test pulse. Following steady state block with exemplary compounds (e.g., as described herein), a $Na^+$ free solution containing an impermeant cation (e.g., Choline or NDMG) was added to confirm the identify of the sodium current. Percent steady-state inhibition of INaL was calculated as: [(INaL_compound)/(INaL_control)]*100, where INaL_compound and INaL_control represent INaL recorded in the presence or absence of compound, respectively.

Results from this assay relating to percent inhibition of INaL at hNaV1.6 (measured using a procedure similar to described above but using HEK-293 cells expressing recombinant, human Nav 1.6 (h Nav 1.6) at 1 μM are summarized in Table 1 below. In this table, "A" indicates inhibition of less than 30%; "B" indicates inhibition of between about 30% to about 70%; and "C" indicates inhibition of greater than 70%.

TABLE 1

| Compound | INaL v1.6 (1 μM, % Inhibition) |
|---|---|
| 1 | B |
| 2 | C |
| 3 | C |
| 4 | C |
| 5 | C |
| 6 | B |
| 7 | C |

TABLE 1-continued

| Compound | INaL v1.6 (1 μM, % Inhibition) |
|---|---|
| 8 | B |
| 9 | C |
| 10 | B |
| 11 | C |
| 12 | C |
| 13 | C |
| 14 | B |
| 15 | C |
| 16 | B |
| 17 | C |
| 18 | C |
| 19 | B |
| 20 | B |
| 21 | C |
| 22 | C |
| 23-1 | B |
| 23-2 | C |
| 24 | C |
| 25 | C |
| 26 | C |
| 27 | C |
| 28 | C |
| 29 | C |
| 30 | C |
| 31 | C |
| 32 | C |
| 33 | C |
| 34 | C |
| 35 | C |
| 36 | C |
| 37 | C |
| 38 | C |
| 39 | C |
| 40 | C |
| 41 | C |
| 42 | C |
| 43 | C |
| 44 | B |
| 45 | C |
| 46 | B |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A method of treating a neurological disorder, wherein the neurological disorder is epilepsy or an epilepsy syndrome, wherein the method comprises administering to a subject in need thereof a compound of Formula (I):

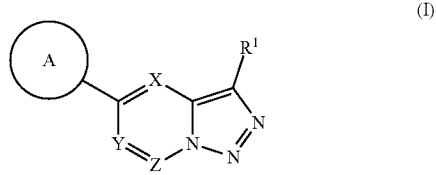

(I)

or a pharmaceutically acceptable salt thereof, wherein:
each of X, Y, and Z is CR';
A is phenyl or pyridyl, wherein the phenyl and the pyridyl are substituted with one or more $R^3$;
R' is hydrogen or $C_{1-6}$ alkyl;
$R^1$ is selected from the group consisting of hydrogen, deuterium and $C_{1-6}$ alkyl, wherein the $C_{1-6}$ alkyl is optionally substituted with one or more $R^4$;
each $R^3$ is independently selected from the group consisting of $C_{1-6}$ alkyl, $C_{3-8}$ carbocyclyl, fluoro, chloro and —$OR^c$, wherein the $C_{1-6}$ alkyl and $C_{3-8}$ carbocyclyl are optionally substituted with one or more $R^5$;

each of $R^4$ is independently selected from the group consisting of deuterium, fluoro, oxo, cyano, nitro and —$OR^c$;
each of $R^5$ is independently selected from the group consisting of $C_{1-6}$ alkyl, deuterium, halogen, oxo, cyano, nitro, and —$OR^c$, wherein the $C_{1-6}$ alkyl is optionally substituted with one or more $R^7$;
each $R^c$ is independently selected from the group consisting of hydrogen, deuterium, $C_{1-6}$ alkyl and $C_{3-8}$ carbocyclyl wherein the $C_{1-6}$ alkyl and $C_{3-8}$ carbocyclyl are optionally substituted with one or more $R^6$;
each $R^6$ is independently selected from the group consisting of $C_{1-6}$ alkyl, deuterium, $C_{1-6}$ haloalkyl, $C_{3-8}$ carbocyclyl, halogen, cyano, nitro, and —OH; and
and each $R^7$ is independently selected from the group consisting of $C_{1-6}$ alkyl, halogen and oxo.

2. The method of claim 1, wherein the neurological disorder is epilepsy.
3. The method of claim 1, wherein the neurological disorder is an epileptic encephalopathy.
4. The method of claim 3, wherein the epileptic encephalopathy comprises Dravet syndrome, infantile spasms, or Lennox-Gastaut syndrome.
5. The method of claim 1, wherein A is pyridyl.
6. The method of claim 1, wherein A is a phenyl.
7. The method of claim 1, wherein $R^3$ is $C_{1-6}$ alkyl or —$OR^c$.
8. The method of claim 7, wherein $R^3$ is $C_{1-6}$ alkyl.
9. The method of claim 7, wherein $R^3$ is —$OR^c$.
10. The method of claim 9, wherein $R^c$ is $C_{1-6}$ alkyl substituted with one or more $R^6$.
11. The method of claim 10, wherein $R^3$ is —$OCF_3$.
12. The method of claim 1, wherein $R^1$ is hydrogen or $C_{1-6}$ alkyl.
13. The method of claim 12, wherein $R^1$ is hydrogen.
14. The method of claim 12, wherein $R^1$ is $C_{1-6}$ alkyl.
15. The method of claim 14, wherein $R^1$ is $C_{1-4}$ alkyl substituted with 1 to 3 $R^4$.
16. The method of claim 1, wherein the compound of Formula (I) is a compound of Formula (I-a):

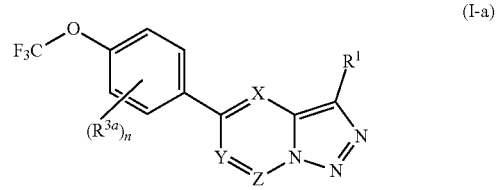

(I-a)

or pharmaceutically acceptable salt thereof, wherein:
each of X, Y, and Z is CR';
R' is hydrogen or $C_{1-6}$ alkyl;
$R^1$ is selected from the group consisting of hydrogen, deuterium and $C_{1-6}$ alkyl, wherein the $C_{1-6}$ alkyl is optionally substituted with one or more of $R^4$;
each $R^{3a}$ is independently selected from the group consisting of $C_{1-6}$ alkyl, $C_{3-8}$ carbocyclyl, fluoro, chloro and —$OR^c$, wherein the $C_{1-6}$ alkyl and $C_{3-8}$ carbocyclyl are optionally substituted with one or more $R^5$;
each $R^4$ is independently selected from the group consisting of fluoro, oxo, cyano, nitro and —$OR^c$;
each $R^5$ is independently selected from the group consisting of $C_{1-6}$ alkyl, halogen, oxo, cyano, nitro and —OR$^c$, wherein the C$_{1-6}$ alkyl is optionally substituted with one or more R$^7$;
n is selected from the group consisting of 0, 1 and 2;
each R$^c$ is independently selected from the group consisting of hydrogen, C$_{1-6}$ alkyl and C$_{3-8}$ carbocyclyl, wherein the C$_{1-6}$ alkyl and C$_{3-8}$ carbocyclyl are optionally substituted with one or more R$^6$;
each R$^6$ is independently selected from the group consisting of C$_{1-6}$ alkyl, C$_{3-8}$ carbocyclyl, halo, cyano, nitro and —OH; and
each R$^7$ is independently selected from the group consisting of C$_{1-6}$ alkyl, halogen and oxo.

17. The method of claim 1, wherein the compound of Formula (I) is a compound of Formula (I-b):

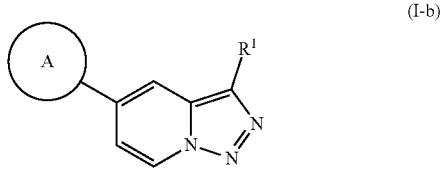

(I-b)

or a pharmaceutically acceptable salt thereof, wherein:
A is phenyl or pyridyl, wherein the phenyl and pyridyl are substituted by with one or more R$^3$,
R$^1$ is selected from the group consisting of hydrogen, deuterium and C$_{1-6}$ alkyl, wherein the C$_{1-6}$ alkyl is optionally substituted with one or more R$^4$;
each R$^3$ is independently selected from the group consisting of C$_{1-6}$ alkyl, C$_{3-8}$ carbocyclyl, fluoro, chloro and —OR$^c$, wherein C$_{1-6}$ alkyl and C$_{3-8}$ carbocyclyl are optionally substituted with one or more R$^5$;
each R$^4$ is independently selected from the group consisting of deuterium, fluoro, oxo, cyano, nitro and —OR$^c$;
each R$^5$ is independently selected from the group consisting of C$_{1-6}$ alkyl, deuterium, halogen, oxo, cyano, nitro and —OR$^c$, wherein the C$_{1-6}$ alkyl is optionally substituted with one or more R$^7$;
each R$^c$ is independently selected from the group consisting of hydrogen, deuterium and C$_{1-6}$ alkyl, wherein the C$_{1-6}$ alkyl is optionally substituted with one or more R$^6$;
each R$^6$ is independently selected from the group consisting of C$_{1-6}$ alkyl, deuterium, C$_{1-6}$ haloalkyl, C$_{3-8}$ carbocyclyl, halogen, cyano, nitro and —OH; and
each R$^7$ is independently selected from the group consisting of C$_{1-6}$ alkyl, halogen and oxo.

18. The method of claim 1, wherein the compound is selected from the group consisting of:

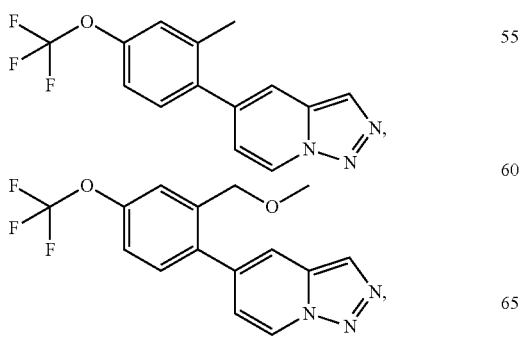

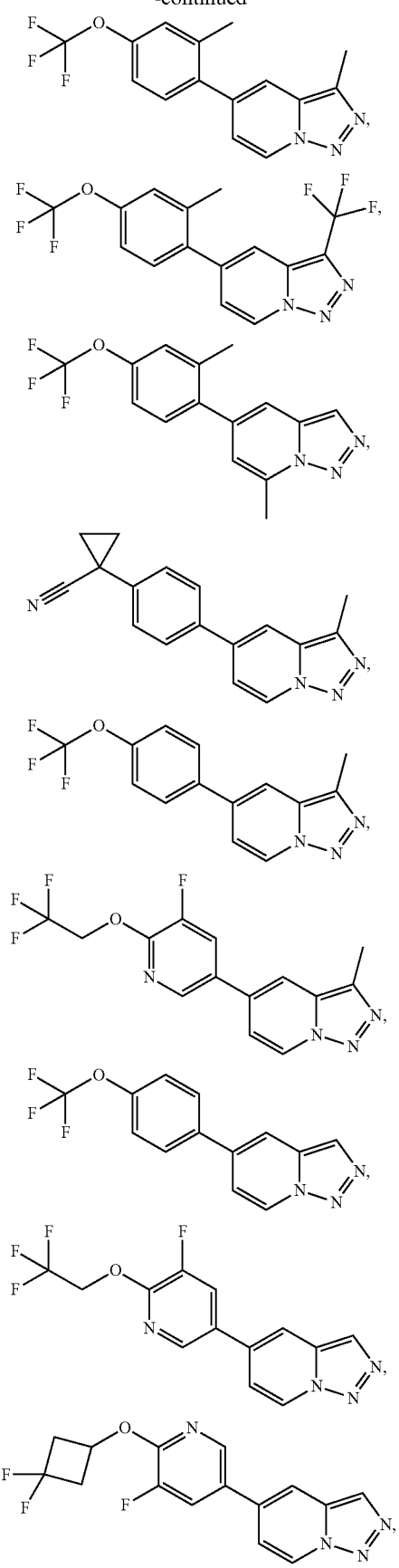

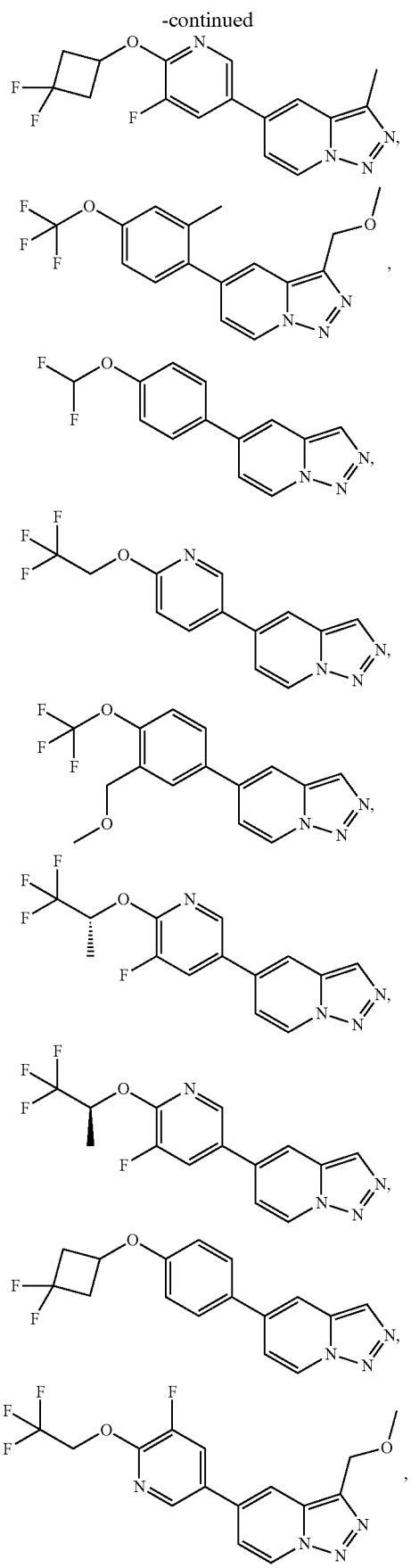

107
-continued
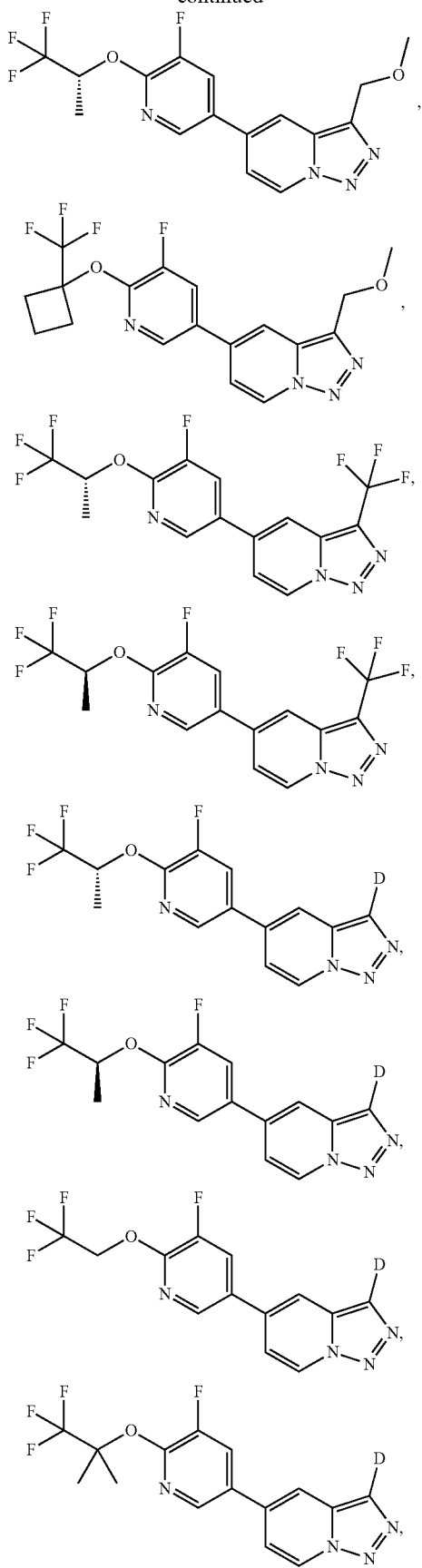
108
-continued
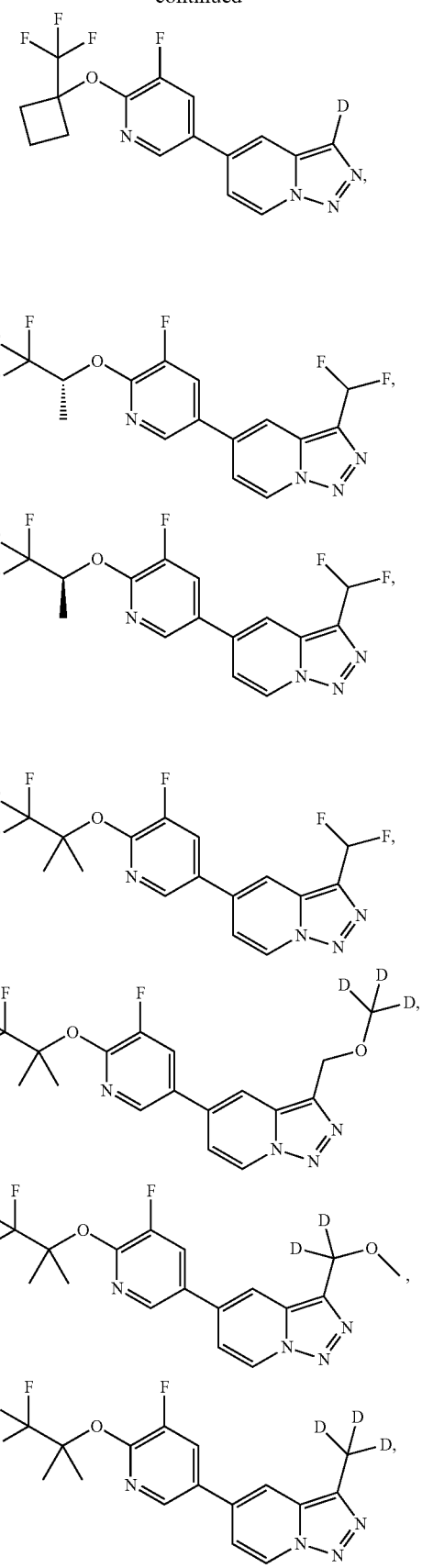

-continued
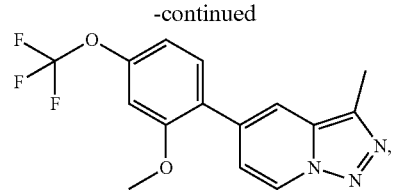
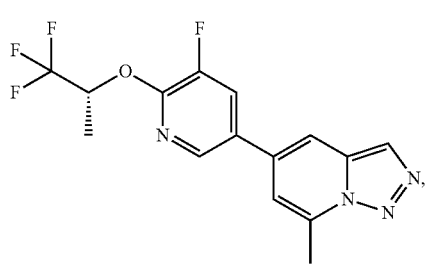 [SMILES: Cc1cc(-c2cnc(OCC(F)(F)F)c(F)c2)cc2cnnn12]
-continued
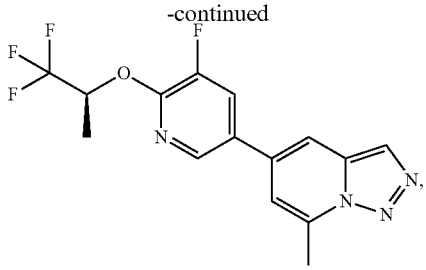
and a pharmaceutically acceptable salt thereof.
19. The method of claim 1, wherein the neurological disorder is a genetic epilepsy or a genetic epilepsy syndrome.
* * * * *